(12) United States Patent
Abraham

(10) Patent No.: US 11,850,006 B2
(45) Date of Patent: Dec. 26, 2023

(54) DEVICES AND METHODS FOR IMAGE-GUIDED PERCUTANEOUS CARDIAC VALVE IMPLANTATION AND REPAIR

(71) Applicant: INNOSCION LLC, San Francisco, CA (US)

(72) Inventor: Theodore P. Abraham, San Francisco, CA (US)

(73) Assignee: INNOSCION LLC, San Francisco, CA (US)

(*) Notice: Subject to any disclaimer, the term of this patent is extended or adjusted under 35 U.S.C. 154(b) by 686 days.

(21) Appl. No.: 16/390,674

(22) Filed: Apr. 22, 2019

(65) Prior Publication Data

US 2019/0254758 A1    Aug. 22, 2019

Related U.S. Application Data

(63) Continuation of application No. 16/016,205, filed on Jun. 22, 2018, now abandoned.
(Continued)

(51) Int. Cl.
*A61B 5/00* (2006.01)
*A61B 34/20* (2016.01)
(Continued)

(52) U.S. Cl.
CPC ............ *A61B 34/20* (2016.02); *A61B 8/0841* (2013.01); *A61B 8/0883* (2013.01); *A61B 8/12* (2013.01);
(Continued)

(58) Field of Classification Search
CPC ....... A61B 8/0841; A61B 8/0883; A61B 8/12; A61B 8/445; A61B 34/20; A61B 34/2663
See application file for complete search history.

(56) References Cited

U.S. PATENT DOCUMENTS 3,556,079 A   1/1971  Omizo
3,612,050 A   10/1971 Sheridan
(Continued)

FOREIGN PATENT DOCUMENTS

CA    2376103 A1   3/2001
DE    19939791 A1  2/2001

*Primary Examiner* — Joel F Brutus
(74) *Attorney, Agent, or Firm* — Brown Rudnick LLP; Adam M. Schoen

(57) ABSTRACT

Devices and methods for ultrasound image-guided percutaneous, cardiac valve implantation and repair comprise, in combination, a plurality of devices including but not limited to an ultrasound-image guided catheter, a pericardial sheath, a cardiac-valve delivery system and an ascending aortic filter. An image-guided catheter is utilized to introduce via an introducer needle and a guide wire a pericardium portal for permitting entry from the chest wall to inside the pericardial space between the pericardial outer lining and inner lining. The pericardium portal permits the use of ultrasound vision to locate a site proximate the left ventricular apex, for introduction of a sheath via a .myocardium needle into the left ventricular space at an angle and avoiding any coronaries or vessels. A first delivery system permits placement of at least one aortic filter which collects any emboli, particulate matter, plaque and prevents such matter travelling via the ascending aorta to the brain, causing a stroke. A second delivery system permits placement of an aortic and/or mitral valve replacement or repair using several types of repair tools.

18 Claims, 49 Drawing Sheets

Related U.S. Application Data

(60) Provisional application No. 62/527,905, filed on Jun. 30, 2017.

(51) Int. Cl.
| | | |
|---|---|---|
| *A61B 8/08* | (2006.01) | |
| *A61F 2/24* | (2006.01) | |
| *A61B 17/34* | (2006.01) | |
| *A61B 8/12* | (2006.01) | |
| *A61B 8/00* | (2006.01) | |
| *A61B 10/04* | (2006.01) | |
| *A61B 17/00* | (2006.01) | |
| *A61F 2/01* | (2006.01) | |
| *A61M 25/09* | (2006.01) | |
| *A61B 17/06* | (2006.01) | |
| *A61B 17/12* | (2006.01) | |
| *A61B 90/00* | (2016.01) | |

(52) U.S. Cl.
CPC .............. *A61B 8/445* (2013.01); *A61B 10/04* (2013.01); *A61B 17/0057* (2013.01); *A61B 17/3403* (2013.01); *A61F 2/0105* (2020.05); *A61F 2/2427* (2013.01); *A61B 17/3421* (2013.01); *A61B 17/3478* (2013.01); *A61B 2017/00243* (2013.01); *A61B 2017/00247* (2013.01); *A61B 2017/00575* (2013.01); *A61B 2017/00592* (2013.01); *A61B 2017/00606* (2013.01); *A61B 2017/00619* (2013.01); *A61B 2017/00623* (2013.01); *A61B 2017/00783* (2013.01); *A61B 2017/06052* (2013.01); *A61B 2017/06171* (2013.01); *A61B 2017/12018* (2013.01); *A61B 2017/3413* (2013.01); *A61B 2034/2063* (2016.02); *A61B 2090/3782* (2016.02); *A61F 2/013* (2013.01); *A61F 2230/0067* (2013.01); *A61M 25/09* (2013.01)

(56) References Cited

U.S. PATENT DOCUMENTS

| | | |
|---|---|---|
| 4,092,867 A | 6/1978 | Matzuk |
| 4,327,709 A | 5/1982 | Hanson et al. |
| 4,540,411 A | 9/1985 | Bodicky |
| 4,581,025 A | 4/1986 | Timmermans |
| 4,840,613 A | 6/1989 | Balbierz |
| 4,869,258 A | 9/1989 | Hetz |
| 5,011,469 A | 4/1991 | Buckberg et al. |
| 5,068,638 A | 11/1991 | Bickely et al. |
| 5,106,368 A | 4/1992 | Uldall et al. |
| 5,159,931 A | 11/1992 | Pini |
| 5,181,514 A | 1/1993 | Solomon et al. |
| 5,437,283 A | 8/1995 | Ranalletta et al. |
| 5,454,373 A | 10/1995 | Koger et al. |
| 5,505,088 A | 4/1996 | Chandraratna et al. |
| 5,509,909 A | 4/1996 | Moy |
| 5,701,901 A | 12/1997 | Lum et al. |
| 5,704,361 A | 1/1998 | Seward et al. |
| 5,762,066 A | 6/1998 | Law et al. |
| 5,967,984 A | 10/1999 | Chu et al. |
| 5,997,497 A | 12/1999 | Nita et al. |
| 6,110,121 A | 8/2000 | Lenker |
| 6,149,598 A | 11/2000 | Tanaka |
| 6,162,179 A | 12/2000 | Moore |
| 6,190,353 B1 | 2/2001 | Makower et al. |
| 6,238,336 B1 | 5/2001 | Ouchi |
| 6,248,081 B1 | 6/2001 | Nishtalas et al. |
| 6,254,573 B1 | 7/2001 | Haim et al. |
| 6,261,234 B1 | 7/2001 | Lin |
| 6,306,097 B1 | 10/2001 | Park et al. |
| 6,368,280 B1 | 4/2002 | Cermak et al. |
| 6,376,319 B2 | 4/2002 | Ang et al. |
| 6,505,088 B1 | 1/2003 | Simkin et al. |
| 6,572,551 B1 | 6/2003 | Smith et al. |
| 6,582,390 B1 | 6/2003 | Sanderson |
| 6,592,526 B1 | 7/2003 | Lenker |
| 6,592,559 B1 | 7/2003 | Pakter et al. |
| 6,685,648 B2 | 2/2004 | Flaherty et al. |
| 6,689,062 B1 | 2/2004 | Mesallum |
| 6,726,677 B1 | 4/2004 | Flaherty et al. |
| 6,855,115 B2 | 2/2005 | Fonseca et al. |
| 7,100,614 B2 | 9/2006 | Stevens et al. |
| 7,191,015 B2 | 3/2007 | Lamson et al. |
| 7,211,054 B1 | 5/2007 | Francis et al. |
| 7,241,267 B2 | 7/2007 | Furia |
| 7,270,634 B2 | 9/2007 | Scampini et al. |
| 7,316,655 B2 | 1/2008 | Garibotto et al. |
| 7,318,806 B2 | 1/2008 | Kohno |
| 7,488,289 B2 | 2/2009 | Suorsa et al. |
| 7,662,089 B2 | 2/2010 | Okada et al. |
| 7,713,190 B2 | 5/2010 | Brock et al. |
| 7,860,555 B2 | 12/2010 | Saadat |
| 7,860,556 B2 | 12/2010 | Saadat |
| 8,199,685 B2 | 6/2012 | Hwang |
| 9,149,251 B2 | 10/2015 | Steffen |
| 2001/0023323 A1 | 9/2001 | Nishtala et al. |
| 2002/0077568 A1 | 6/2002 | Haddock |
| 2002/0123698 A1 | 9/2002 | Garibotto et al. |
| 2003/0139677 A1 | 7/2003 | Fonseca et al. |
| 2003/0199767 A1 | 10/2003 | Cespedes et al. |
| 2003/0229286 A1 | 12/2003 | Lenker |
| 2004/0015193 A1 | 1/2004 | Lamson et al. |
| 2004/0102804 A1 | 5/2004 | Chin |
| 2005/0090709 A1 | 4/2005 | Okada et al. |
| 2005/0096642 A1 | 5/2005 | Appling et al. |
| 2005/0143664 A1 | 6/2005 | Chen et al. |
| 2006/0106315 A1 | 5/2006 | Edens |
| 2007/0293724 A1 | 12/2007 | Saadat et al. |
| 2008/0091104 A1* | 4/2008 | Abraham ................ A61B 8/54 600/439 |
| 2008/0183080 A1* | 7/2008 | Abraham ............ A61B 1/3132 600/466 |
| 2010/0022920 A1* | 1/2010 | Nita ................ A61B 17/22012 601/2 |
| 2011/0196397 A1* | 8/2011 | Frantz ............ A61M 25/09041 606/159 |
| 2011/0213459 A1* | 9/2011 | Garrison ................ A61F 2/013 623/2.11 |
| 2016/0302924 A1* | 10/2016 | Boutillette ............ B29C 70/74 |

\* cited by examiner

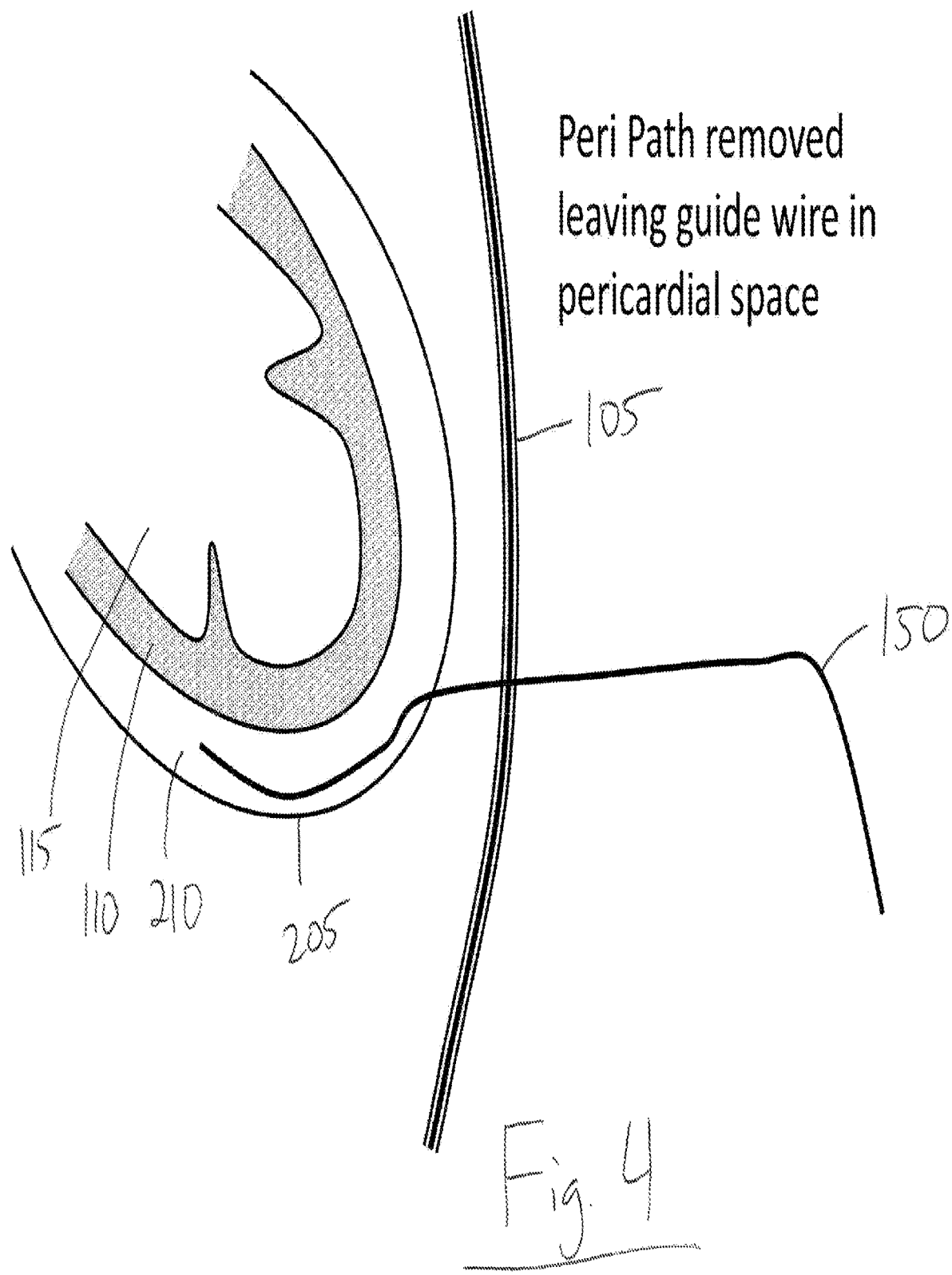

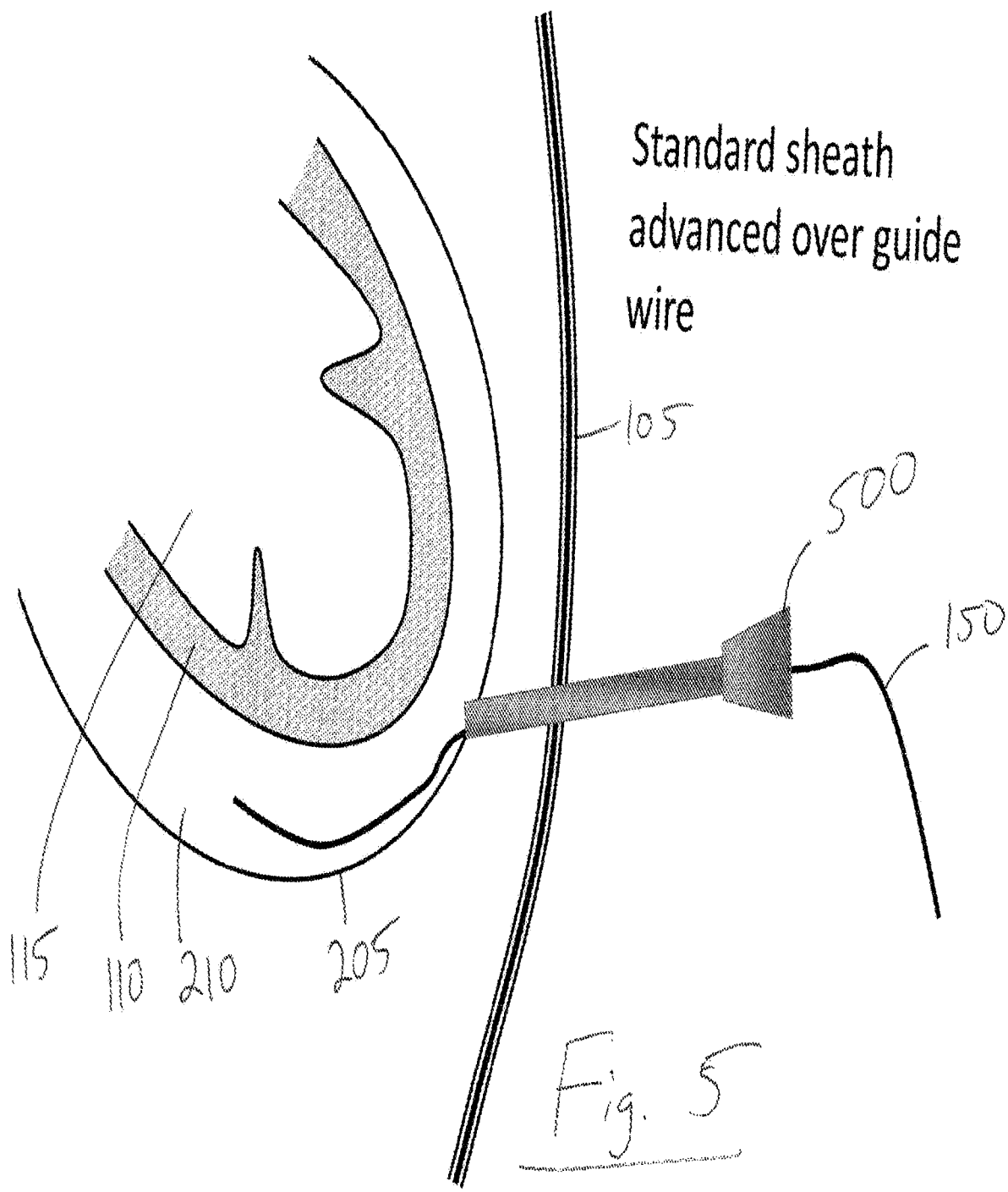

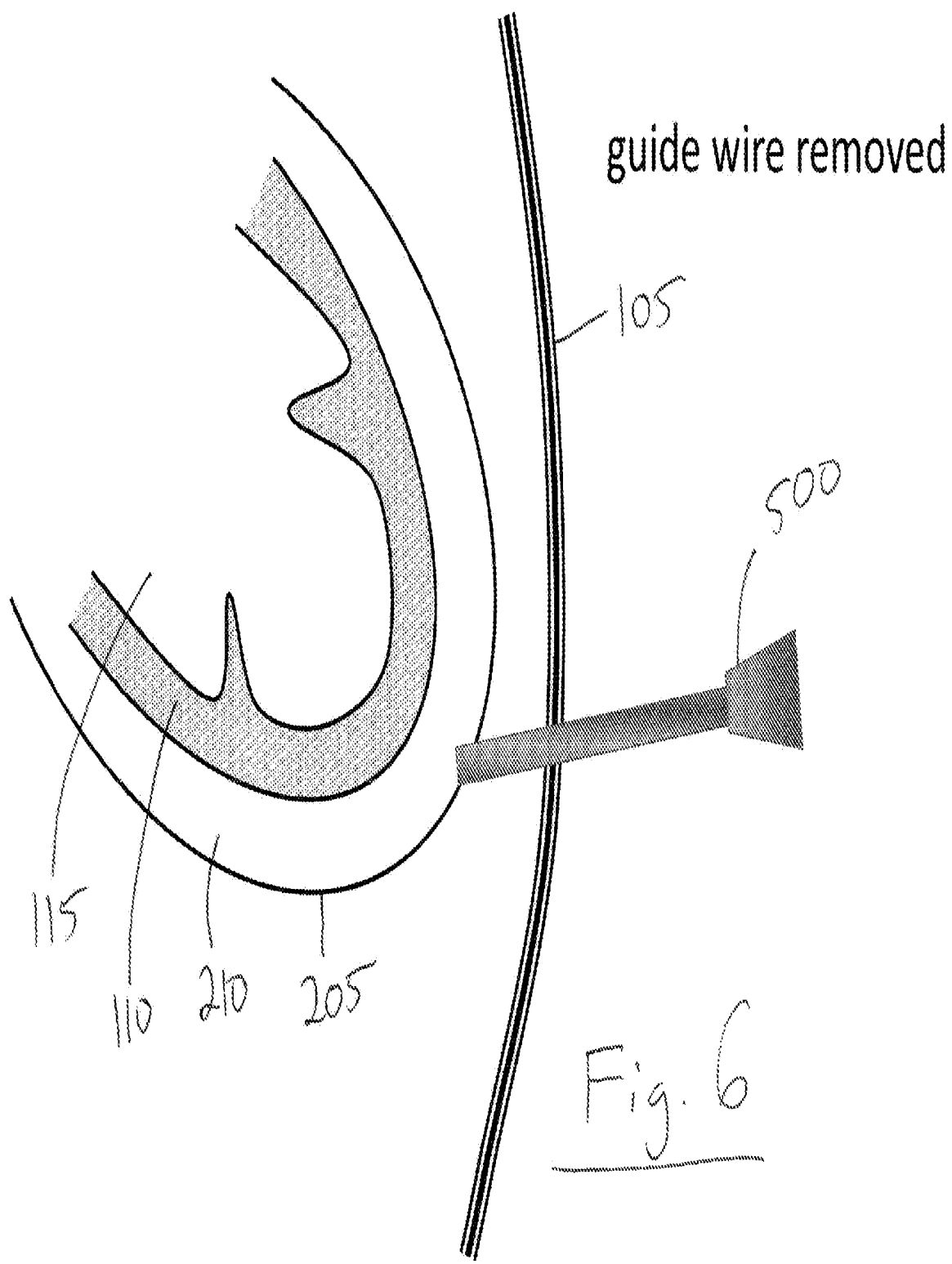

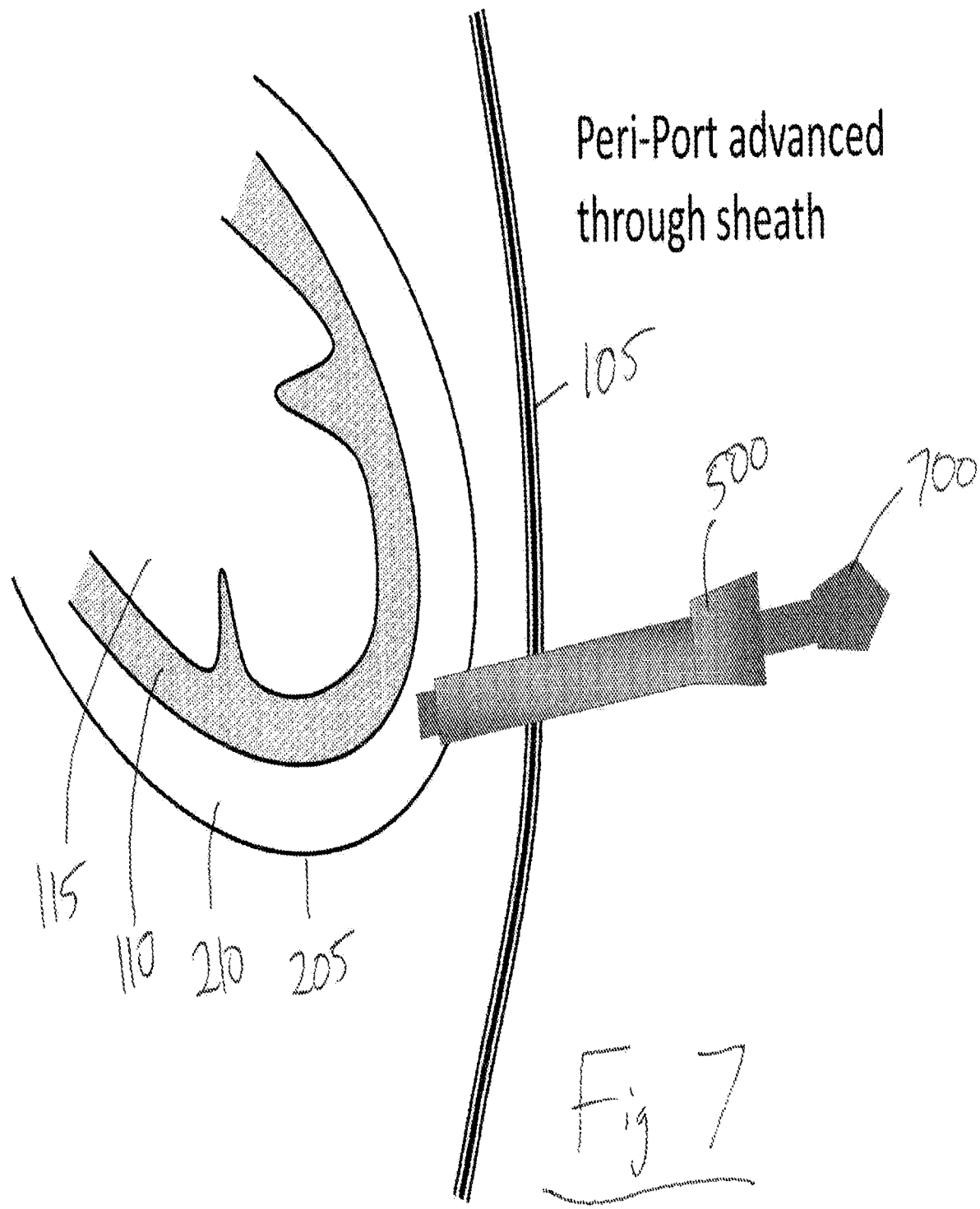

PeriPort Transducer

En face view

Side view

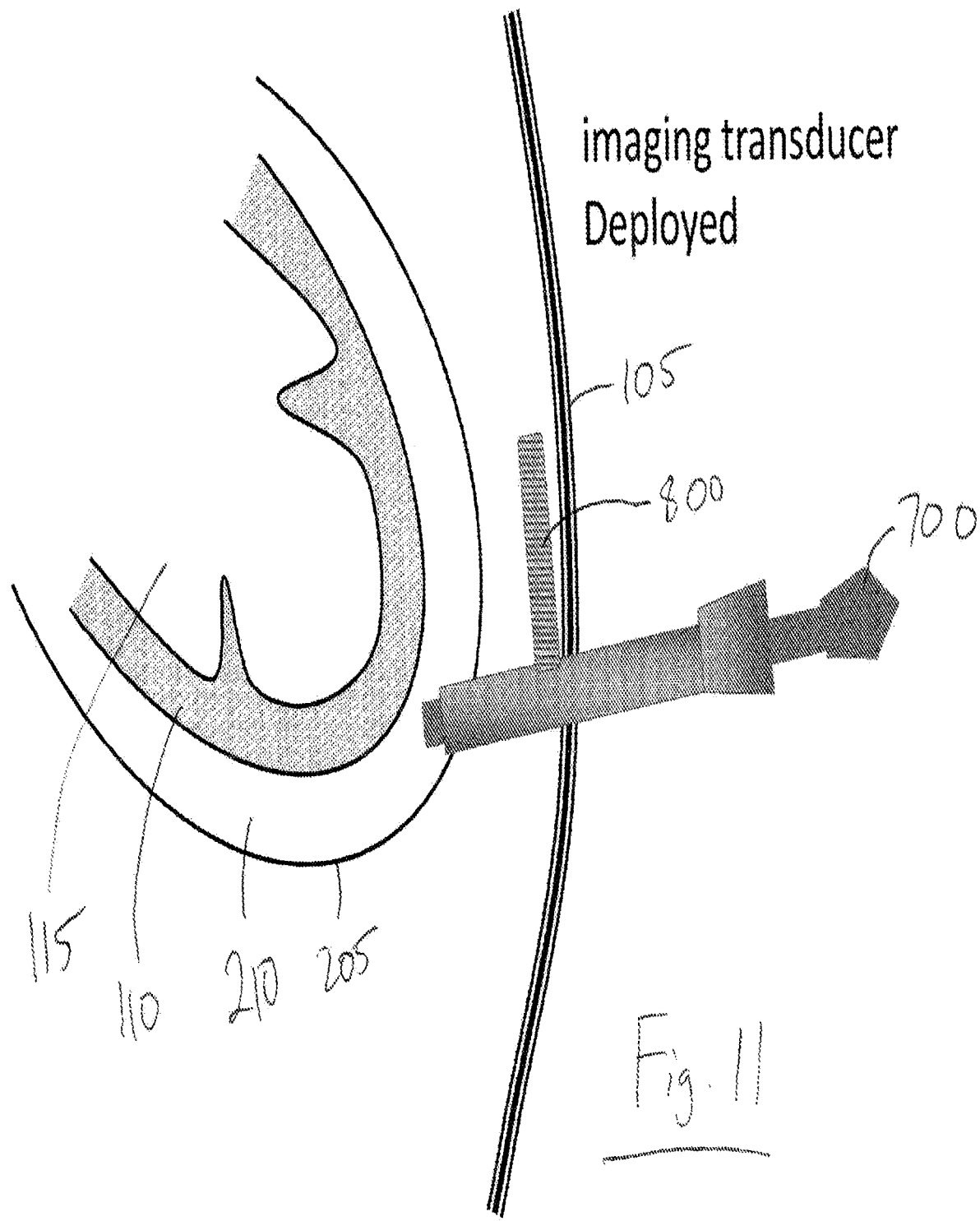

MyoPoint needle is straightened by manipulation of PeriPort tip

Alternative filter mechanism – front hood

Filter delivery catheter has a front hood where the collapsed filter resides during transfer to optimal location. Once there, a portion of the delivery catheter is retracted to open the filter

Closure device proximal pad Deployed by further withdrawal of delivery catheter

Proximal pad pushed up against myocardium using the delivery catheter

Retaining tubes removed – ends of the harness wires are coiled like pigtails and hold the proximal pad against the myocardium

Repair mechanisms

Elastic band mounted on a cylindrical inner strut. Mitral chord or valve tissue is sucked into the strut prior to deploying the band.

cylindrical strut

Outside deploying strut that pushes band onto structure trapped in strut

Commissural stitch to reduce valve opening and reduce regurgitation

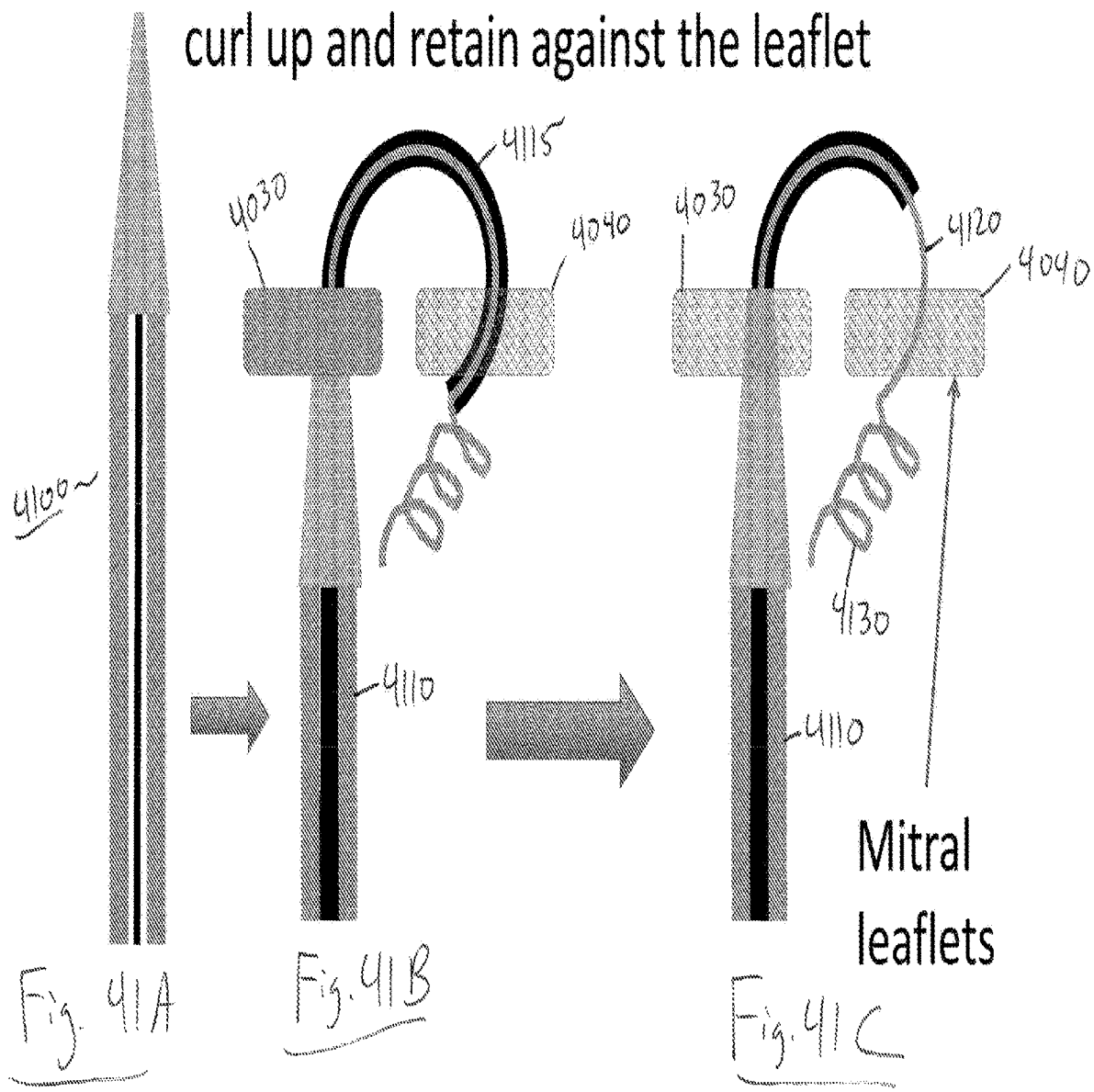

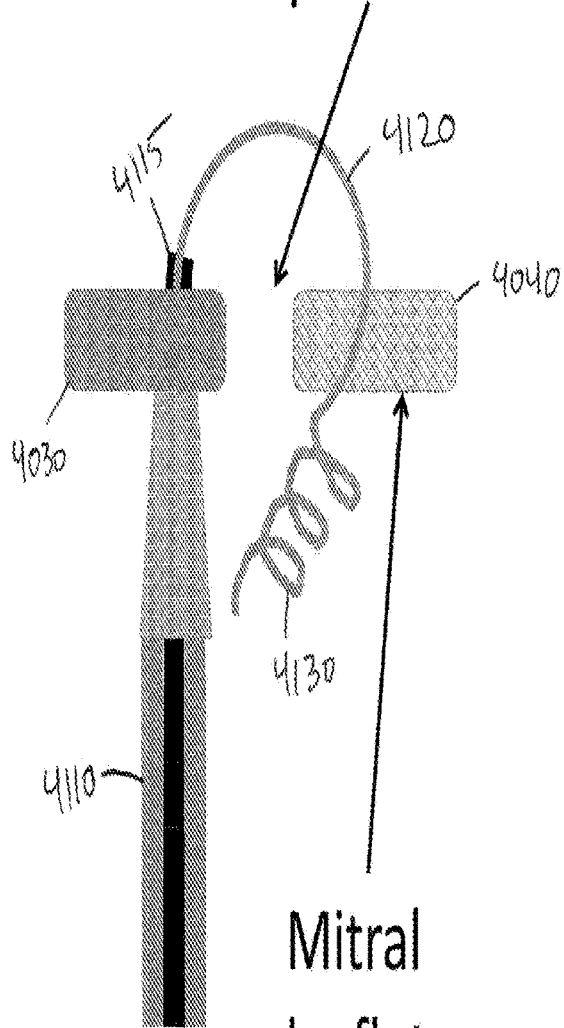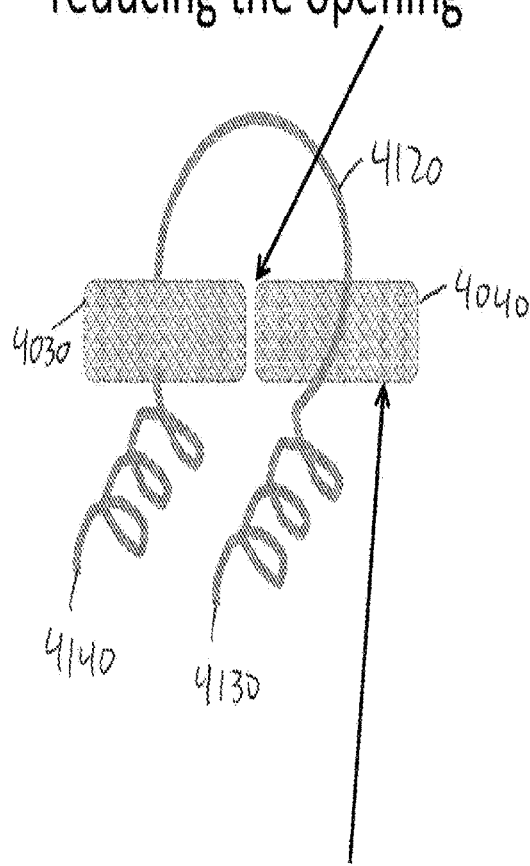
Fig. 41D
Fig. 41E

After adequate leaflet mass is suctioned – a loop or a band are applied – single or multiple locations; after band is applied, leaflet is less redundant and more competent Band applied to redundant portion redundant portion now excluded by band

DEVICES AND METHODS FOR IMAGE-GUIDED PERCUTANEOUS CARDIAC VALVE IMPLANTATION AND REPAIR

This application is a continuation of U.S. patent application Ser. No. 16/016,205, filed Jun. 22, 2018, which claims the right of priority to U.S. Patent Application 62/527,905 filed Jun. 30 2017 by the same inventor.

TECHNICAL FIELD

The invention, relates to the field of cardiac valve replacement and repair and, in particular, to a plurality of devices and a sequential method for implanting via ultrasound and other image guidance a percutaneous cardiac valve, for example, the aortic valve between the left ventricle outflow tract and the ascending aorta or the mitral valve.

BACKGROUND OF THE INVENTION

There is an increasing focus on the percutaneous treatment of valve disease/Mitral valve disease is very common. Rheumatic mitral valve disease is estimated to affect close to 16 million individuals worldwide. [See WHO Tech Series #924, 20041 with about 300,000 new cases per year and surgery indicated in approximately one million patients per year. Mitral regurgitation is common, affecting more than approximately four million Americans—nearly one in ten people aged seventy-live and older. [See https://www.dicardiology.com. Aortic valve disease is also common and its prevalence increases with age. For people over the age of seventy-five years, the prevalence of aortic stenosis is 3%, More than one in. eight people over the age of seventy-five have moderate or severe valve disease. As the population ages, this condition becomes an important public health problem. [See Nkomo V T, Gardin J M, Skelton T N, et al. Burden of valvular heart diseases: a population-based study. Lancet 2006:368:1005-11.]

There are no good medical therapies for valve disease hence in moderate to severe valve disease with, symptoms, the definitive treatment is valve repair or replacement. There has been a paradigm shift in treatment of valve disease with the introduction of transcatheter valve repair and replacement (collectively referred to as structural heart devices). This .field is growing exponentially and the global structural heart device market is expected to hit $9.7 billion by 2022 and predicted to grow at a CAGR of 14.3% between now and 2022. Of this, aortic valve replacement occupies the largest share and greatest growth potential with the transcatheter aortic valve replacement and implantation (TAVR. and TAVI) market valued at $5.9 billion by 2022. Allied Market Research (AMR) expects the market to grow at a compound annual growth rate (CAGR) of 16.5 percent from 2016 to 2020. The key drivers for market growth are increasing demand for minimally invasive surgery, focus on reducing healthcare costs, and a burgeoning aging population with valve disease. Additionally, the burden of valve disease in the developing world remains high. [See http://www.cardiovascularbusiness.com].

The transcatheter approach is 'almost exclusively performed via femoral arterial, access. Apical approaches are also performed but are minimally invasive surgical procedures rather than purely' catheter based. More recently, mitral valve replacement is being performed using a trans-atrial approach. Similar, transcatheter solutions are being explored for the pulmonic and tricuspid valves.

Consequently, there is a great need in the art for a minimally invasive method and apparatus for, for example, image-guided percutaneous cardiac valve implantation and repair.

SUMMARY OF THE INVENTION

A trans-femoral approach to cardiac valve replacement and repair has been very successful, but the primary concern has been a high incidence rate of stroke. Strokes are thought to occur due to scraping off arterial plaque while advancing the catheter into the aorta from the femoral artery in a recent publication, "Cerebral Embolic Protection During Transcatheter Aortic Valve Replacement," Journal of the American College of Cardiology, November, 2016, despite deploying stroke prevention filters, stroke rates did not decrease substantially. The femoral approach also makes mitral valve intervention challenging since the operator may perform a transeptal puncture and orient the catheter tip and device, almost perpendicular to the location-of the mitral valve. Given the sharp turn needed to access the vicinity of the mitral valve, this alignment is difficult and may need several attempts.

A trans-apical approach according to the present invention will avoid those issues and these of prior art techniques and apparatus but may require mini-surgery that is minimally invasive, but on the other hand, requires considerable operating room time, Both femoral and apical or atrial approaches may use separate intra-procedure ultrasound (or other) imaging, A trans-apical system that does not need surgery, prevents strokes and provides built-in imaging, and intra-procedure monitoring will allow safe and reliable deployment of cardiac valves and significantly expand the use of these transcatheter valves.

The proposed invention comprises a multi-component/multi-device platform that will provide a single, integrated platform for delivery of valves (of any known type, biologic or artificial) or other devices into the heart with real-time ultrasound and other Image guidance via prosthesis delivery to the region of the defective valve, in an Image-guided catheter such as represented by if U.S. Pat. No. 9,149,257 entitled "Image Guided Catheters and Methods of Use" issued Oct. 6, 2015 (the '257 patent) by the same inventor, per FIG. 3A, an. ultrasound beam generated by a transducer element 210 of an ultrasound imaging channel 214 provides a cone-shaped imaging zone 301 which can display a needle or guide wire or sheath or other tool extending from the distal (patient) end or provide device delivery and be directed parallel to the ultrasound beam and may be located within a sheath or lumen or plurality of lumens. (The '257 patent should be deemed to be incorporated by reference as to its entire contents). On the other hand, the needle 208, a guide wire, sheath, delivery system for a Filter or a prosthesis or tool being deployed parallel to the cone-shaped ultrasonic beam imaging zone 301, may be difficult to see in the imaging zone 301 because the needle, guide wire, sheath or lumen is very thin in diameter, may comprise a smooth surface, and may extend in the same direction as the ultrasound beam is projected (parallel to the sonic beam) from the thin, minimally invasive image-guided catheter limiting the amount of desired ultrasound echo. This can be improved by providing echogenicity by sanding, engraving or otherwise causing ultrasound beams to be reflected back to the source so that the sonic beam will tend to follow the angles of impingement and reflection and are intended to project from the needle, sheath or tool in a direction deeper into, for example, as a human body in which the image guided catheter of FIG. 3A is inserted and so may be captured by surface-mounted or implanted ultrasound transducers. The image guided catheter may be inserted by directing an introducer needle through the skin surface and guides the image guided catheter under ultrasound vision to a site of interest Ultrasound waves may be echoed or returned to the ultrasound transducer source or scattered toward the human body surface. Also, it is desirable to visualize the needle, sheath or tool Itself (via echogenicity) to determine the direction of its movement within the human body from the point of entry of the human body to an area of interest such as the human heart in one embodiment, the needle or sheath may be hollow (in another, solid) and may be removed or moved forward via a lumen extending the length of the catheter once the catheter is located at a site of interest and may be replaced in real time with a guide wire or tool such as a micromechanical motor system (MEMS), in another embodiment, the tool may be used simultaneously (in its own lumen) with the needle or sheath to bend or guide the needle, guide wire or sheath to the region of interest from a patient's skin surface.

The following additional U. S. patents and published applications of Dr. Theodore Abraham should be deemed to be incorporated by reference as to their entire subject matter and refer to similar image guided catheters, implanted ultrasound devices, wired or wireless ultrasound devices and the like which may receive signals from echogenic needles, sheaths or tools and surrounding human tissue or blood or other fluids of interest at a site of interest for a minimally invasive surgical procedure: U.S. Pat. No. 8,038,622 issued Oct. 18, 2011; U.S. Pat. Nos. 8,147,413 and 8,147,414, issued Apr. 13, 2012; U.S. Pat. Nos. 8,403,853 and 8,403, 859 issued Mar. 26, 2013, and U.S. 2016/008,1658 published Mar. 24, 2016, Most recently, U.S. Ser. No. 15/636, 328 entitled "Image Guided Catheters and Methods of Use" was filed by the present inventor on Jun. 28, 2017 and U. S. Provisional Patent Application Ser. No. 62/526,170 entitled "Echogenic Needle. Sheath or Tool" was filed by the present inventor also on Jun. 28, 2017.

The components of an apparatus and method for cardiac valve replacement comprise: a Vu-Path ultrasound imaging catheter which is a similar device to that described in prior patents of the inventor. There is also a 'Vu Path stabilization system for stabilizing the imaging guided catheter and any other components requiring stabilization to be sutured or otherwise stabilized with respect to an entry point through skin surface tissue: into a patient body, typically, through the human chest wall, for example, to the heart. A further component of the present invention is a myocardial entry system. The myocardial system, is intended to enter the myocardium at an angle to facilitate closure of the heart at the ventricular apex under ultrasound vision. If not inserted at an angle, closure of the myocardium due to blood pressure will be difficult. So a closure device comprising a pair of umbrella-like devices are used to close the opening at the ventricular apex. An initial incision is made of less than a centimeter, on the order of five to seven millimeters, in the chest wall proximate the heart. The introducer needle points under ultrasound guidance and the surgeon chooses a point of entry at an angle through the pericardium into the pericardial, space. From a distal tip of a Peri Path pericardial image guided catheter, as described herein, a guide wire is deployed into the pericardial space, under vision. The PeriPath may then be removed and replaced with, a sheath that may be advanced through the chest wall via the .remaining guide wire and enter the pericardial space under ultrasound vision: guidance.

Once the pericardial space has been penetrated via the sheath, the guide wire may be removed leaving the sheath displaced at an angle (a sharp angle less than ninety degrees) and entering the pericardial space. The operating space between the outer and inner pericardial linings may be expanded by injecting saline or other solution to create an operating space volume using a hollow needle moved through the sheath, Through the sheath and with ultrasound guidance, a periport (pericardial space portal) now comprising an assembly of a particulate aortic filter (undeployed) followed by a prosthesis comprising a replacement heart valve may be deployed via first and second tubular pushers surrounding a guide wire. To provide ultrasound guidance, an imaging transducer may be moved from a lengthwise position along the periport to a position that is angled, for example, at an angle less than orthogonal with the periport to place the ultrasound imager at a location with a directed imaging zone that captures the heart and subsequent, use of the periport. The ultrasound imager should have sufficient depth to reach within the heart and have sufficient resolution to view heart parts especially the heart valve to be replaced and beyond the valve to where a filter such as an ascending aortic filter may be utilized to prevent stroke demonstrated as problematic in the prior art.

To achieve the goals of depth of ultrasound vision, the ultrasound transducer may be calibrated within a range of twenty-five kHz to 100 MHz and, more, particularly, operate in a range between one and ten MHz. As taught in prior patent applications of the inventor, the image guided catheter may comprise a plurality of imaging lumens in which transducers, sheaths, guide wires, delivery systems and tools may be replaced in real time within a particular lumen under vision. in addition, as discussed above, it is important to prevent leaks from the pressure zone of the heart ventricle by inserting the periport device at an angle once in the pericardial space (which may be opened with saline solution (as discussed above) and its tip bent to point to the ventricular space at an angle at its apex to prevent leakage. Through the bent periport located just outside the ventricular apex, a needle may be introduced so as to puncture the ventricular apex of the heart at a sharp angle to minimize flow of blood from the ventricle into the pericardial space and then the periport may be straightened for continuing the procedure. Then, the periport is advanced through the left Ventricle apex using the needle as a guide wire and at an angle to prevent blood loss. The periport is deployed (moved) into the ventricular space. The needle may then, having served its purpose, be removed by retraction through the periport and out the chest wall.

in place of the needle there is now inserted via the periport a telescoping, multi-channel pericath which in cross-wise view comprises at its center, a guide wire such as a J-tipped guide wire, an aortic filter delivery system including at least one aortic filter (for capturing particulate matter such as plaque), a prosthetic valve which will be contained within a pericath outer cylinder delivery system attached to another delivery system tube just outside the filter tube. First, the J-tipped guide wire (with, the J straightened) is fed through the existing, for example, aortic valve to be replaced. The J tip is automatically bent to form a curve so as not to inadvertently damage the wall of the ascending aorta. Then, the aortic filter, m a collapsed, cylindrical form, is deployed over the guide wire by advancement by pushing with a coated, slideable cylindrical solid pushing tube. The collapsed aortic filter (or filters) may be moved through the existing valve to a position toward the end of the guide wire under vision, and the soft i-tip deployed automatically as discussed above. Once the aortic filter is positioned, it is opened (like an umbrella) to block the aortic passage for filtering and collect any particulate matter such as plaque under image guidance of a peripoint device (with similar ultrasound frequency range and sufficient depth of vision and resolution).

Now the prosthesis containing a new heart valve, an artificial valve or one from a mammal (such as a FIG.) may be deployed using a similar coated pushing tube surrounding the filter tube. Under ultrasound guidance, the prosthesis is positioned at the location of the defective valve. The defective valve is pushed aside by the prosthesis to form part of the heart wall and so replaced by the prosthesis heart valve as the—prosthesis is deployed to fill the entire space taken by the defective valve (for example, using deformation or fluid to expand a balloon shape. The prosthesis may comprise a source of pressure (such as a balloon) which may be opened to completely fill the space where the defective valve has now become part of the ventricular aortic wall or a MEMS may be used to change its shape to fit the aorta cavity and press the defective valve against the walls.

Once the prosthesis and replacement valve are in place and positioned to Ell the entire space taken by the defective valve, ultrasound may be used to look for leakage of blood around the prosthetic valve and the valve expanded in size, like a balloon, or change shape from an elongated cylinder to a fat, short cylinder to fill the space entirely that was left by the defective, pushed aside valve. Once the new valve is placed, the aortic filter is collapsed like an umbrella for removal capturing any particulate matter inside, and may be removed by the plastic tube or pusher that now becomes a puller. When pulling the collapsed filter out of the heart, the J-tip collapses, is automatically straightened and so the collapsed filter (like a collapsed umbrella) is easily pulled out through the prosthetic valve along with the, for example, J-tipped guide wire.

The heart valve prosthesis is now capable of functioning normally replacing the defective valve. Remaining still, at the ventricular apex is the periport which is now used for delivery' of a closure device comprising two umbrella-like pads, a distal pad and a proximal pad for closing the myocardium, for example, at the ventricular apex. The closure device then comprises a distal pad a proximal pad and wires used for installation, control of opening and closing and, in particular, closing the angled hole remaining at the ventricular apex of the myocardium, The distal pad is pushed through the myocardial opening, opened and then pulled to a position closing about the myocardial angled opening. Then, the proximal pad is opened and is pushed upward until it reaches the myocardium under ultrasound vision. The two reverse, open "umbrella" pads, the distal and proximate pads, effectively close the angled myocardium entry point so as to preclude any release of blood through the ventricular apex.

When the insulation is pulled off the two installation wires for the distal and proximal umbrella pads, the wires automatically coil like pigtails, and the pigtails hold the proximal pad against the myocardium and the distal pad to form a permanent stopper for the leakage of blood. The coating of the wires is removed through the periport, which is the only component remaining in the vicinity of the ventricular apex. All that is left to do then is to deflate the pericardial lining by removal of excess fluid (for example, through use of a syringe of a lumen and remove the periport from the pericardial wall having been freed of any suturing for stabilization, and the small incision area of the chest wall may be closed.

in further embodiments, a mitral valve may be repaired or replaced and mitral valve repair will be described to include simultaneous deployment of an aortic filter, but first aortic valve replacement apparatus will be discussed in accordance with the following brief description of the drawings and the detailed description of the invention and its components which follows.

BRIEF DESCRIPTION OF THE DRAWINGS

FIG. 4 shows removal of the peripath device leaving the guide wire behind within the pericardial space.

FIG. 5 shows the introduction of a sheath having ultrasound vision and advanced over the guide wire to the opening of the pericardium and penetrating the outer pericardium lining.

FIG. 6 shows the removal, of the guide wire, 'leaving the sheath equipped with ultrasound vision behind penetrating both the chest wall and the pericardium to reach the pericardium space.

FIG. 7 shows the sheath 500 being an elongate cylinder for receiving a periport that is pushed through the sheath into the pericardium space.

FIG. 8A comprises an en face view showing a deployable linear transducer array. FIG. SB shows a side view where the deployable linear transducer array is depicted at one side of the periport having twisted by the surgeon and moved to desired viewing position.

FIG. 11 shows the periport with the linear transducer array deployed, between the chest wall and the pericardium and twisted into a position where it may provide vision of the pericardium space, left ventricular apex and the left ventricle (and beyond).

FIG. 24A provides exemplary aortic filter structural detail—closed in dwelling position; architecture and mechanism similar to operation of an umbrella, The distal end comprises an umbrella filter followed by a screw mechanism and an external manipulator is used to open and close the umbrella. For example, clockwise rotation may open the umbrella filter into a deployed position in the ascending aorta (by moving umbrella-like spokes (not shown) and counter-clockwise rotation may close the umbrella filter capturing any particulate material for removal via the catheter delivery system.

FIG. 24B provides a detailed side cut-away view of the umbrella aortic filter comprising support spokes like an umbrella for opening and deploying the aortic filter or collapsing the filter, the spokes being opened and closed by the twisting represented by FIG. 24A.

FIG. 24C shows a typical umbrella filter retraction of the delivery system to open the aortic filter via the spokes of FIG. 24B. The arrow points in the direction, of the delivery tube in. opening the aortic filter, FIG. 24D shows pushing back to fold the spokes and collapse the aortic filter, the arrow again showing the direction of the delivery tube to collapse the filter.

The following figures will demonstrate closure of the myocardial angular opening via a closure device introduced through the periport.

Figure 27:
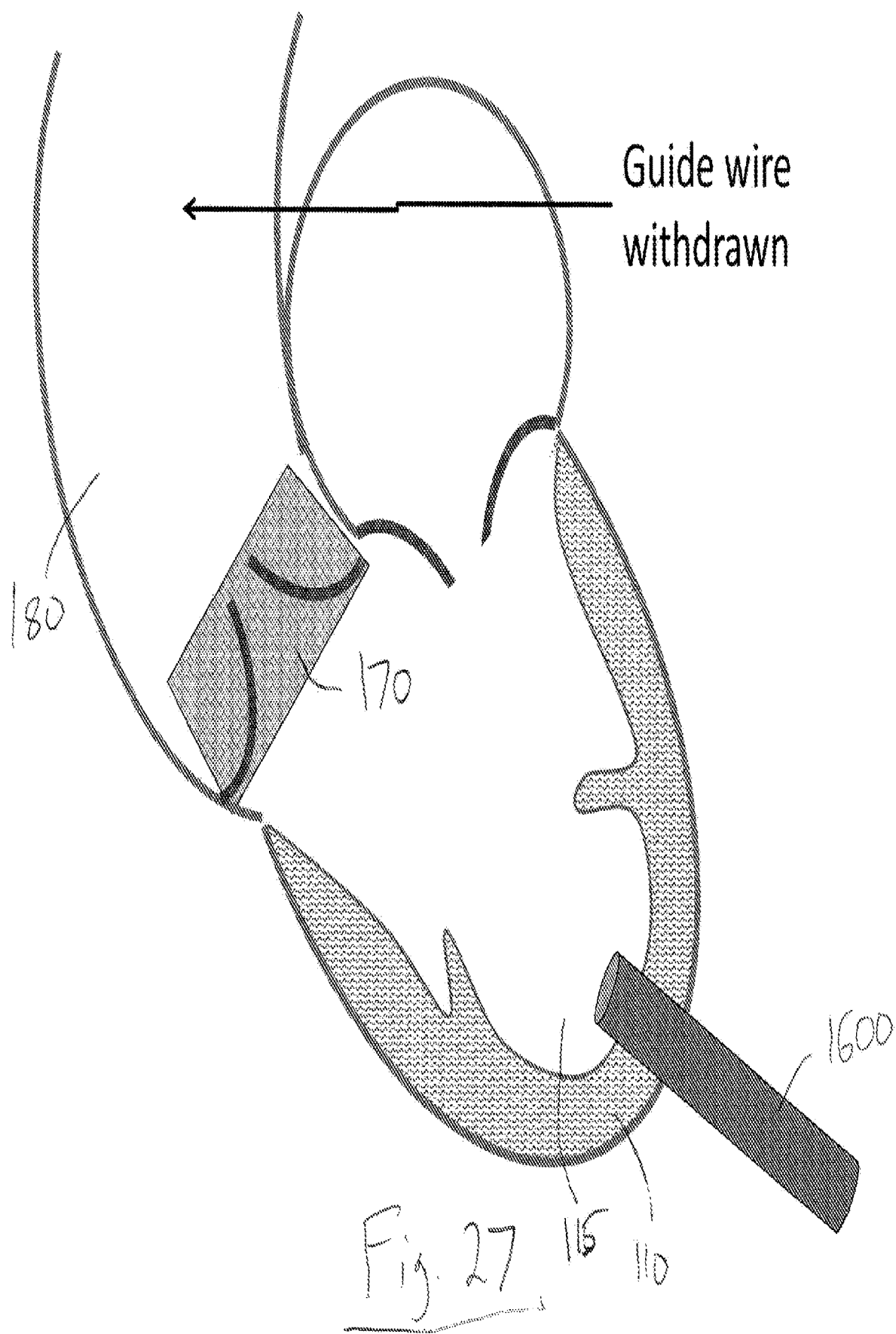
FIG. 27 shows the further removal or withdrawal of the guide wire (all delivery catheter tubes also having been removed) leaving the prosthesis new replacement heart valve in place and the periport still protruding into the left ventricular space at an angle at the ventricular apex.
Figure 28:
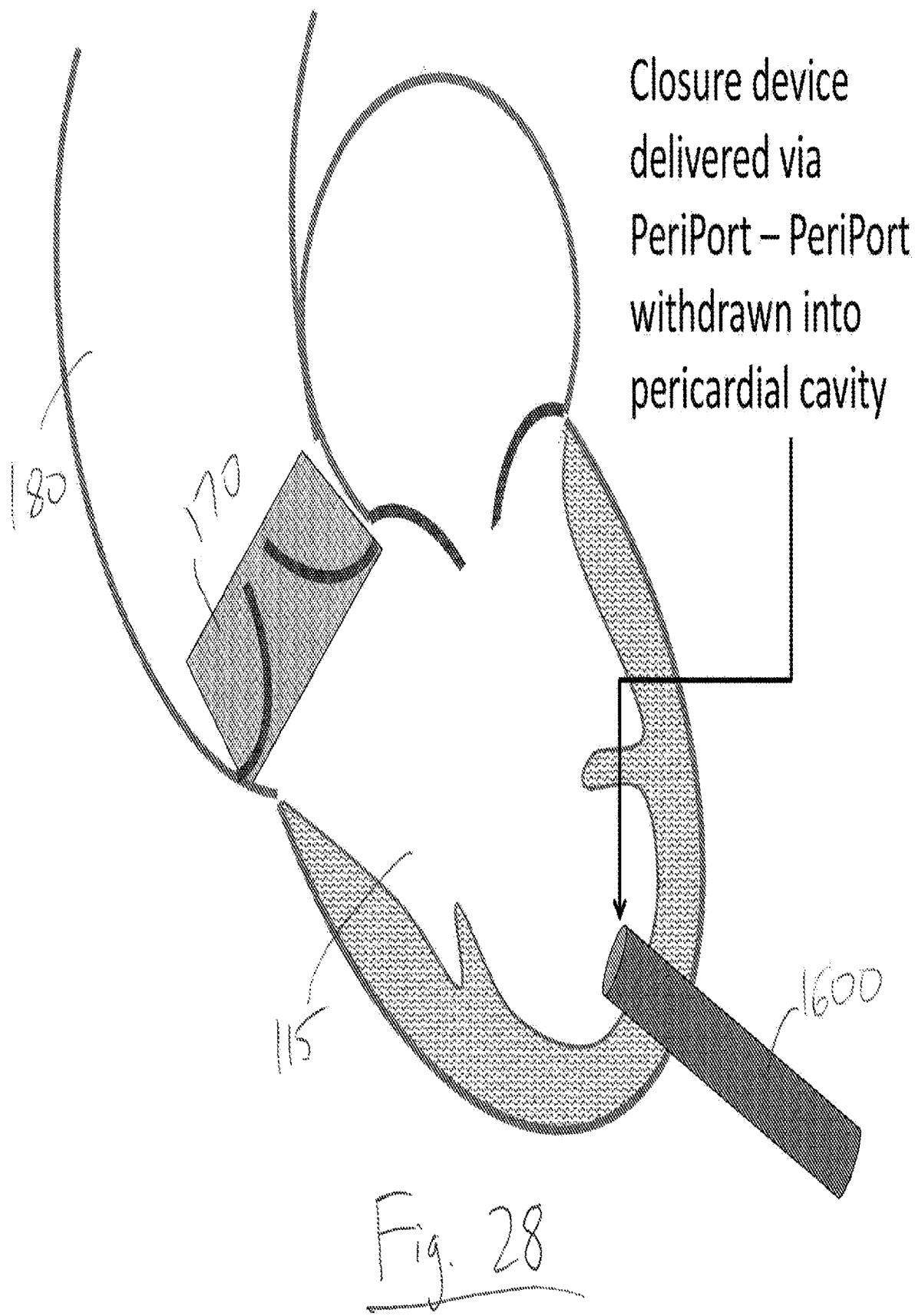
Figure 29A:
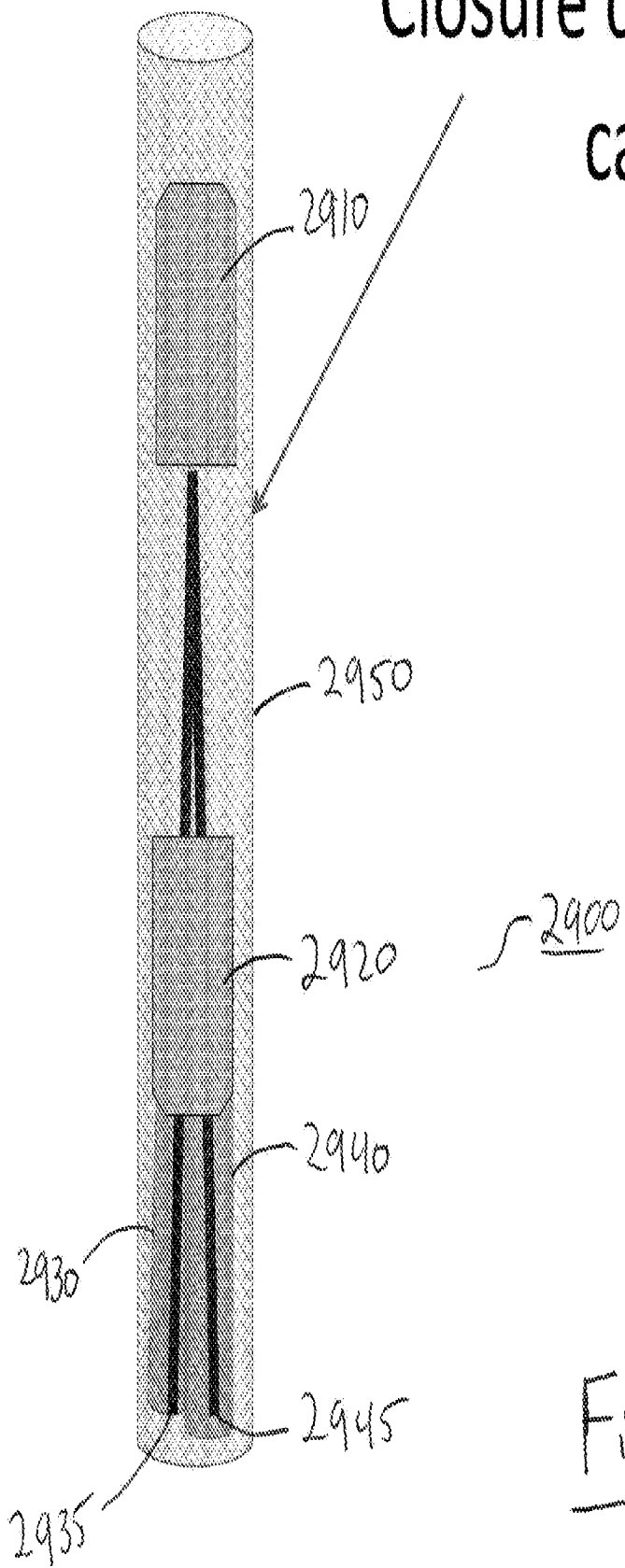

FIG. 28 shows a similar figure to FIG. 27 with a closure device contained within tile periport for delivery via the distal (patient) end under image guidance. The periport is now withdrawn, to merely serve as a plug to prevent leakage of hood via the myocardium, FIG. 29A shows an exemplary closure device arrangement comprising a distal pad and a proximal pad that may be deployed via the periport of FIG. 28, Two spokes or catheter tubes are used under vision to move the distal and proximal pads into place at the myocardium as will be described by the following figures.

Figure 29B:
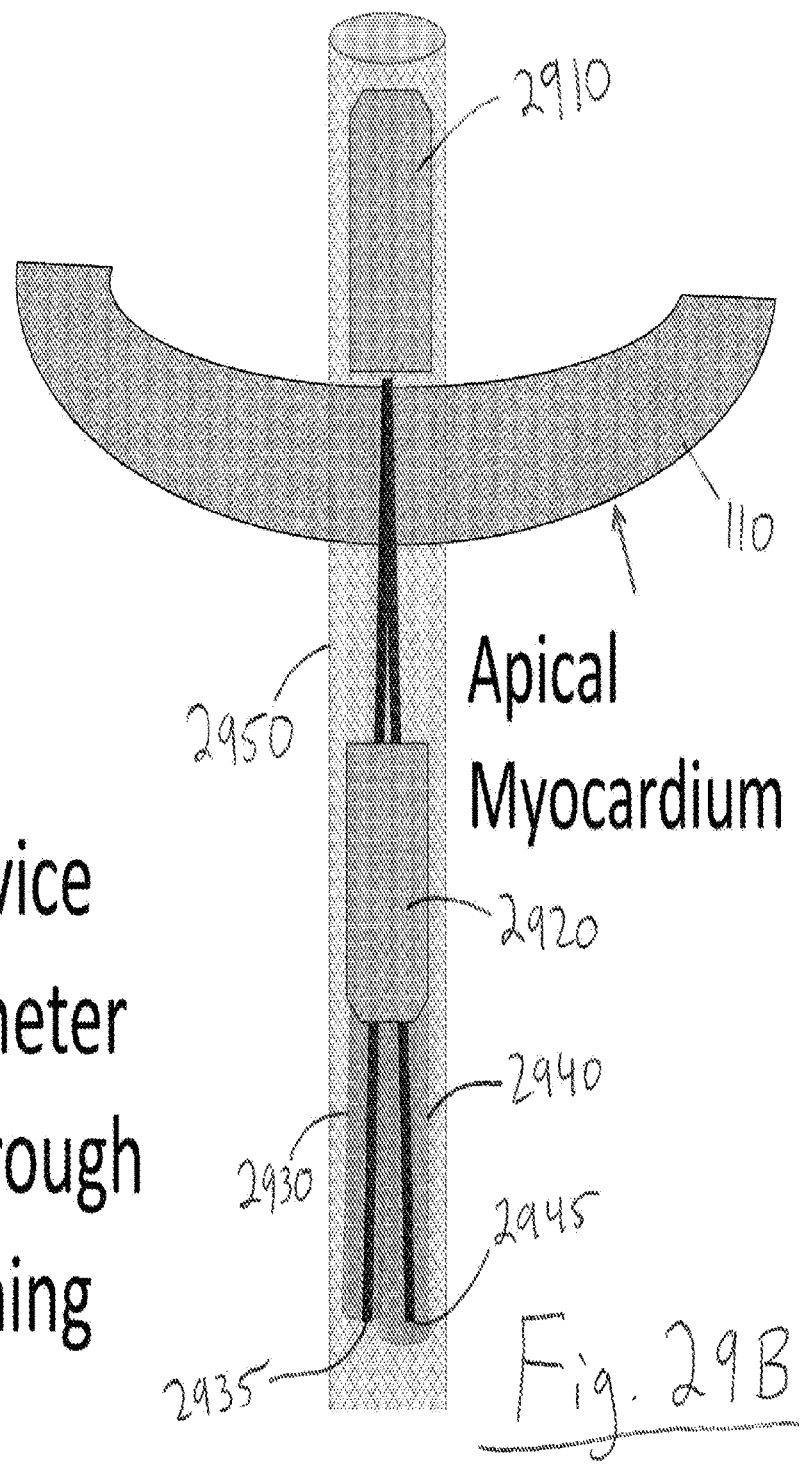

FIG. 29B shows use of the periport to deliver the closure device through the myocardial wall of the left ventricular apex (apical myocardium shown with the periport still puncturing the myocardium and plugging the hole at the left ventricular apex.

Figure 30:
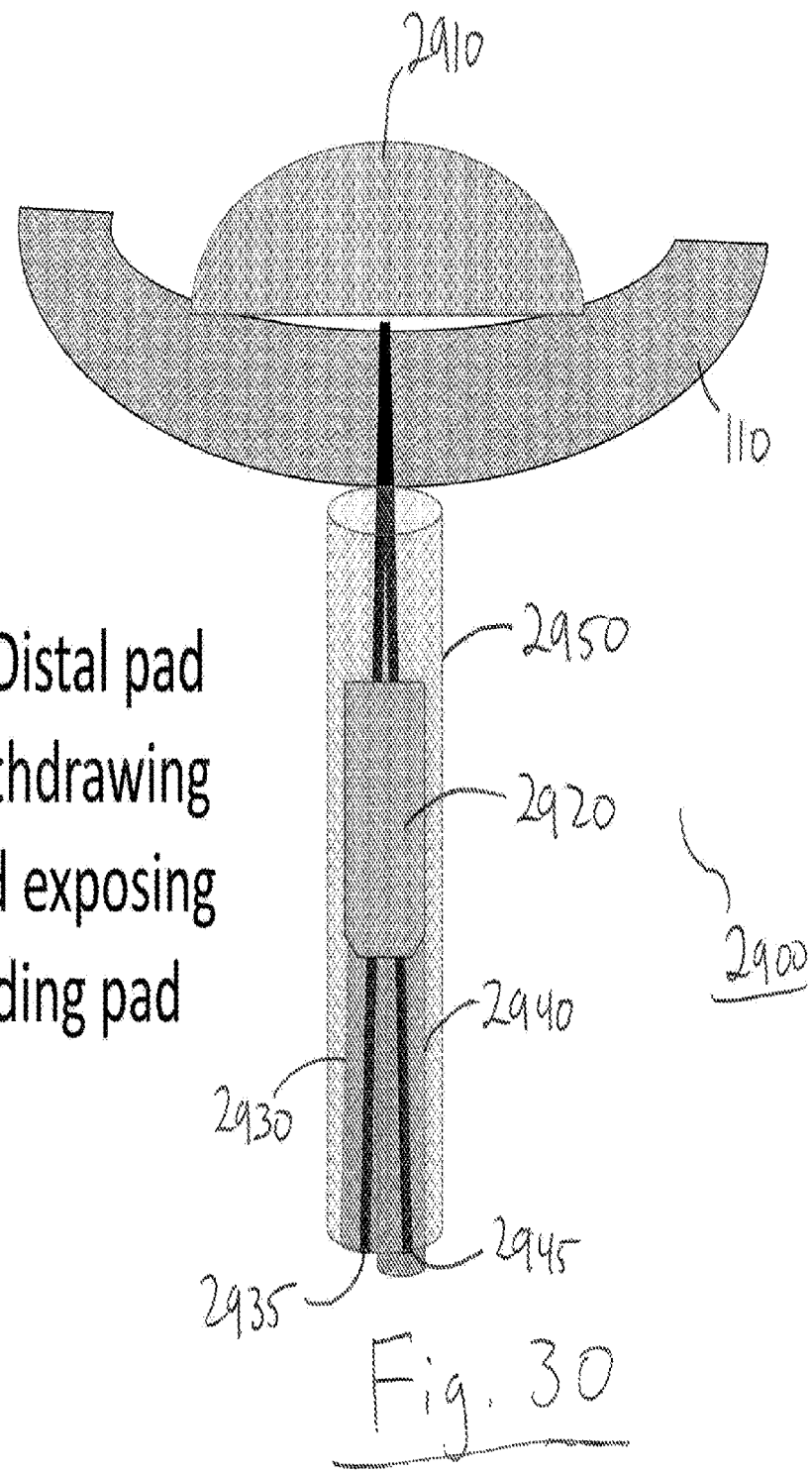

FIG. 30 shows first the withdrawal of the periport into the pericardial space and simultaneous deployment of the distal pad and its deployment and being pulled to an open, position plugging the hole. As of this time, the proximate pad has not yet been deployed. As with the aortic filter, the distal pad may be opened like an umbrella and will prevent any blood leakage into the pericardial space. The closure device distal pad is deployed by withdrawing the catheter (periport) and exposing the self-expanding distal pad to open automatically.

Figure 31:
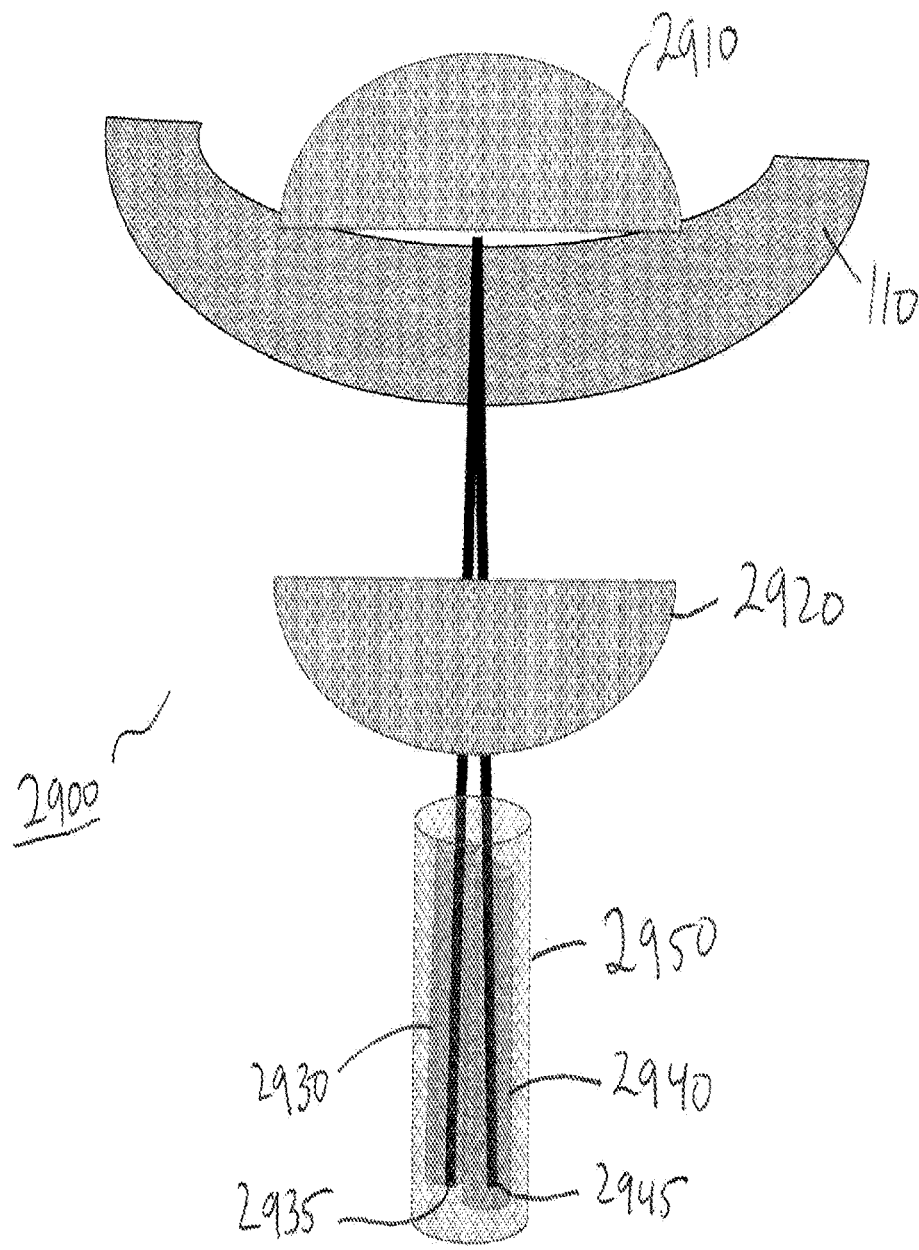

FIG. 31 shows further movement of the periport with respect to the proximal pad and simultaneous opening of the proximate pad. The closure device proximal pad is deployed by the further withdrawal of the delivery catheter (periport) but is not yet positioned (pushed) toward the myocardium.

Figure 32:
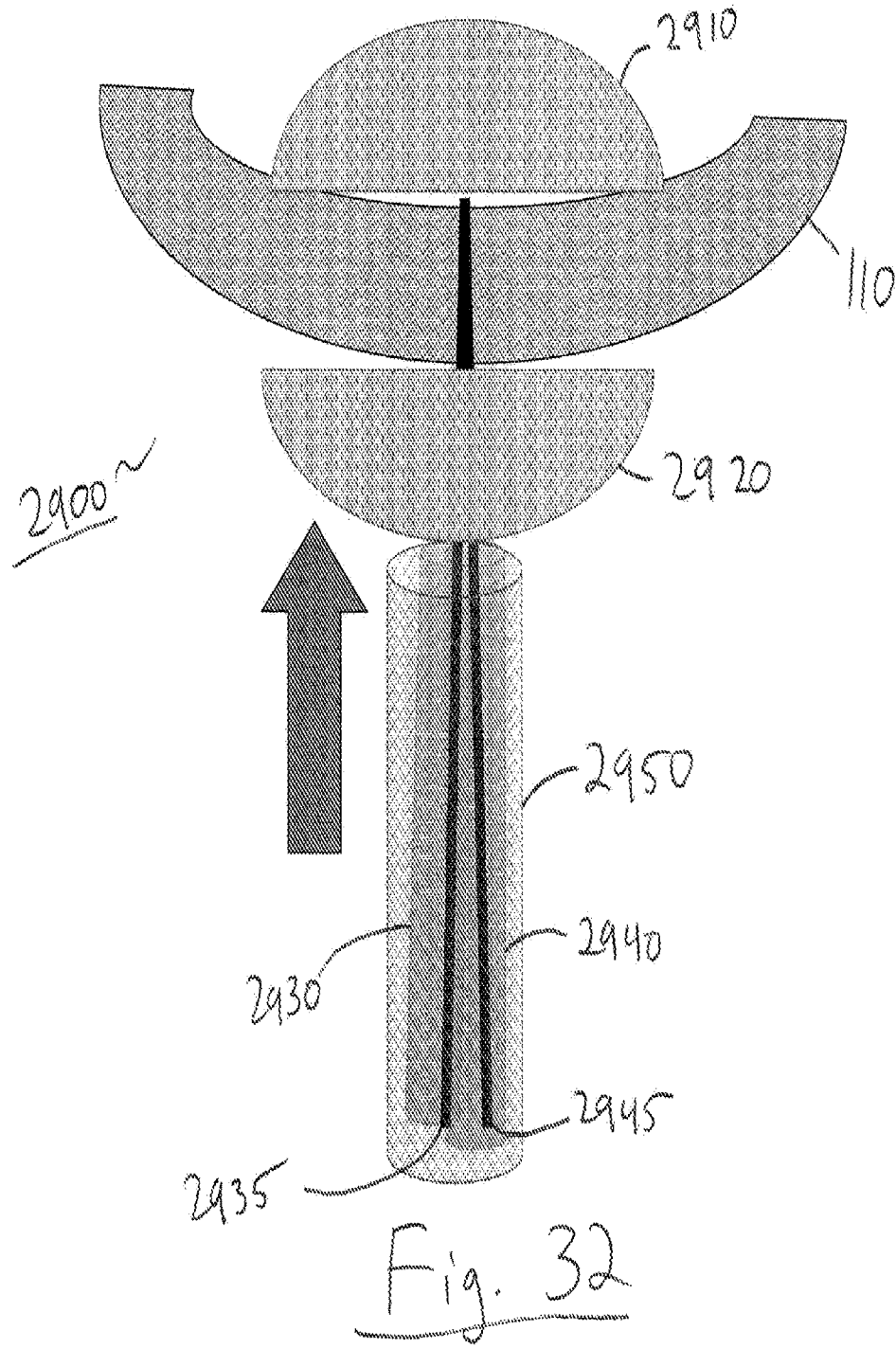
Figure 33:
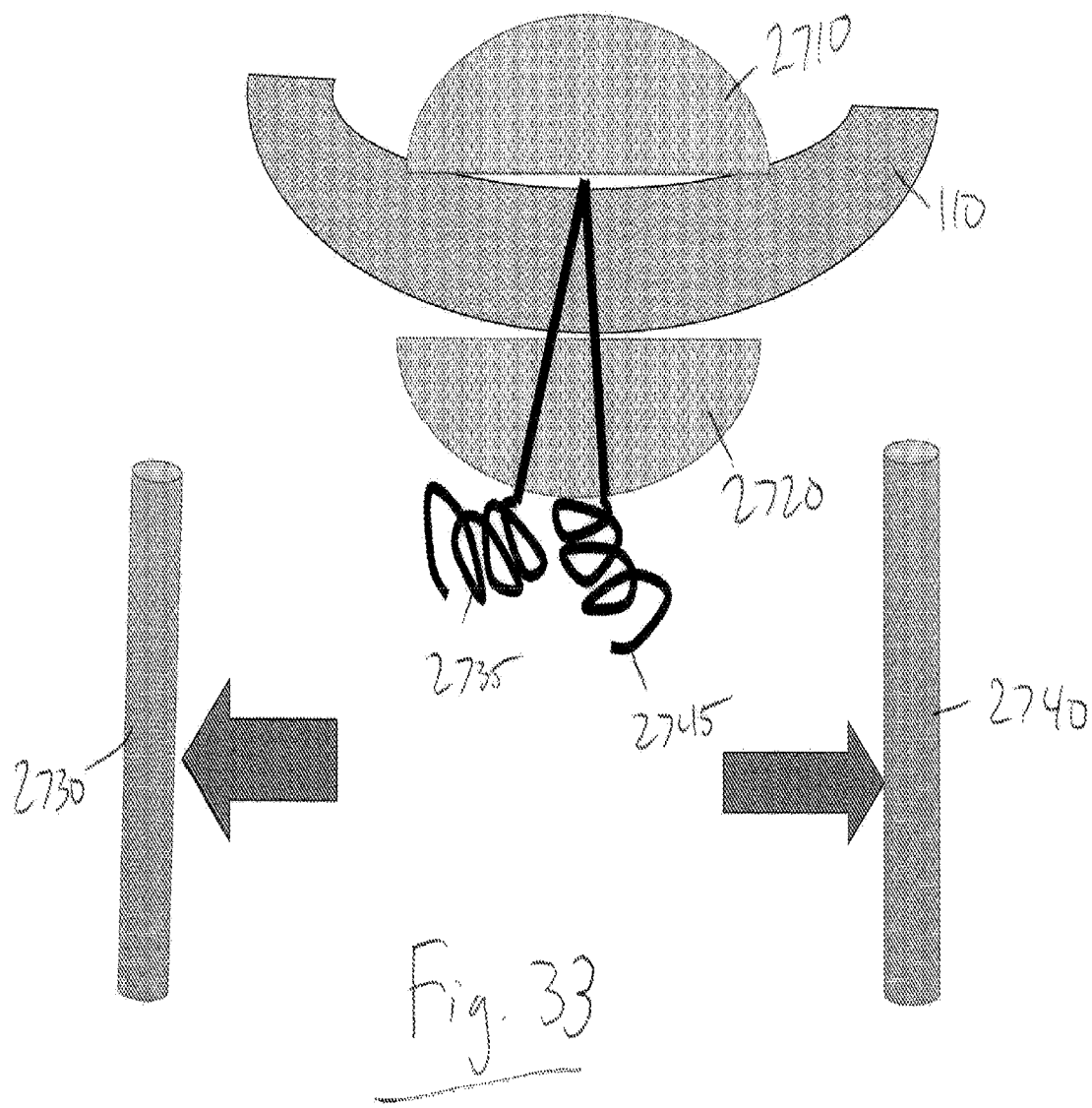

FIG. 32 now shows use of the closure device within the periport to push, the proximal device up against the myocardium using the delivery catheter (periport) to provide the pushing. The leads still remain and can be used to help pull the distal pad against the pushed proximal pad via respective catheter tubes from the peripad, FIG. 33 shows removal of the distal pad and proximal pad retaining, tubes (like insulation on a. wire), the ends of the harness wires automatically coil as the tubes are removed like pigtails and serve to hold tight the distal pad to the proximal pad with the apical myocardium in between and close off any flow of blood due to blood pressure in the left ventricle. The tubes are shown removed from the wires which-automatically pigtail.

Figure 34:
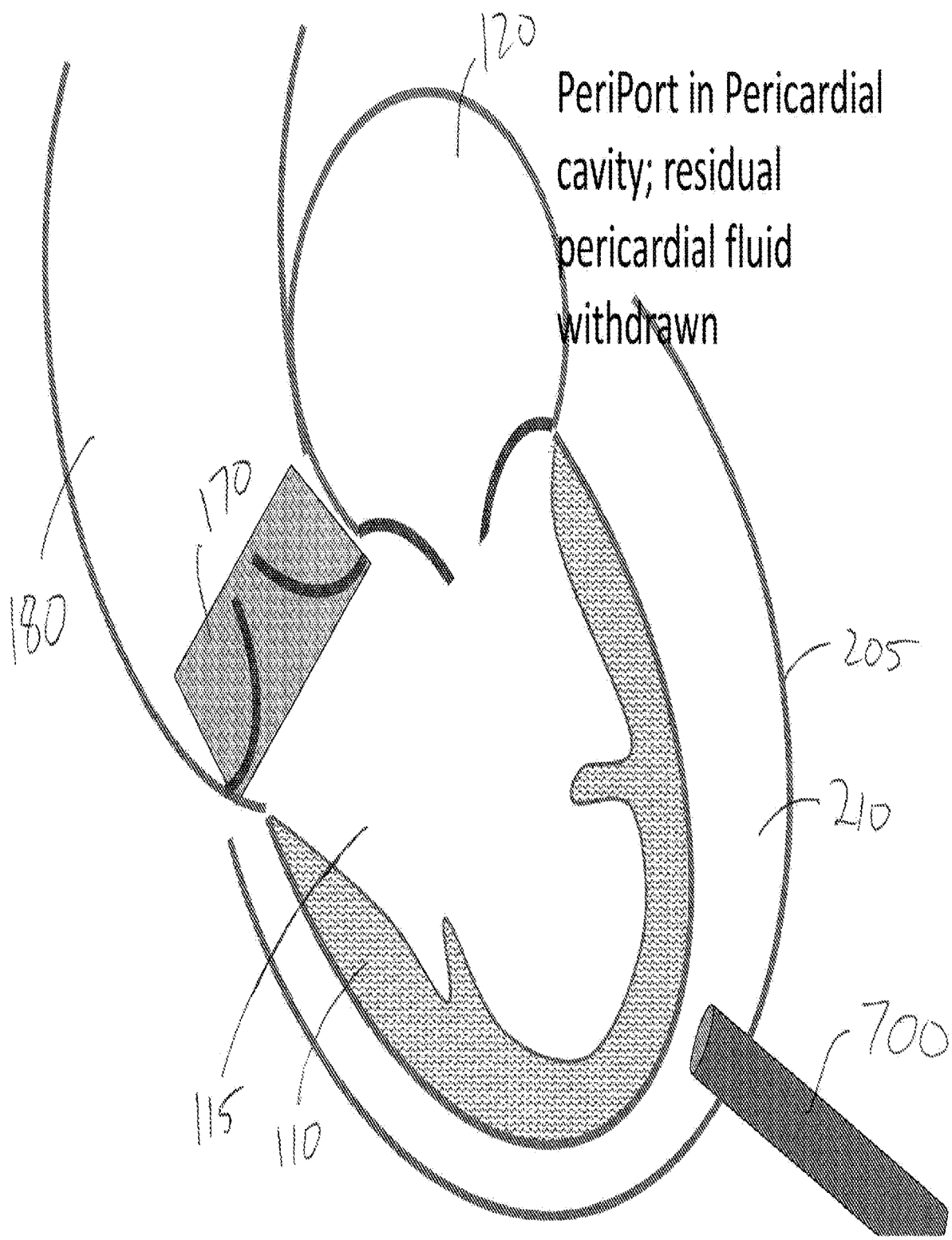

FIG. 34 shows the periport remaining in the pericardial space (cavity) which may be inflated by insertion of fluid and FIG. 34 is intended to show the removal or withdrawal of residual pericardial fluid via a syringe deployed through the periport so that the pericardial space returns to normal via the periport under image guidance.

Figure 35:
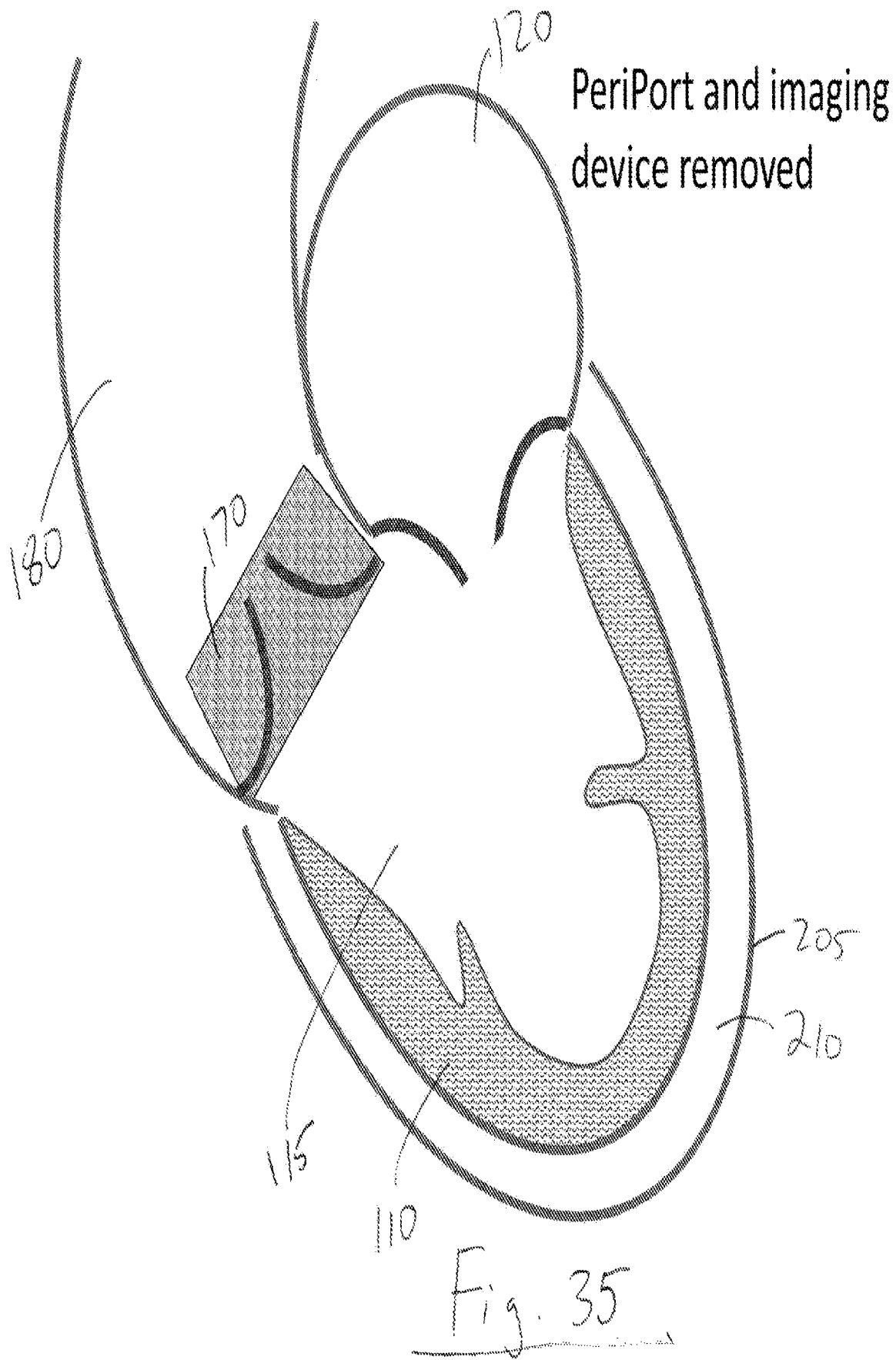

FIG. 35 shows the removal of the periport leaving the prosthesis replacement heart valve in place and the myocardium sealed by the closure device with pigtails (not shown).

Figure 36:
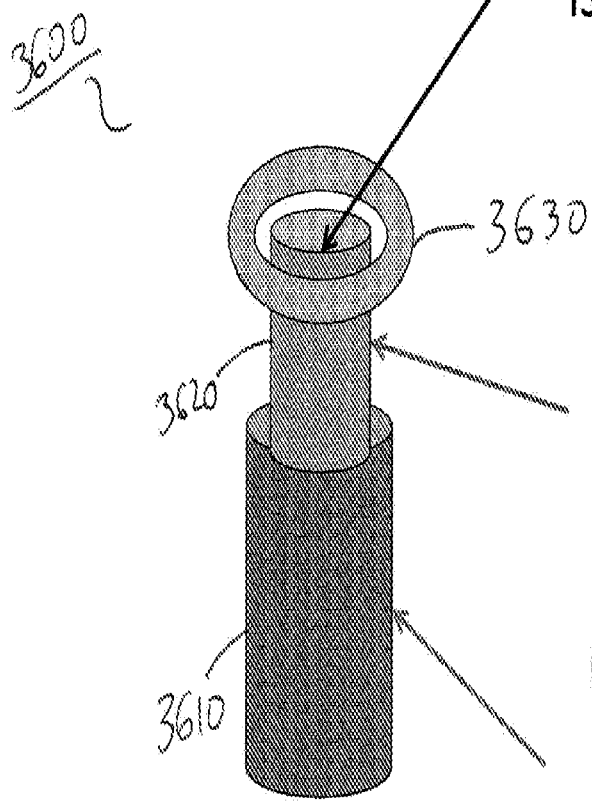

FIG. 36 shows an exemplary mitral valve repair mechanism consisting of an inner cylindrical strut inside an outer cylindrical strut, with an elastic band mounted on the inner strut for subsequent deployment.

FIG. 37A, FIG. 37B, and FIG. 37C show examples of surgical tools which may be delivered to the mitral valve in the inner cylindrical strut. FIG. 37A shows a loop. FIG. 37B shows scissors, and FIG. 37C shows a scalpel. Other tools that may be delivered in the same manner include a suction device, electro-cautery device, a cryo-cautery device, a plunger, or other surgical tools (not shown).

Figure 38:
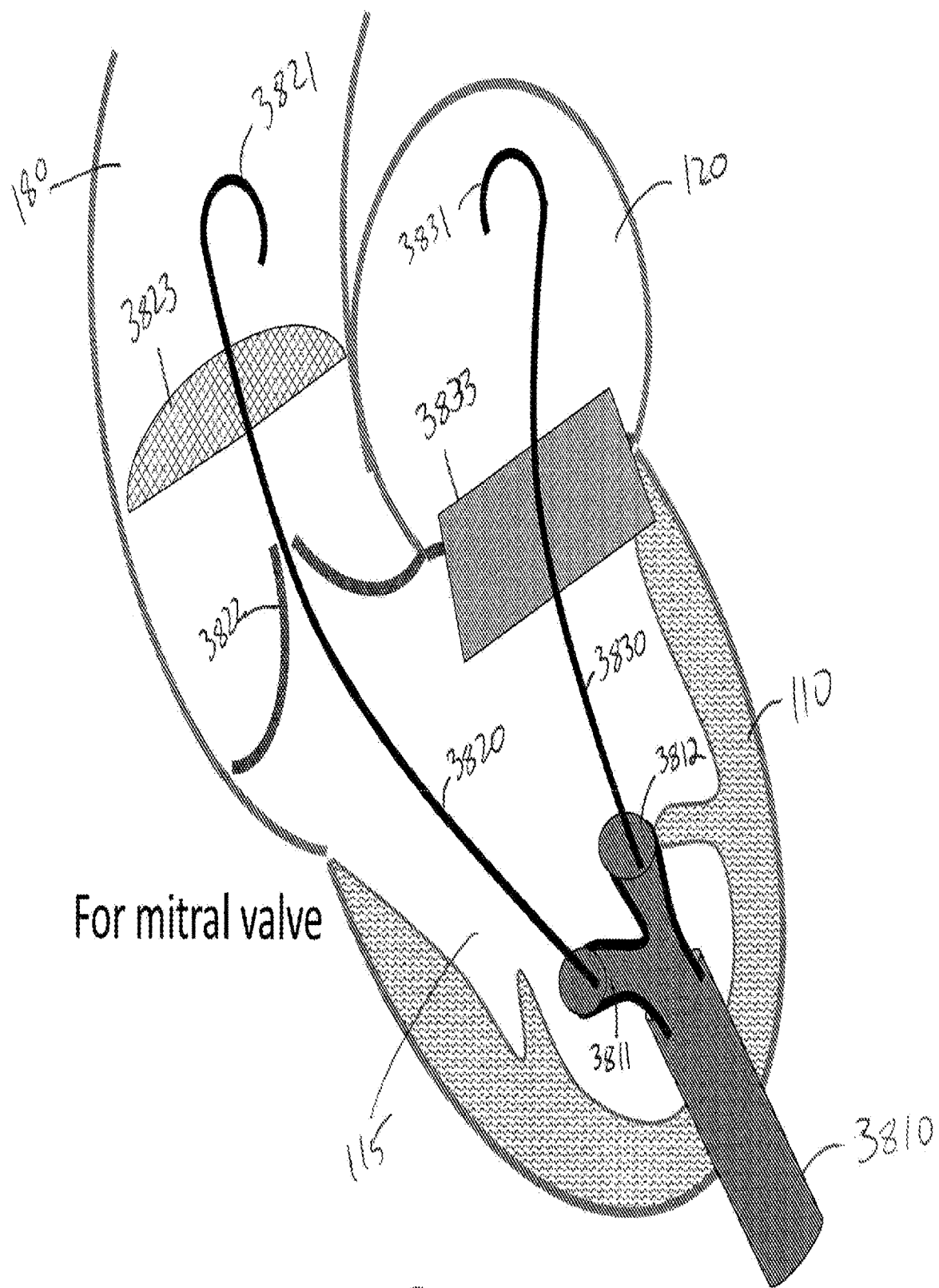

FIG. 38 shows the use of a bifurcated delivery catheter (periport) to insert a-mitral valve prosthesis. Two lumen of a periport may carry two different guide wires (not shown) or a bifurcated lumen (pair of pants legs) may be used for deployment in two different directions. An atrial filter is delivered to and deployed in the ascending aorta through the first opening of the bifurcated periport (in a similar manner as discussed above for an aortic valve replacement and repair), and a prosthetic mitral valve delivery system may be delivered to and deployed to replace a defective mitral valve through the-second opening of the bifurcated periport (the defective valve may be deployed and replaced in a similar manner to the aortic valve using the ventricular apex and closed in a similar manner).

Figure 39:
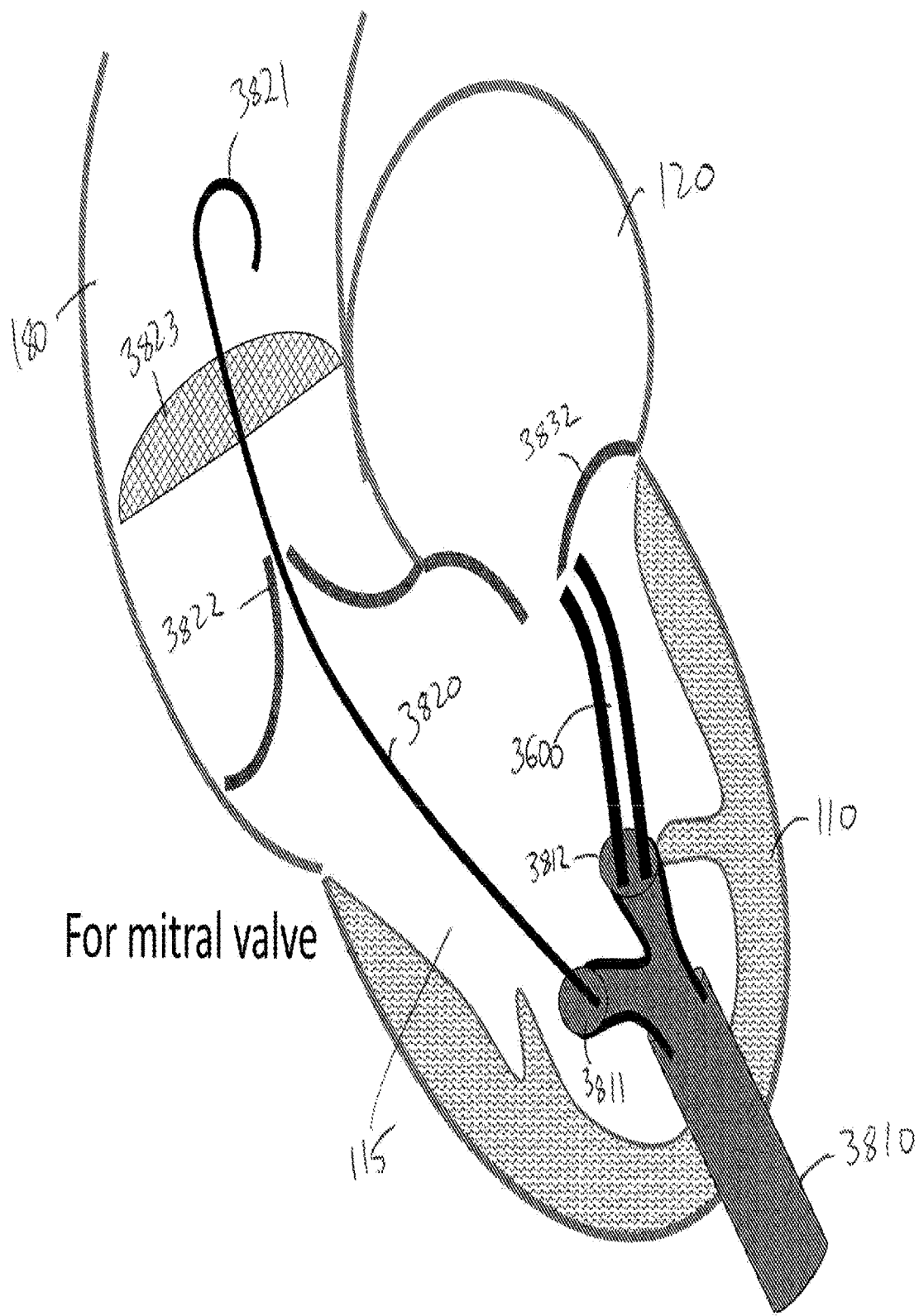

FIG. 39 further shows the use of a bifurcated periport to perform repairs on the mitral valve using the repair mechanism depicted in FIG. 36. An atrial filter is delivered, to and deployed in the ascending aorta through the first opening of the bifurcated periport, and a repair mechanism is delivered to the mitral valve region through the second opening of the bifurcated periport.

Figure 40:
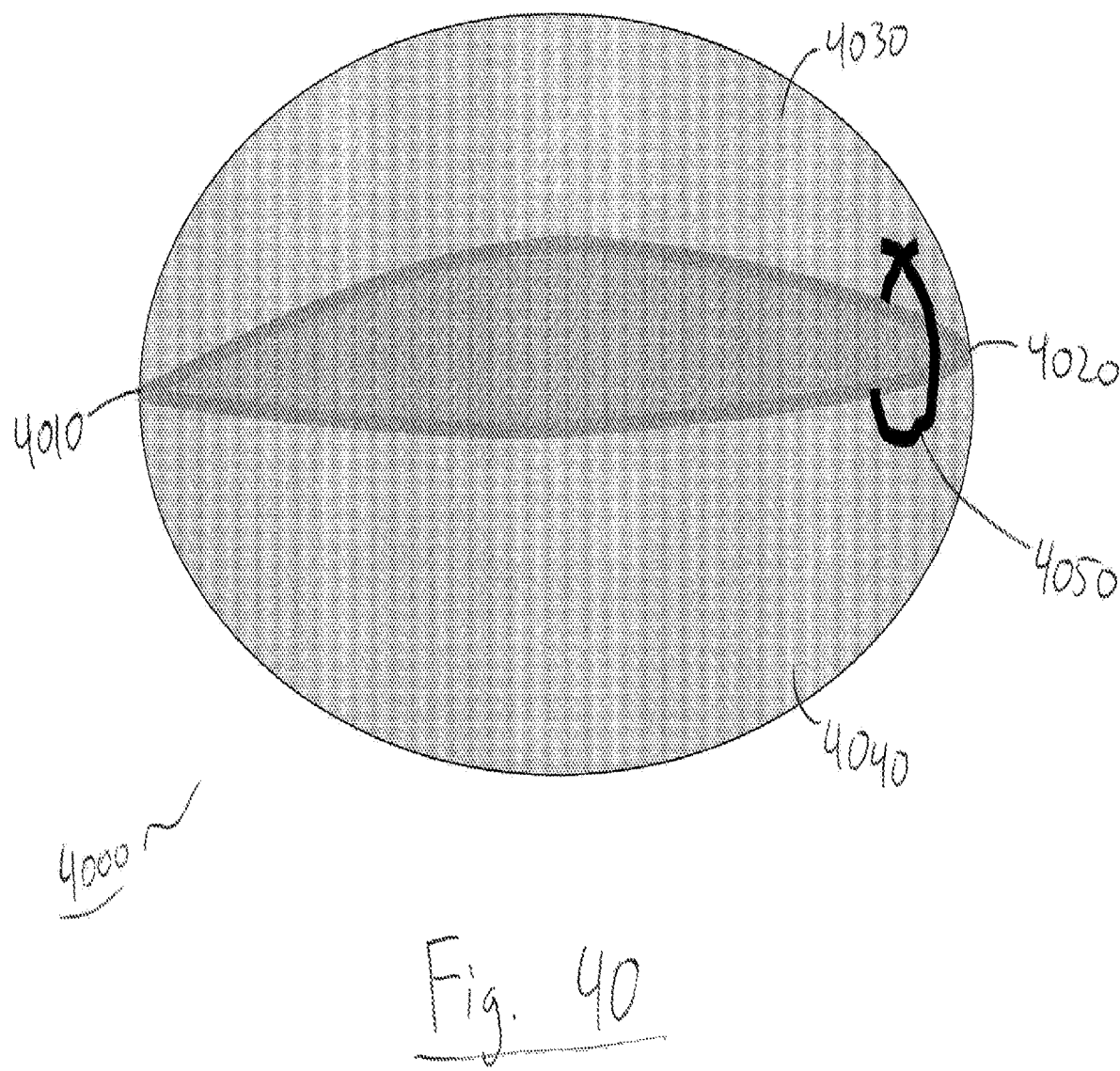

FIG. 40 shows the placement of a commissural stitch to reduce the opening of a valve that cannot fully close because of dilation in its leaflet, FIG. 41A shows a delivery needle for delivering a commissural stitch across two leaflets of a mitral valve.

FIG. 41B shows the delivery needle advanced through both leaflets of the mitral valve with the pigtail end of the suture protruding from the second leaflet.

FIG. 41C shows the delivery needle being retracted out of the second leaflet, leaving the suture held in place by the pigtail end.

FIG. 41D shows a partially delivered commissural stitch with the delivery needle mostly retracted and the leaflets still apart.

FIG. 41E shows a fully delivered commissural stitch with the delivery needle fully removed and the suture holding the leaflets together. So as the delivery needle is removed, the leaflets are pulled together reducing the size of the opening in a defective mitral valve.

Figure 42A:
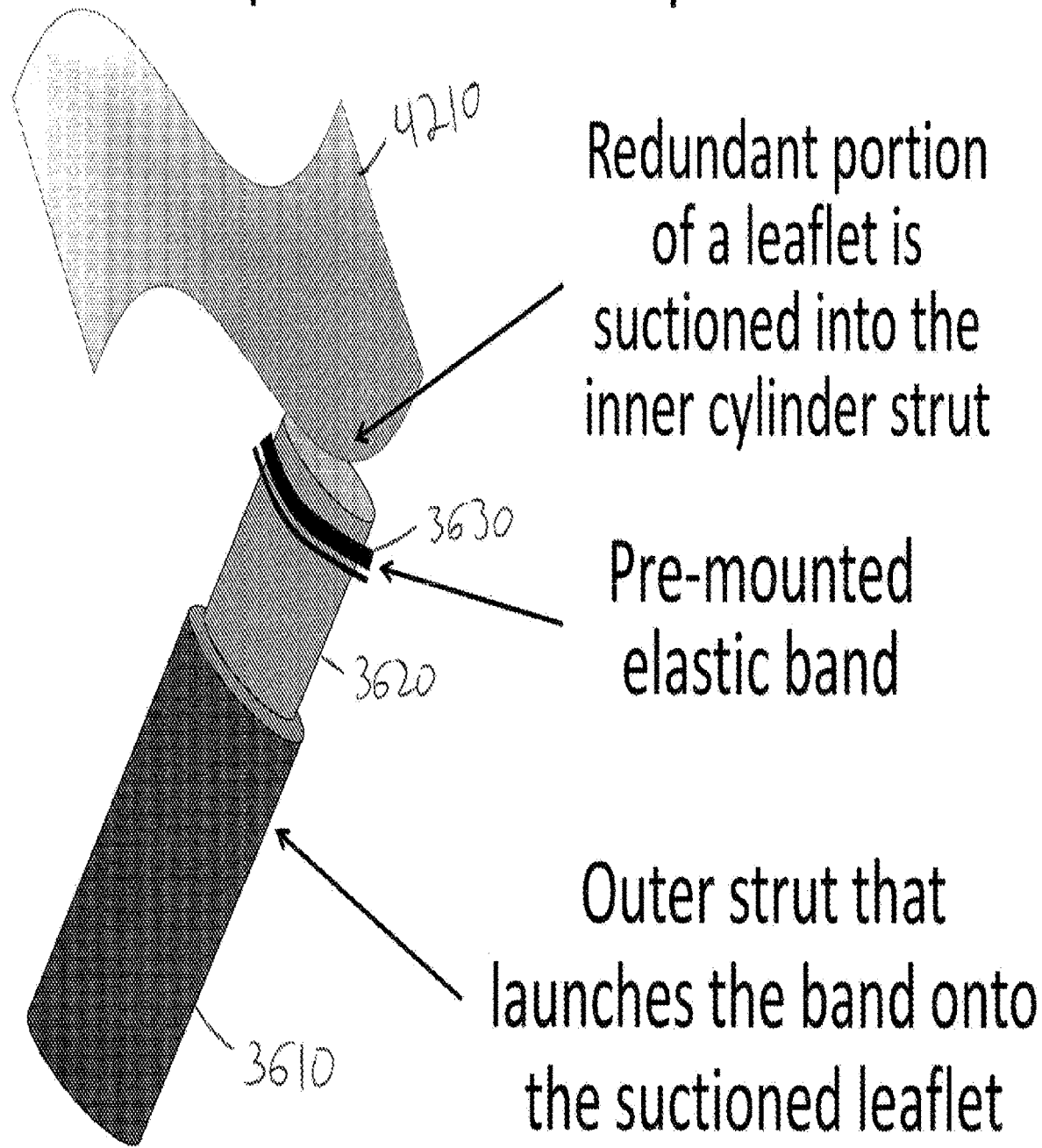

FIG. 42A shows the redundant portion of a leaflet being suctioned into the inner cylinder strut carrying an elastic band as per FIG. 36.

Figure 42B:
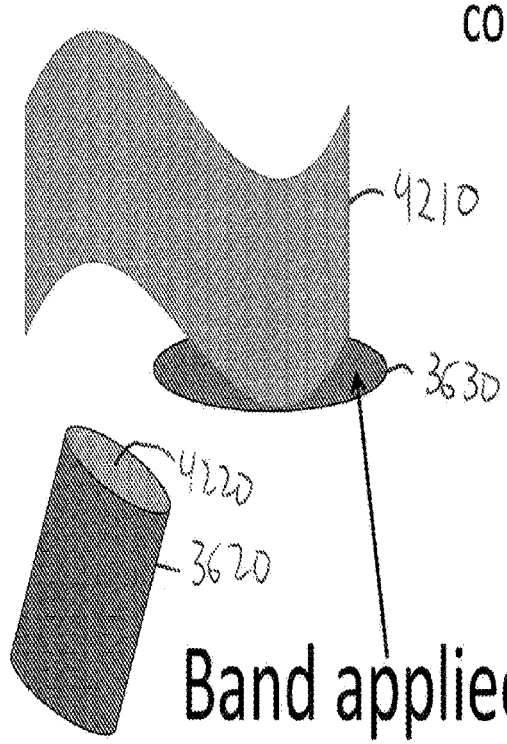
Figure 42C:
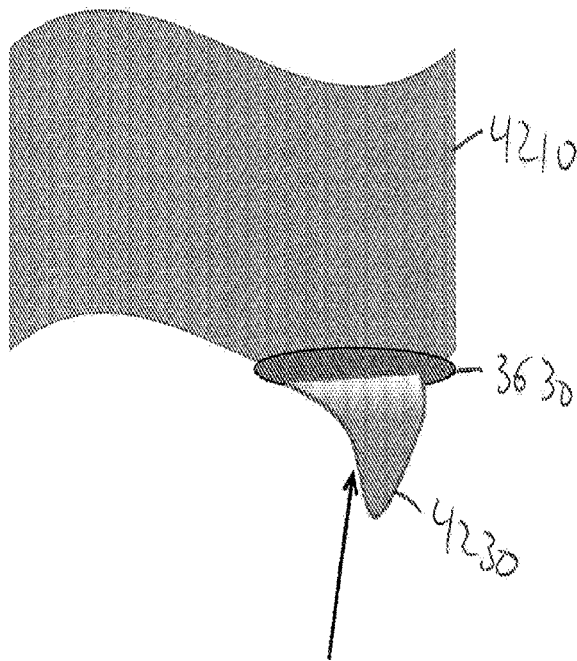

FIG. 42B and FIG. 42C show the redundant portion: of the leaflet being suctioned into the inner cylinder strut and an elastic band or loop pushed off the strut and applied to the redundant portion to tighten the leaflet.

What follows is a detailed discussion of embodiments and methods of the present invention comprising both apparatus and methods for replacement or repair of cardiac valves.

Figure 1:
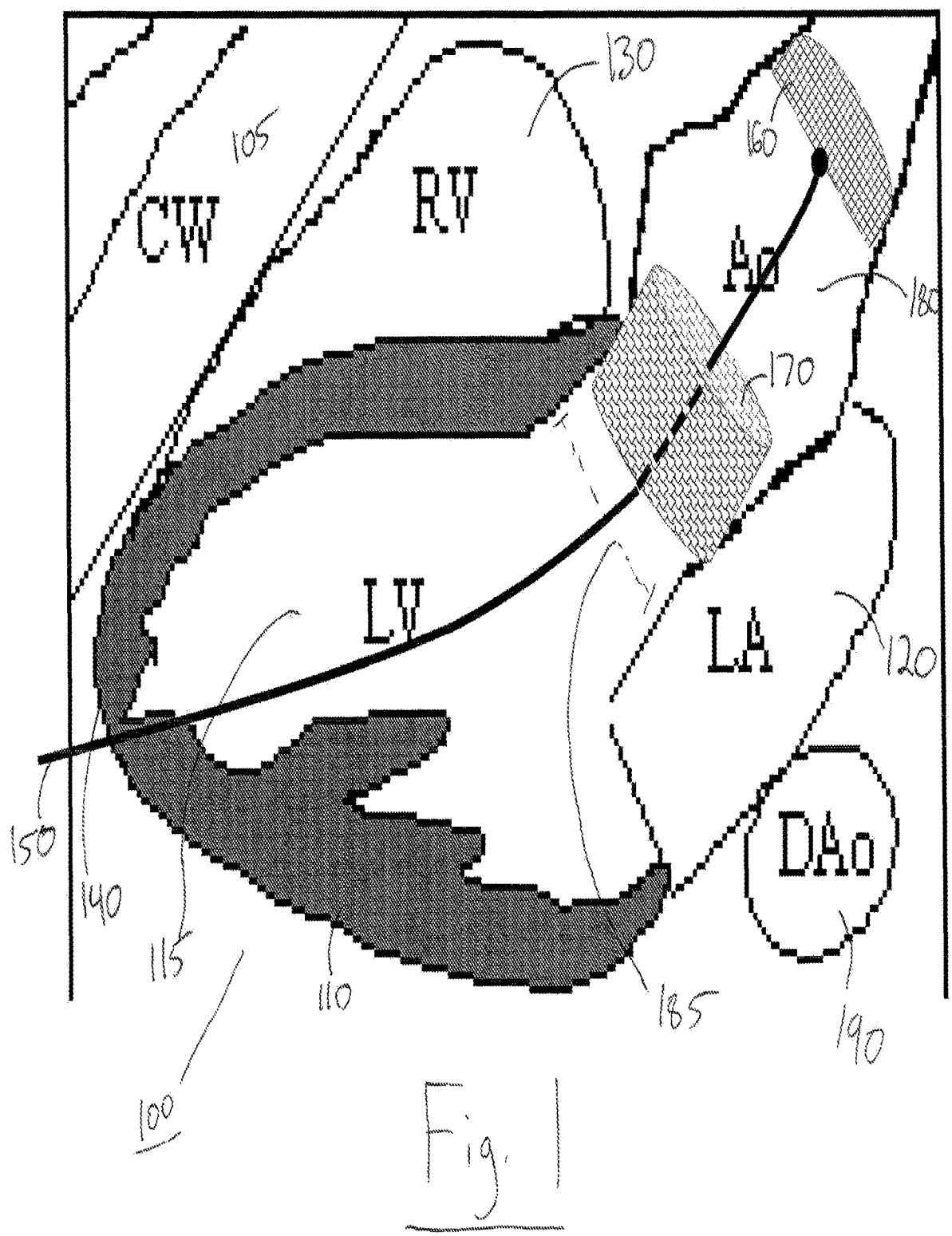
FIG. 1 comprises a drawing in two dimensions of the heart and chest wall (CW) which is penetrated by an image guided catheter and periport and other components. What are shown are the myocardium muscle, the left ventricle (LV), the left atrium (LA), the right ventricle (RV), the ascending aorta (AO), the descending aorta (DAo), the left ventricular apex and the left ventricular outflow tract (LYOT) of the heart. What is shown of the present invention comprises a guide wire 150 (without any surrounding tube structures for .filter or prosthesis delivery), a deployed prosthesis and a deployed, opened umbrella-like aortic filter to prevent stroke. The prosthesis and filter are shown located between the LYOT and the ascending aorta.

DETAILED DISCUSSION aspects summarized above can be embodied in various forms. The. following description shows, by way of illustration, combinations and configurations in which the aspects can be practiced by the various image guided catheter-like devices discussed and utilized in sequence in a method for replacing or repairing a defective heart valve, it is understood that the described aspects and/or embodiments are merely examples, it is also understood that other aspects and/or embodiments can be utilized, and that structural and functional modifications can be made, without departing from the scope of the present disclosure. Furthermore, modifications to the method(s) of repair and replacement of cardiac valves should not be considered limited in scope to the disclosure but may involve known processes and devices and procedures to those of ordinary skill in the art Referring to FIG. 1, there is shown a drawing in two dimensions of the: heart 100 and. chest wall (CW) 105 which may be penetrated by an image guided catheter (not-shown) or periport (not shown) and other components of a sequence of devices used for cardiac valve replacement and repair. The first example that will be discussed is aortic valve repair. What are shown are the myocardium muscle 110 the left ventricle 115 (LV), the left atrium 120 (LA), the right ventricle 130 (RV), the ascending aorta 180 (AO), the descending aorta 190 (DAo), the left ventricular apex 140 and the left ventricular outflow tract 185 (LYOT) of the heart. What is shown of the present invention comprises a guide wire 150 (without any surrounding tube structures for filter or prosthesis delivery. aortic filter 160 shown), a deployed prosthesis valve 170 and a deployed, opened umbrella-like aortic 'filter 160 to prevent stroke. The prosthesis and filter are shown located between the LVOT and the ascending aorta. FIG. 1 thus provides in abbreviated from a method and apparatus for repairing a heart valve such as the aortic valve 170 and preventing stroke via an aortic filter 160. The method may utilize many of the patented and patent pending devices disclosed in his prior patents and applications described briefly in the background of the invention but modified to provide specific functionality to facilitate cardiac valve replacement or repair.

A convention used in this patent application relates to the use of reference numerals such as 105 standing for chest wall The first number 1 in 105 refers to the figure in which the element first appears and the next two digits 05 represent the element identified, in this case, a chest wall (CW).

Figure 2:
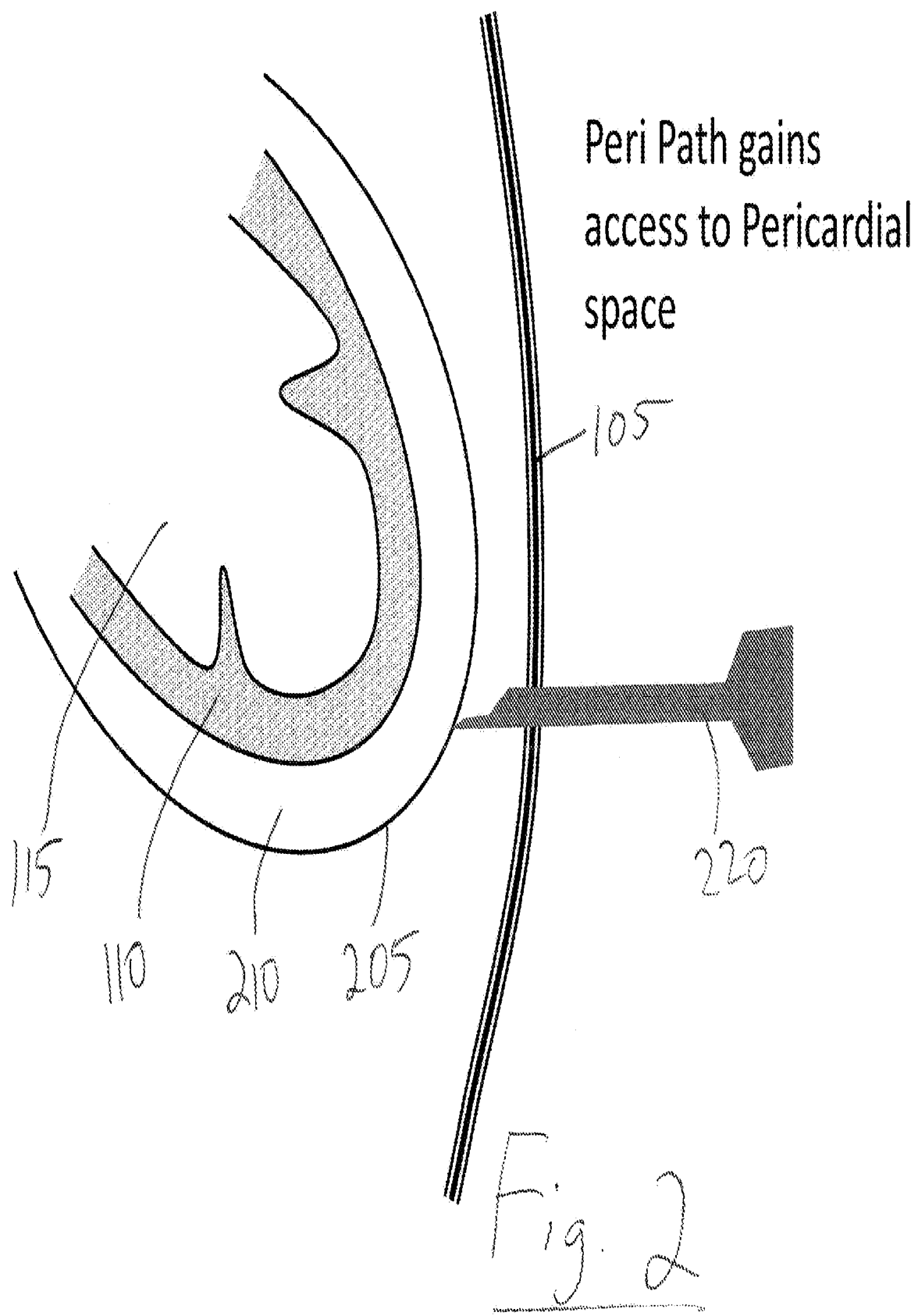
FIG. 2 shows an initial step of using an image guided catheter type referred to herein as a peripath penetrating the chest wall and under ultrasound vision guidance reaching the outer lining of the pericardium, but not yet penetrating the pericardial space.

Referring to FIG. 2, there is shown an initial step of using an image guided catheter type referred to herein as a peripath 220 penetrating the chest wall 105 and under ultrasound vision or other vision guidance such as optical coherence tomographic (OCT) vision or other real-time vision method known, the peripath 220 reaching the outer lining of the pericardium 205, but not yet penetrating the pericardial space 210 between inner and outer pericardial linings. Under vision, a site proximate the left ventricular apex 140 is selected for entry (with or without contrast) with no coronaries or vessels in view of a volume of myocardium taken by the introduction of an introducer needle (or guide wire) at an angle through the myocardium, A forward-directed ultrasound transducer at the' distal tip of the peripath 220 should be high resolution and shallow depth, and so comprise high frequency ultrasound on the .order of 10 MHz to 1 Gz to select a point of entry at an angle (so as to prevent the loss of blood into 'the. pericardial space 210, The myocardium 110 and inner left ventricular space 115 are also shown.

Preferably a small incision of about five to seven millimeters is all that is required in the chest wall 105 to permit entry of the peripath 220. The peripath comprises an ultrasound transducer lumen and at least one other lumen for any one of a needle, guide wire, sheath or tool and the same lumen may be used to replace, for example, one ultrasound transducer range with another range for proper vision of a site of interest. Also, the same lumen may be used to replace a solid introducer needle with a hollow needle portion of a syringe if needed. As wall be discussed further herein, a syringe may be used to expand the vicinity of the ventricular apex space between the inner and outer pericardial linings to provide room for the surgeon to work.

Figure 3:
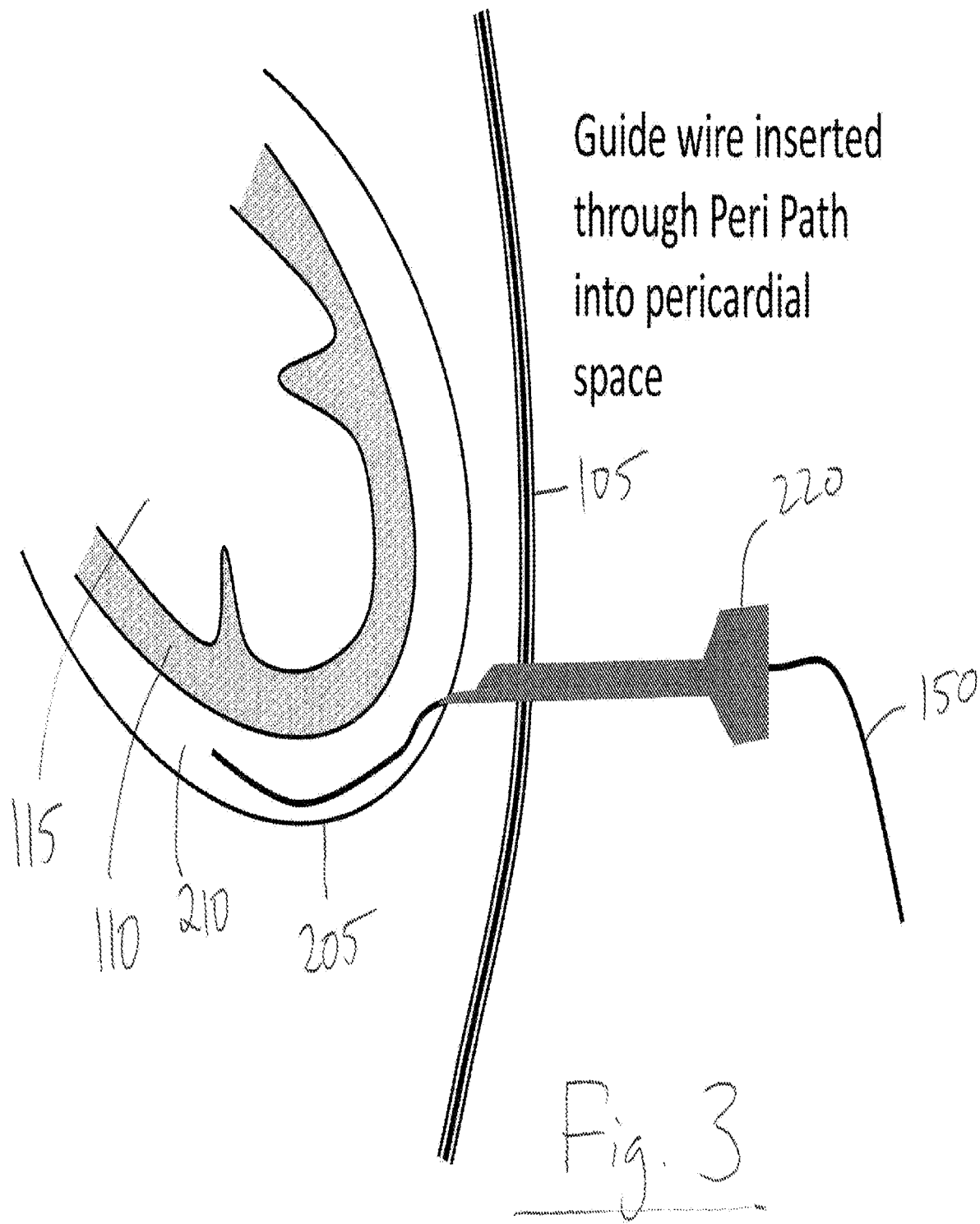
FIG. 3 shows a similar view of the peripath having approached the pericardium, puncturing the pericardium and inserting a guide wire into the pericardium space between the outer and inner pericardial linings. Fluid may be delivered by a hollow introducer needle (not shown) to expand the pericardial space at the opening location of the pericardium located proximate the left ventricular apex to provide a workspace.

Referring now to FIG. 3, a site of entry having been selected as described above, there is shown, a similar view of the peripath 220 having approached the pericardium outer lining 205, puncturing the pericardium 205 outer lining, for example, with a needle and inserting a guide wire 150 into the pericardium space 210 via a lumen between the outer and inner pericardial linings under vision (for example, ultrasound, with or without a contrast agent. Fluid (not shown yet) may be delivered by a hollow introducer needle (not shown) to expand the pericardial space at the opening location of the pericardium located proximate the left ventricular apex to provide a workspace. Further shown are the myocardium 110 and the left ventricle space 115 from FIG. 1.

(FIG. 4 shows removal of the peripath device leaving the guide wire 150 behind within the pericardial space 210 and exiting the chest wall 105.

Referring now to FIG. 5, there is shown the introduction of a sheath 500 (known in the art) through the chest wall 105 having ultrasound or other vision and advanced over the guide wire 150 to the opening of the pericardium outer lining 205 and penetrating the outer pericardium lining 205.

Referring now to FIG. 6, there is shown the removal of the guide wire 150 leaving the sheath. 500 equipped with ultrasound vision behind, penetrating both 'the chest wall 105 and the pericardium outer lining 205 to reach the pericardium space 210.

FIG. 7 introduces a periport 700 and shows the sheath 500 being an elongate cylinder for receiving a periport 700 (pericardium gateway or portal) that is pushed through the sheath into the pericardium space 210, The sheath 500 still plugs the hole in the pericardium outer lining 205 and remains stationary (stabilized) for example by suturing at the chest wall.

Figure 8A:
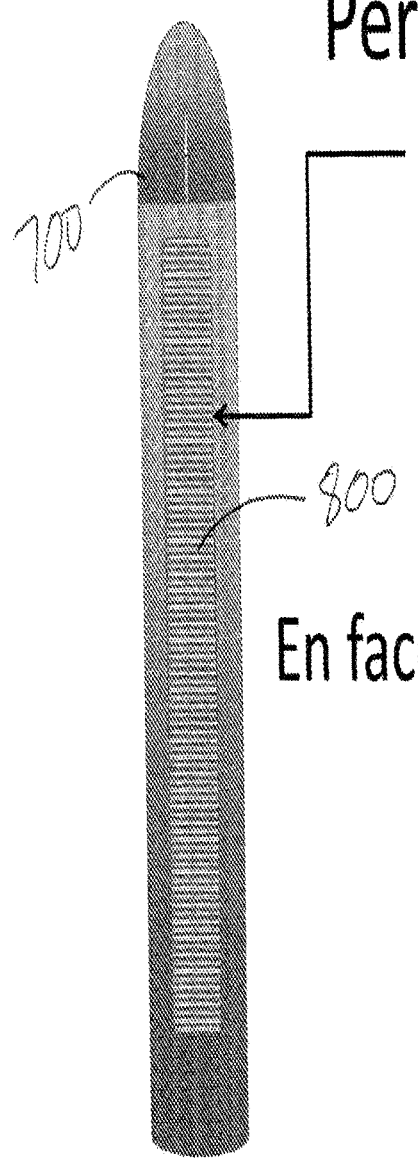
FIG. 8A and FIG. 8B show details of a periport transducer and an exemplary shape of the periport.
Figure 8B:
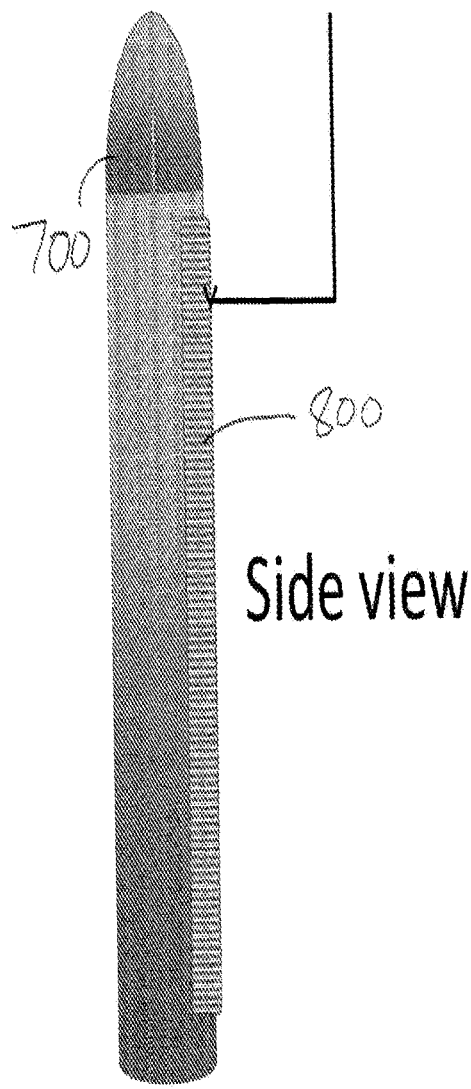

FIG. 8A and FIG. 8B show details of a periport transducer and an exemplary shape of the periport. FIG. 8A comprises an en face view of a periport ultrasound transducer linear array 800 of a periport 700 showing a deployable linear transducer array 800. FIG. 8B shows a side view where the deployable linear transducer array 8000 is depicted at one side of the periport having been twisted by the surgeon and moved to desired viewing position under vision (ultrasound transducer or other vision not shown).

Figure 9:
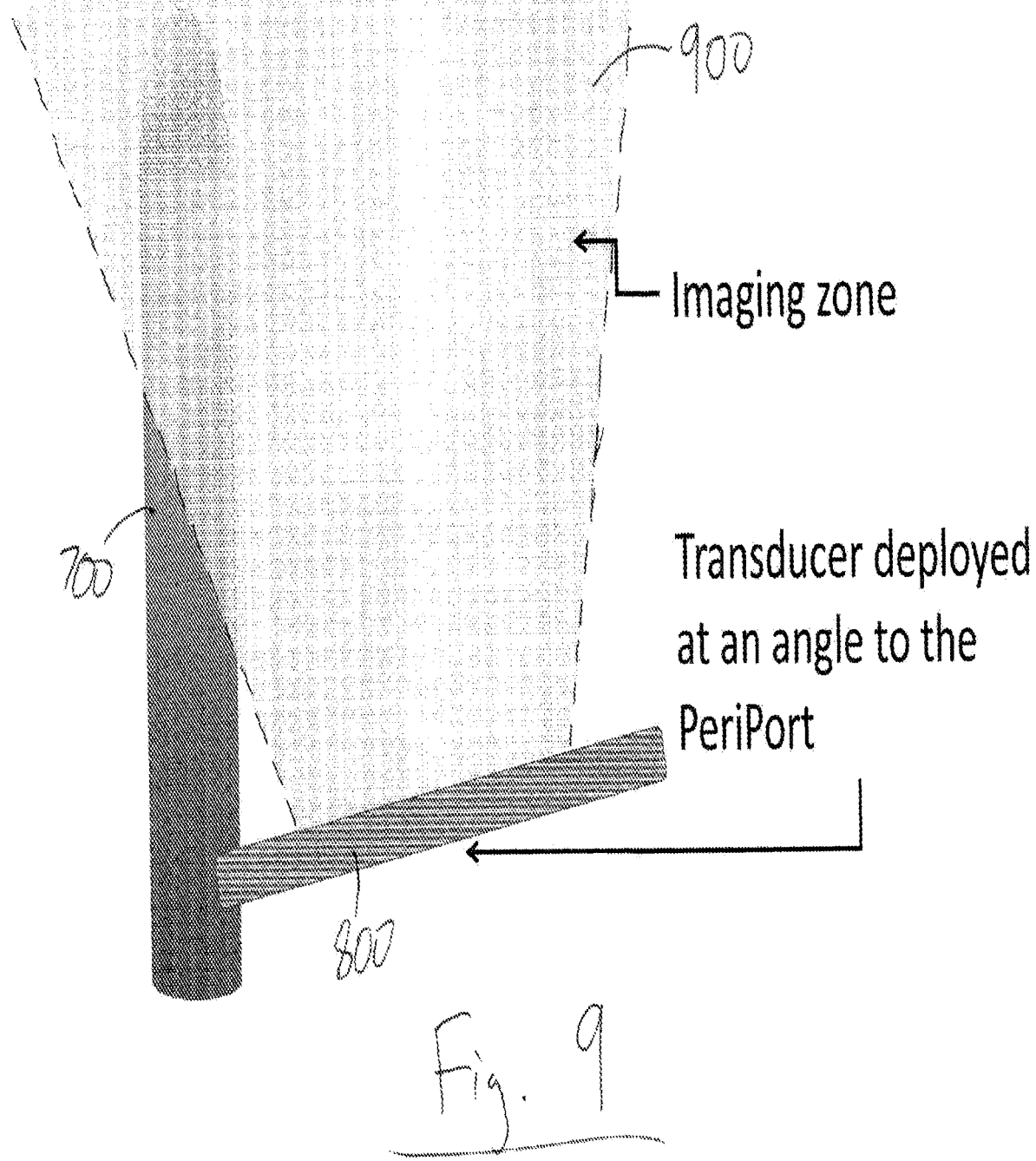
FIG. 9 shows deployment of the linear transducer array from the periport elongate body at an approximate orthogonal angle by use of a microelectromechanical motor system (MEMS) or a mechanical pulley system. It should be noted that an imaging zone which comprises a wide diameter cone space of ultrasound imaging is intended to capture a large vision of the heart and any tools or devices delivered from the distal (patient end) tip of the periport. The periport may be twisted as discussed above by the surgeon before deployment to achieve an optimal ultrasound vision imaging zone

Referring to FIG. 9, there is shown deployment of the linear transducer array 800 from the periport 700 elongate body at an approximate orthogonal angle by use of a microelectromechanical motor system (MEMS) or a mechanical pulley-system, it should be noted that an imaging none 900 which comprises a wide diameter cone space of. for example, ultrasound imaging (with or without a contrast agent, not shown) is intended to capture a large vision, of the heart and day tools or devices delivered from the distal (patient end) tip of the periport 700 and surrounding tissue. The periport 700 may be twisted by the surgeon under vision, as discussed above before deployment to achieve an optimal ultrasound vision cone of imaging zone 900.

Figure 10A:
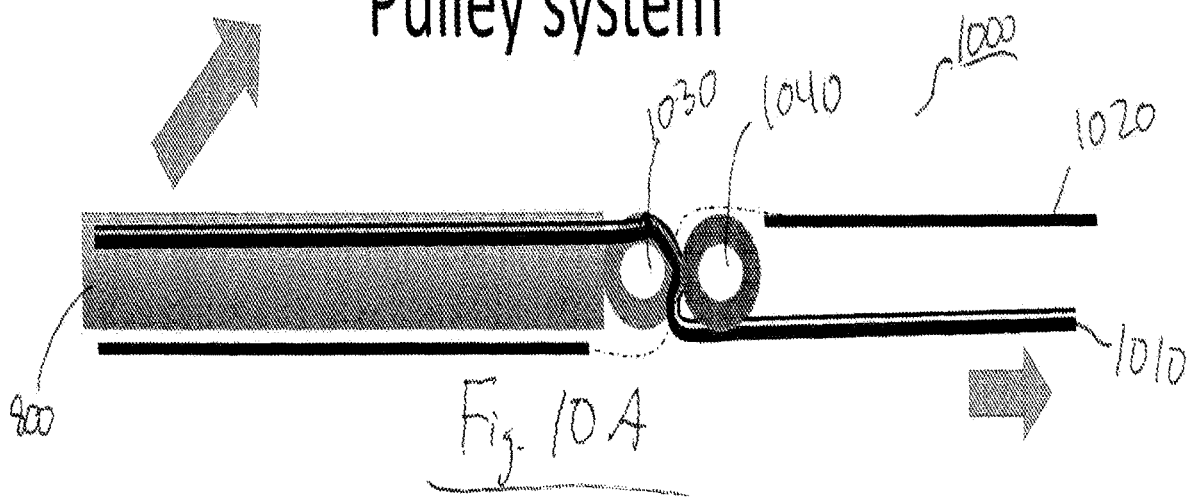
FIG. 10A shows details of an exemplary pulley system for raising and for later lowering the linear transducer array of FIGS. 8A, 8B and 9. The system may comprise first and second pulleys and flexible wires for raising (via the top wire) and lowering (via the bottom wire) the linear ultrasound transducer array at a desired vision location.

FIG. 10A shows details of an exemplary pulley system for raising and for later lowering the linear transducer array of FIGS. 8A. 8B and 9. The system may comprise first and second pulleys 1030, 1040 and flexible wires 1010, 1020 for raising (via the top wire 1010) and lowering (via the bottom wire 1020) the linear ultrasound transducer array 800 at a desired vision location for viewing, for example, the heart.

Figure 10B:
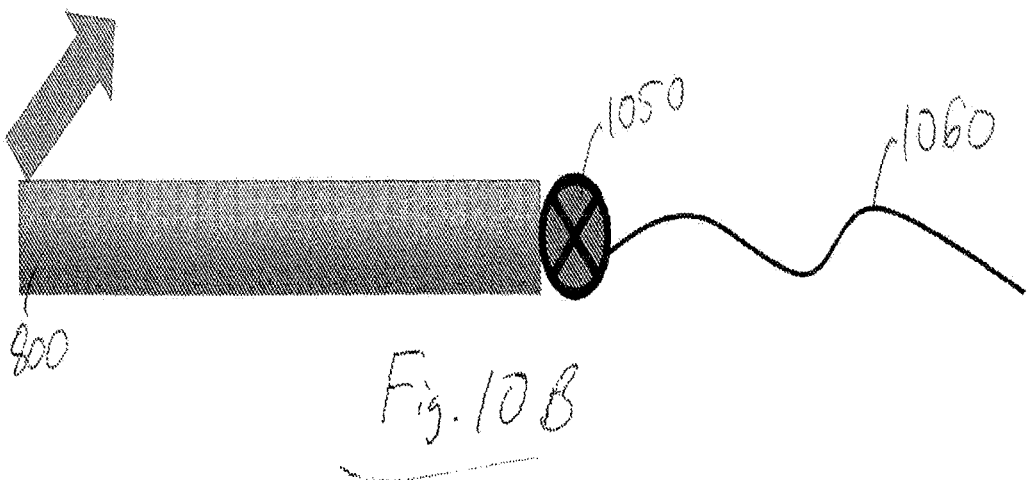
FIG. 10B shows details of an exemplary microelectromechanical motor system (MEMS) having an electric wire lead through the periport to the skin surface for turning on/off the motor and reversing the direction of the MEMS so that the linear transducer array may be either raised for vision or lowered for removal.

FIG. 10B shows details of an exemplary microelectromechanical motor system (MEMS) having an electric wire lead 1060 through the periport 700 to the skin surface for turning on/off the MEMS motor and reversing the direction of the MEMS so that the linear transducer array 800 may be either raised for vision or lowered for removal.

FIG. 11 shows the periport 700 of sheath 500 with the linear transducer array 800 deployed, between the chest wall 105 and the pericardium outer lining 205 and twisted into a position where it may provide vision of the pericardium space 210, left ventricular apex and the left ventricle 115 (and beyond).

Figure 12:
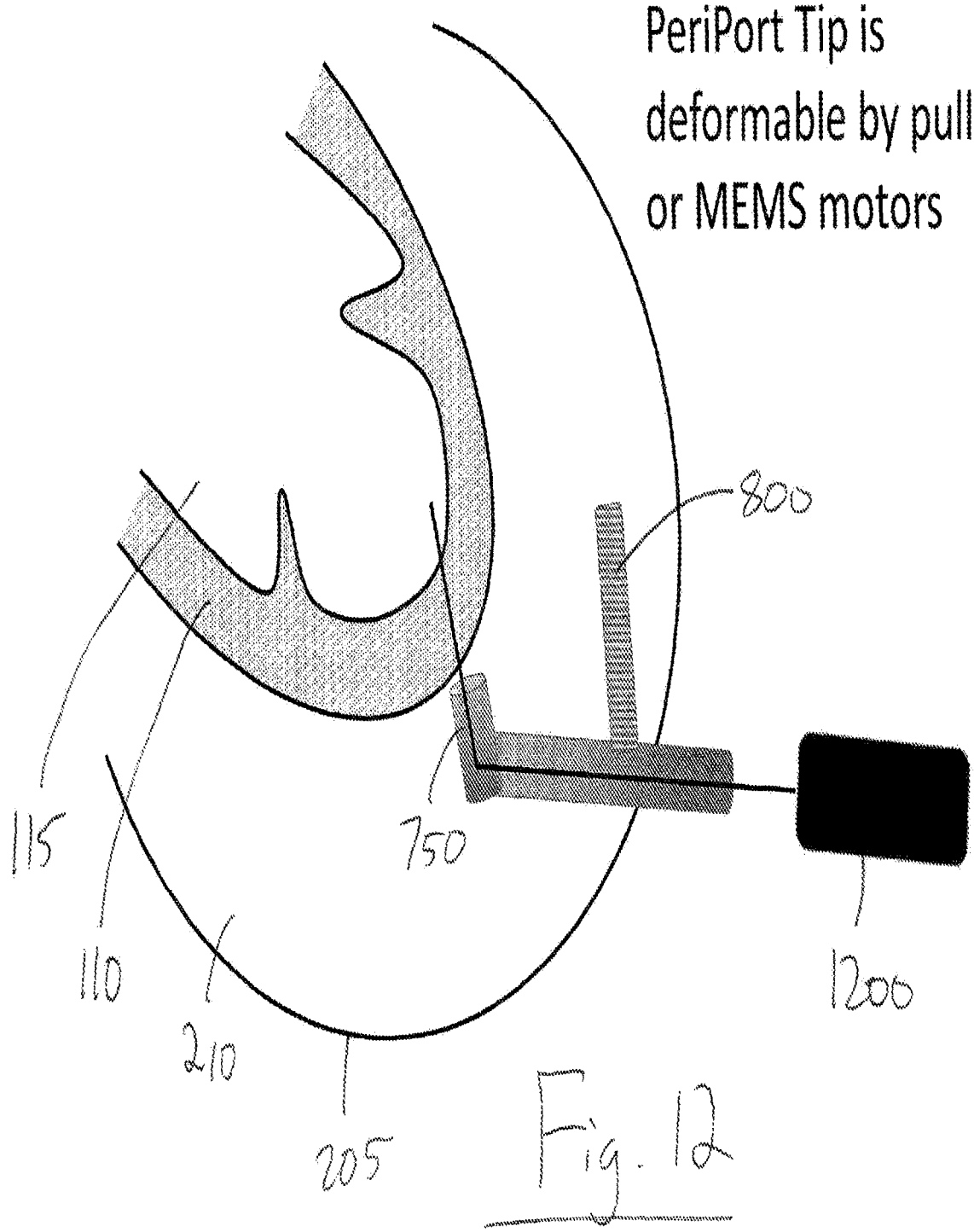
FIG. 12 shows that the periport, now comprising a portion including a needle referred to as a myopoint needle advanced through the periport which may comprise a distal, bendable periport tip portion deformable by pulley or a MEMS motor and at a proximate position with the linear transducer array having an Imaging none including the myocardium and ventricular apex, the bent periport tip and myopoint needle where myopoint is a contraction of myocardium and point. The bendable portion is bent so as to permit a, solid flexible myopoint needle to penetrate the myocardium at an angle so as to preclude blood flow through the angled hole formed by the myopoint needle pushed through the left ventricular apex at an angle.

FIG. 12 shows that the periport 700, now comprising a portion 750 including a needle (unnumbered) referred to as a myopoint needle 1200 (advanced by handle 1200) advanced through the periport 700 under vision which may comprise a distal, bendable periport tip portion 750 deformable by pulley or a MBMS .motor and at a proximate position with the linear transducer array 800 having an imaging zone including the myocardium 110 and ventricular apex, the bent periport tip 750. and myopoint needle 1200, where myopoint is a contraction of myocardium and point. The bendable portion 750 is bent so as to permit a solid flexible myopoint needle 1200 to penetrate the myocardium at an. angle so as to preclude blood flow through the angled hole formed by the myopoint needle pushed through the left ventricular apex at an angle. The myopoint needle 1200 may be hollow to permit, injection of saline or other benign solution into the pericardial space to produce a work-space within the pericardial space 210. Note that, toe hollow myopoint needle 1200 penetrates the myocardium 110 at an angle to preclude blood flow into the pericardial space 210. Consequently, subsequent closure of the myocardium at the point of entry will comprise a flap and not a direct hole through the myocardium. intraventricular pressure may close the wound to the ventricular apex.

Figure 13:
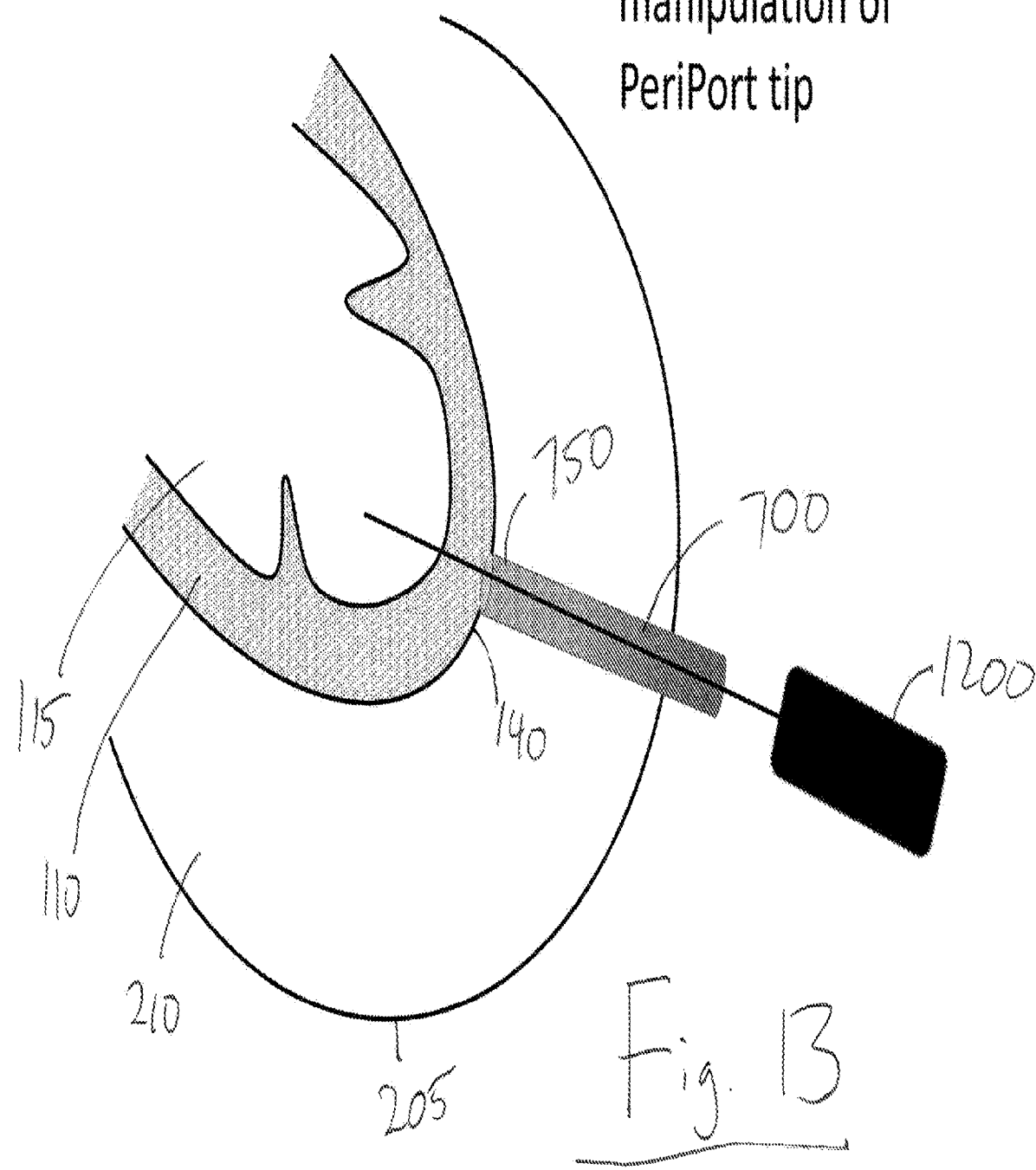
FIG. 13 shows that the periport/myopoint solid needle may be straightened by straightening the periport tip portion back to be proximate the left ventricular apex. The straightening occurs in myocardium muscle which is expected to ilex and withstand any blood pressure to leak into the pericardial space.

FIG. 13 shows that the periport/myopoint solid needle 1200 may be straightened by straightening the periport tip portion 750 back to form periport 700 again and to be proximate the left ventricular apex 140, The straightening occurs in myocardium muscle 110 which is expected to flex and withstand any blood pressure to leak: into the pericardial space 210.

Figure 14:
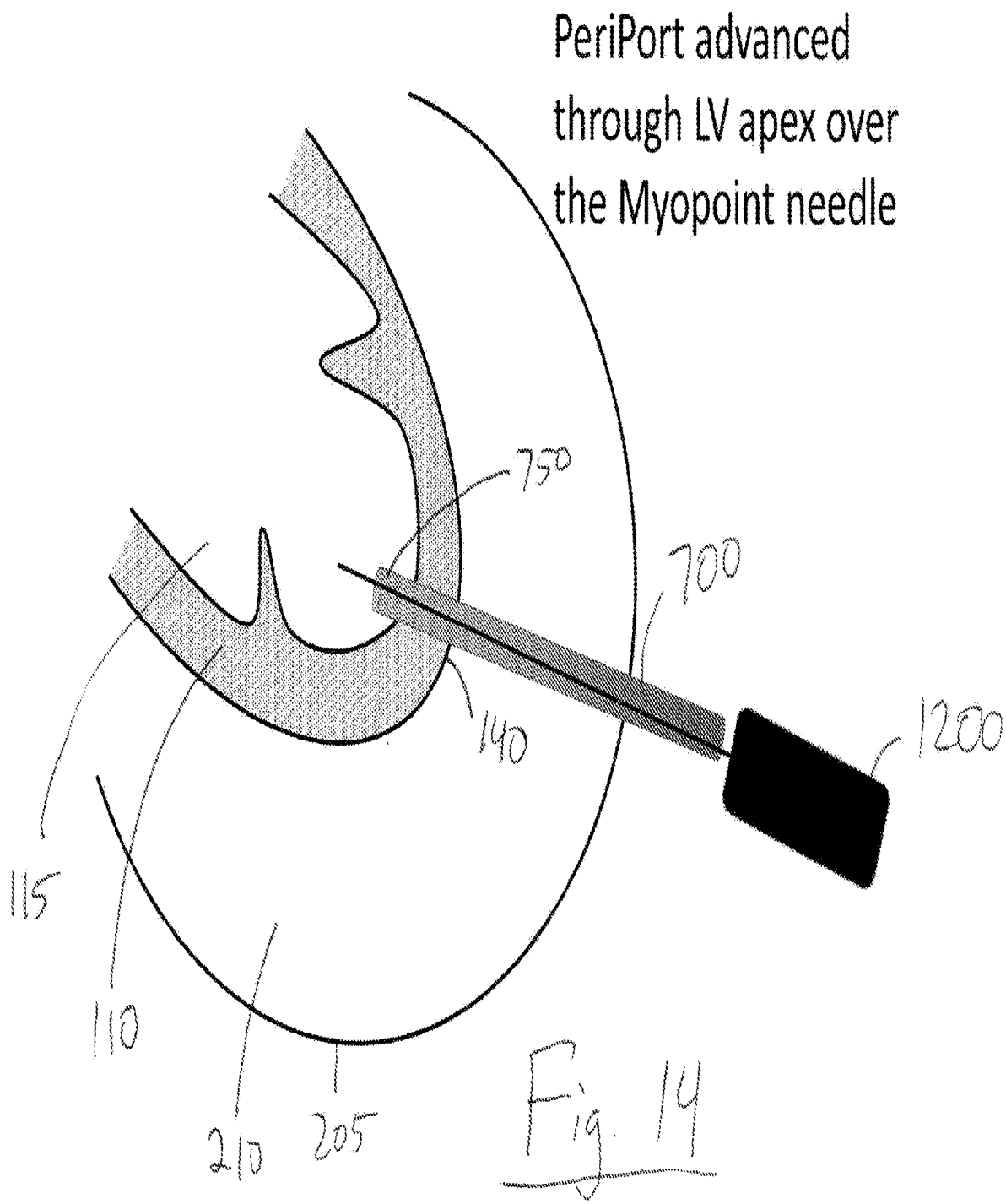
FIG. 14 shows the periport advancing through the hole made by the myopoint needle into the ventricular space via the needle acting as a guide wire entering the left ventricular apex at an angle and under vision (not shown). The large diameter of the perioport effectively plugs the angular hole at the left ventricular apex and prevents blood from entering the pericardial space.

FIG. 14 shows the periport 700 advancing through the hole made by the myopoint needle 1200 at the ventricular apex 140 into the ventricular space 115 via the myopoint needle 1200—acting as a guide wire, the periport 700 entering the left ventricular apex 140 at an angle and under vision (not shown). The large diameter of the perioport 700 effectively plugs the angular hole at the left ventricular apex 140 and prevents blood from entering the pericardial space 210.

Figure 15:
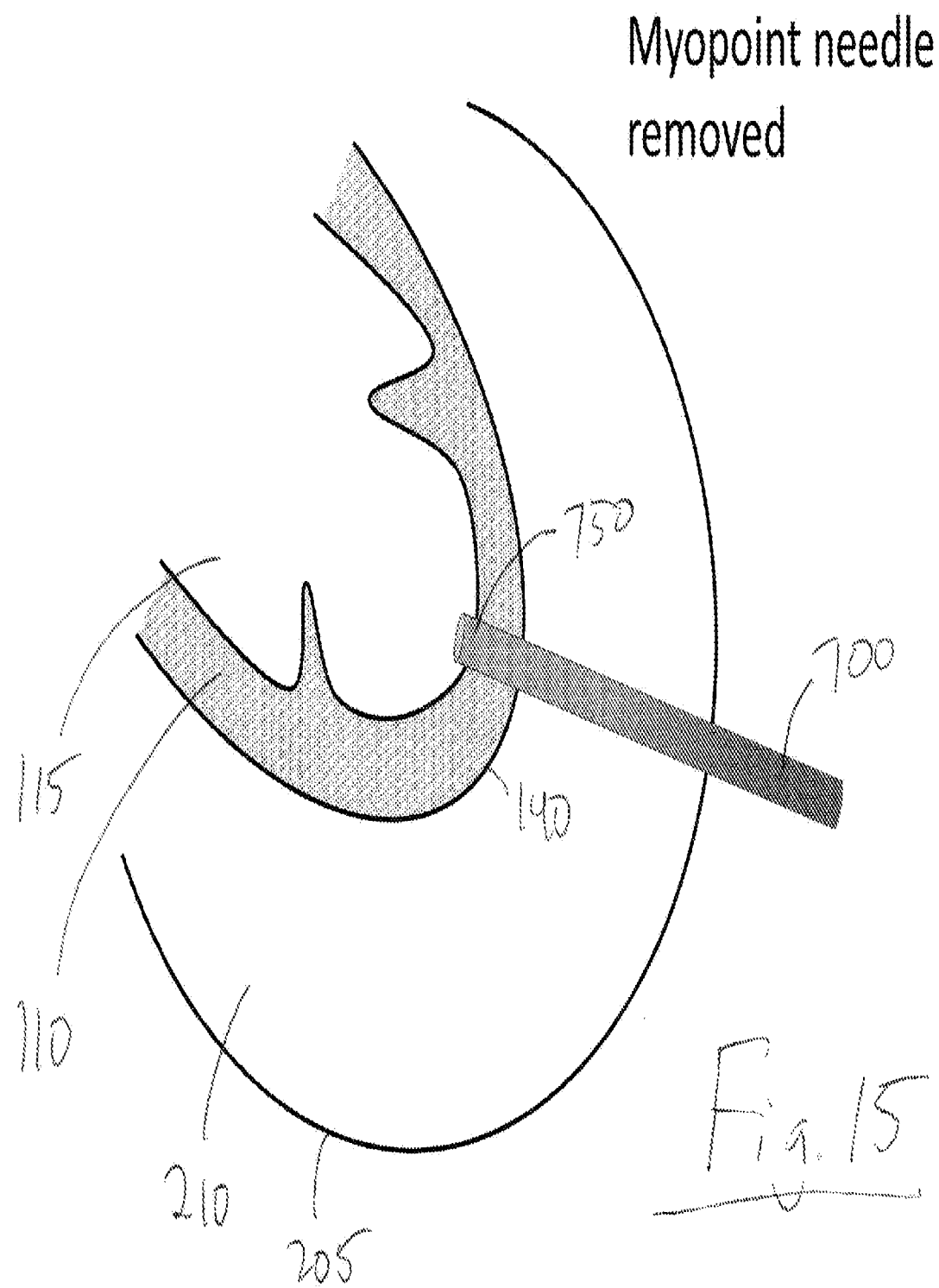
FIG. 15 shows the removal of the myopoint needle leaving the periport, under vision, penetrating the myocardium at the left ventricular apex at an angle and preventing blood to flow through the plugged myocardium hole.

FIG. 15 shows the removal of the myopoint needle 1200 leaving the periport 700, under vision, penetrating the myocardium 110 at the left ventricular apex 140 at an angle at periport portion 750 and preventing blood to flow through the plugged myocardium hole. The pericardial space 210 is still shown with added fluid to create a workspace for the surgeon.

Figure 16:
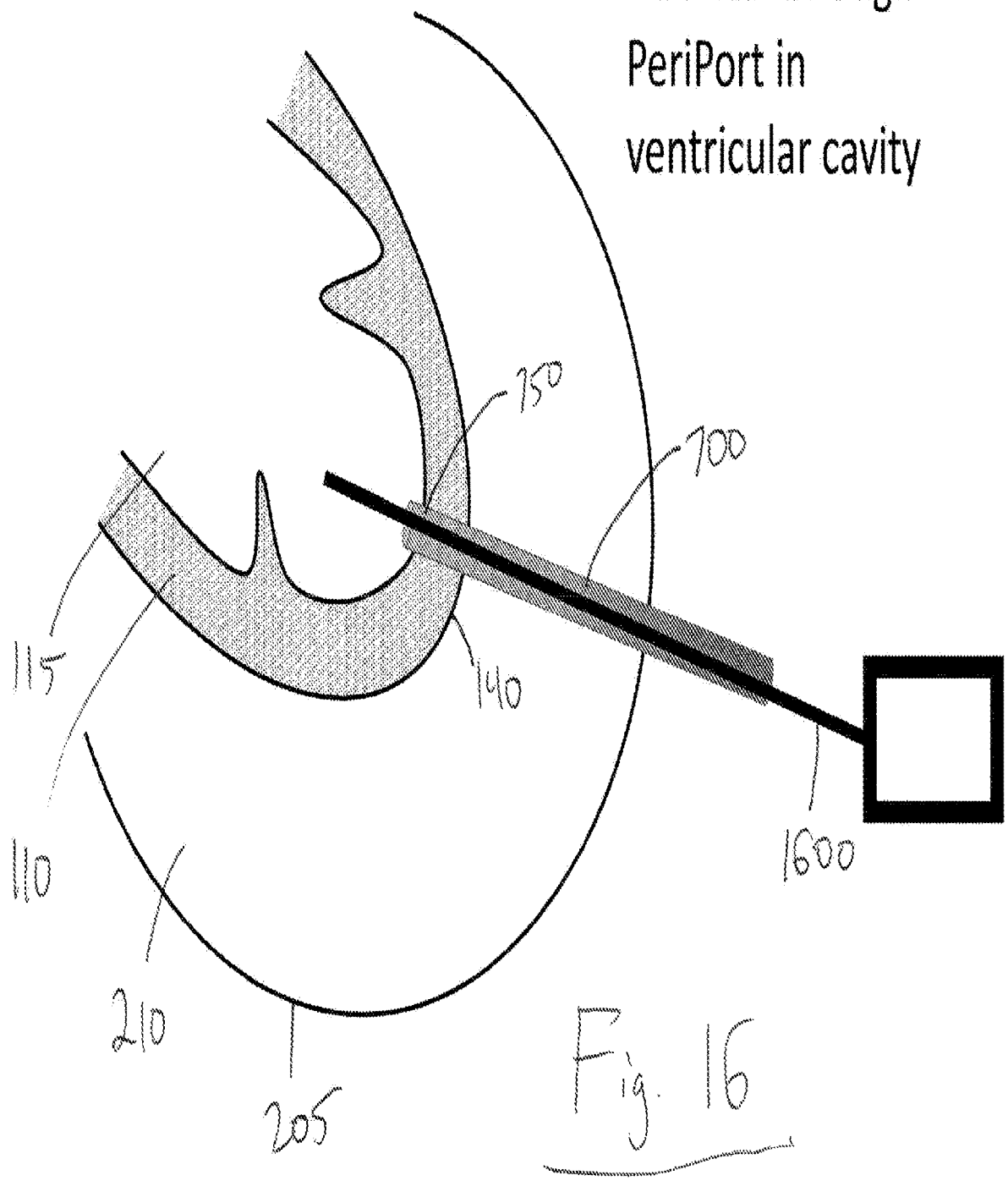
FIG. 16 shows the advancement of a telescoping/multichannel pericath that is shown in greater detail in FIG. 17. Pericath is short for pericardium, image-guided catheter. The pericath is a series of concentric tubular portions comprising and inner guide wire, an aortic filter delivery catheter, next, a prosthetic valve delivery tube or catheter and surrounded by an outer pericath comprising forward-directed ultrasound vision.
Figure 17:
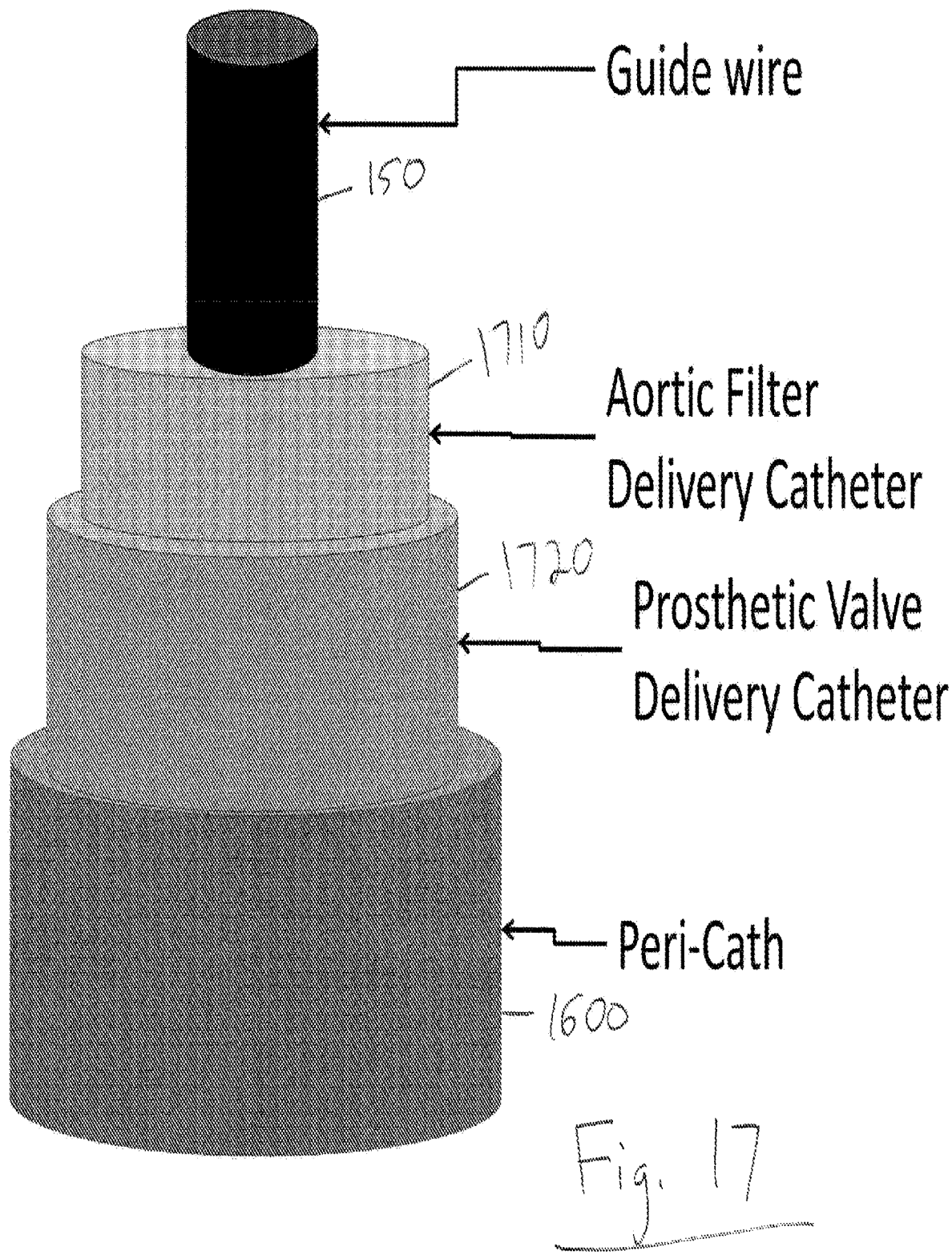
FIG. 17 is a perspective cross-sectional view of the pericath showing its inner diameter delivery systems comprising tubes or catheters and a central guide wire. The central guide wire is followed in diameter by. an aortic filter delivery catheter tube system; next, a prosthetic valve delivery tube system follows as diameter increases or catheter and the prosthetic valve delivery system is surrounded by the outer pericath catheter.

FIG. 16 shows the advancement of a telescoping/multi-channel pericath 1600 that is shown in greater detail in FIG. 17, Pericath is short for pericardium, image-guided catheter. The pericath 1601 is a series of concentric tubular portions comprising an inner guide wire 150, an aortic filter delivery catheter 1710, next a prosthetic valve delivery tube or catheter 1720 and surrounded by an outer pericath 1600 best seen in FIG. 17 and the pericath 1600 comprising forward-directed ultrasound or other vision via an elongate lumen and ultrasound transducer (not shown).

Figure 18:
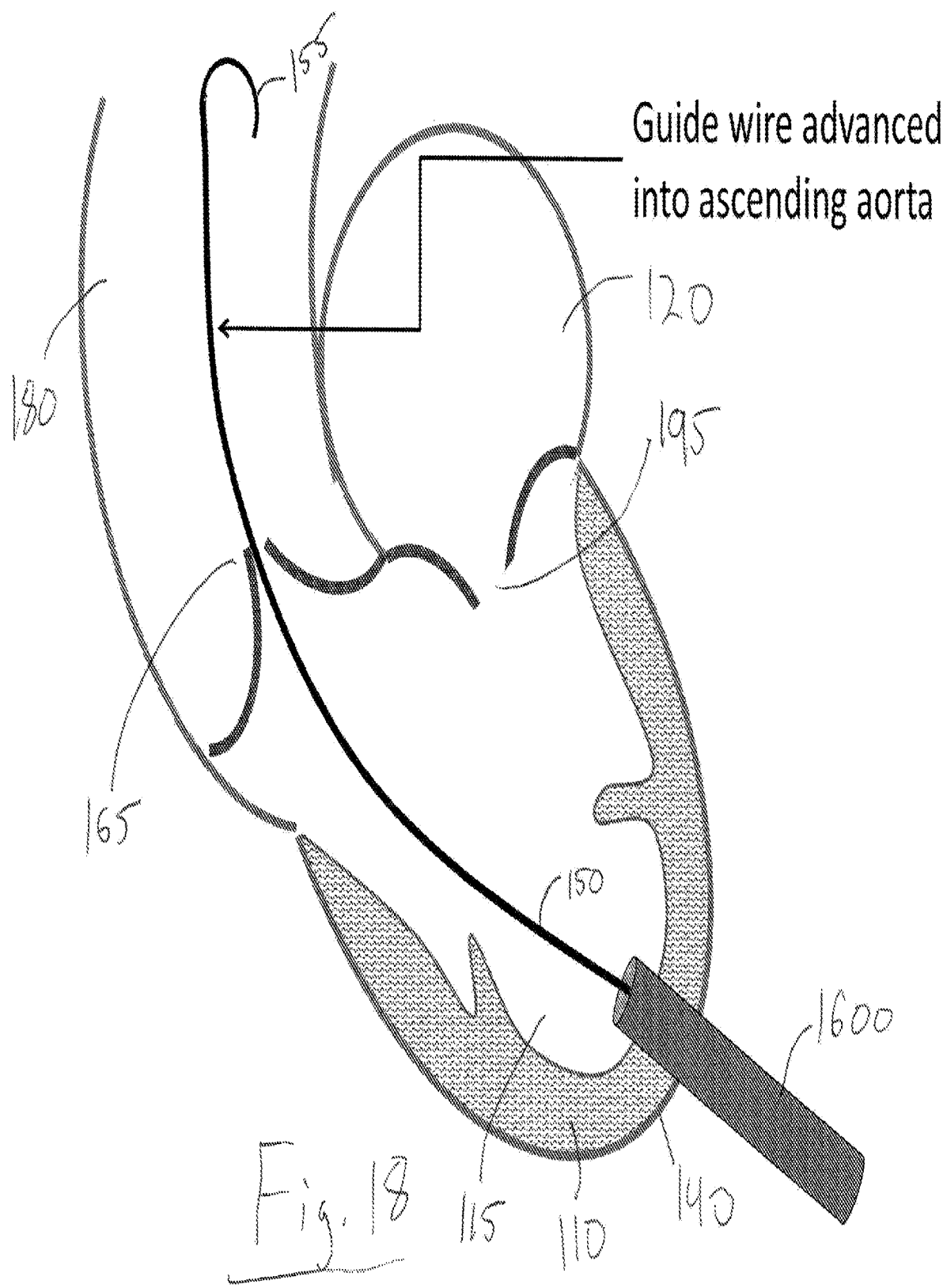
FIG. 18 show s deployment of a J-tipped (by way of example) guide wire from the telescoping/multi-channel pericath through a defective heart valve and deployment of the i portion of the tip of the guide wire as it is advanced under ultrasound vision into the ascending aorta. The J tip may prevent any inadvertent damage to the aortic walls and deploys automatically.

FIG. 17 is a perspective cross-sectional view of the pericath 1600 showing its inner diameter delivery systems comprising tubes or catheters and a central guide wire 150. The central guide wire 150 is seen in FIG. 17 followed in diameter by, an aortic filter delivery catheter tube system 1710; next, a prosthetic valve delivery tube system 1720 follows as diameter increases or catheter and the prosthetic valve delivery system 1720 is surrounded by the outer pericath catheter 1600 providing vision, Referring now to FIG. 18, there is shown deployment of a J-tipped (by way of example) guide wire 150 (central guide wire 150 above) from the telescoping/multi-channel pericath 1600 through a detective aortic heart valve 1.65 and deployment of the, 1 portion 155 of the tip of the guide wire 150 as it is advanced, under ultrasound vision into the ascending aorta 180. The J tip may prevent any inadvertent damage to the aortic walls: and deploys automatically. The left atrium chamber of the heart 120 is also shown and well as the mitral valve 195 (to be discussed later herein). The myocardium 110 surrounds the left ventricle 115 and the left ventricular apex 140 is also shown as the entry point of the pericath 1600.

Figure 19:
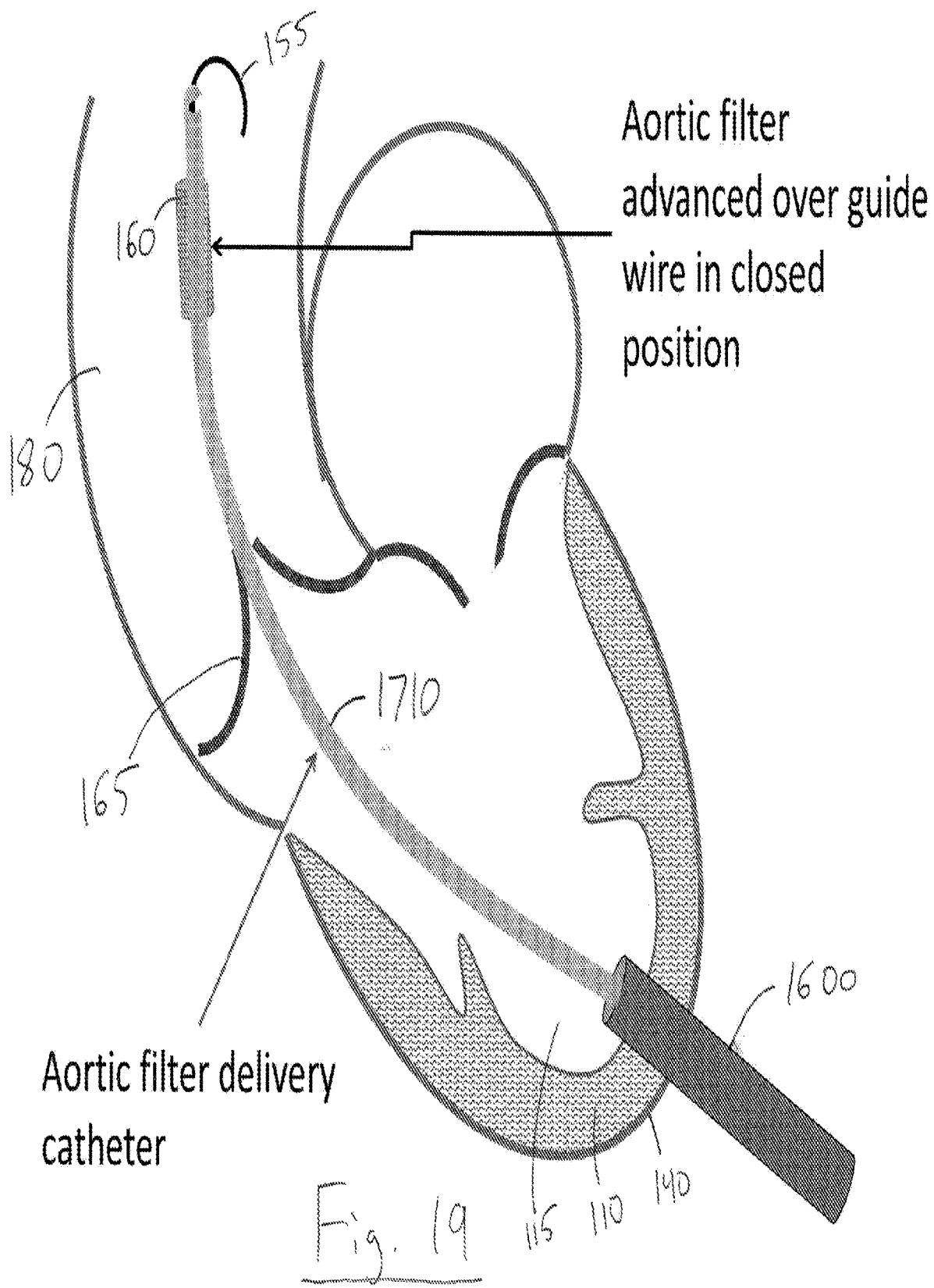
FIG. 19 shows a first delivery of the next layer of the pericath showing a tube or catheter for pushing an undeployed aortic filter advanced over the guide wire to a position in the ascending aorta to filter blood (when opened like an umbrella) and collect particulate material such as plaque.

FIG. 19 shows a first delivery of the next layer of the pericath 1600 showing a tube or delivery catheter 1710 for pushing an undeployed aortic filler 160 advanced over the guide wire 150 with J-tip 155 to a position in the ascending aorta 150 to filter blood (when opened like an umbrella] and collect particulate material such as plaque. The delivery catheter passes through defective aortic valve 165 and does not impact its operation and, as suggested before, may improve its operation by helping when the valve closes off backflow of blood. How, As suggested, but not show, the aortic filter 1.60 may be a series of filters, 160-1 and 160-2 (not shown) such as at tandem filter or two filters in series within the ascending aorta 180. (Whatever the-first aortic filter does not capture in the form of stroke-causing material may be captured by the next filter in line.) The two filters may be delivered by the same delivery system. The aortic filter catheter or delivery system may have a circumferential ultrasound transducer for detection, of particulate or emboli matter captured by the filter or which passes to the next filter in line and is captured there. A further feature is the concept of an aortic valve balloon. Such as aortic valve balloon may be positioned and have ultrasound and/or a pressure transducer to gauge the amount of pressure applied circumferentially to the walls of the aorta during balloon inflation and valve deployment.

in a similar manner, the closure device discussed herein for closure of the myocardium comprising a distal and proximal pad may have monitoring devices including but not limited to ultrasound transducer or Raman spectroscopy devices or pressure transducers to monitor, for example, the amount of squeezing applied under vision of a proximal pad to a distal pad before the insulation is removed and the pigtails deployed. The instruments may be left permanently in the closure device or the aortic valve (singular or tandem) for long-term' monitoring.

Figure 20:
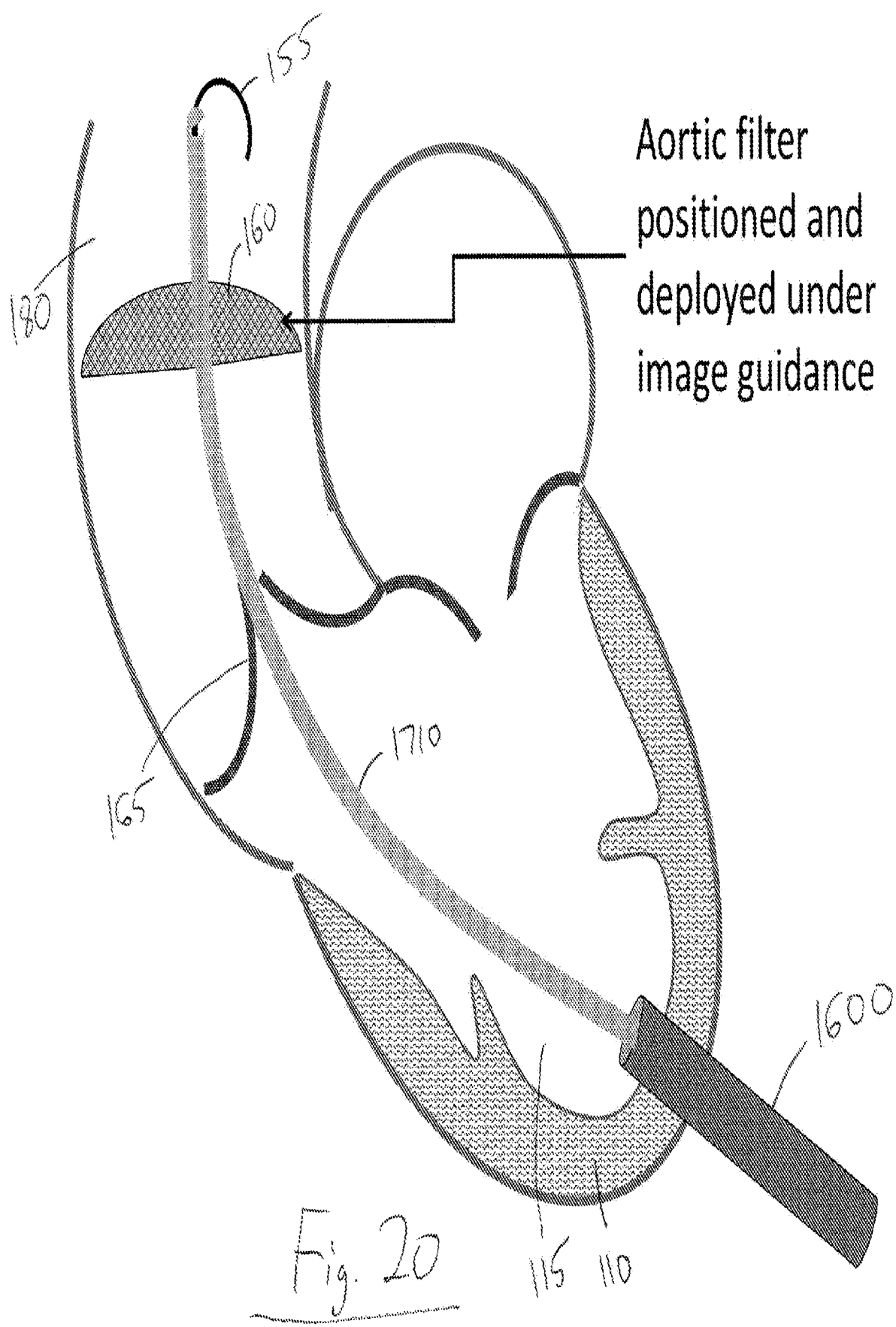
FIG. 20 shows positioning and. deploying (opening) the aortic filter for a series of filters in alternative embodiments) like an umbrella and so the aortic filter may extend the entire diameter of the ascending: aorta above the defective heart valve and be deployed under ultrasound image guidance.
Figure 21:
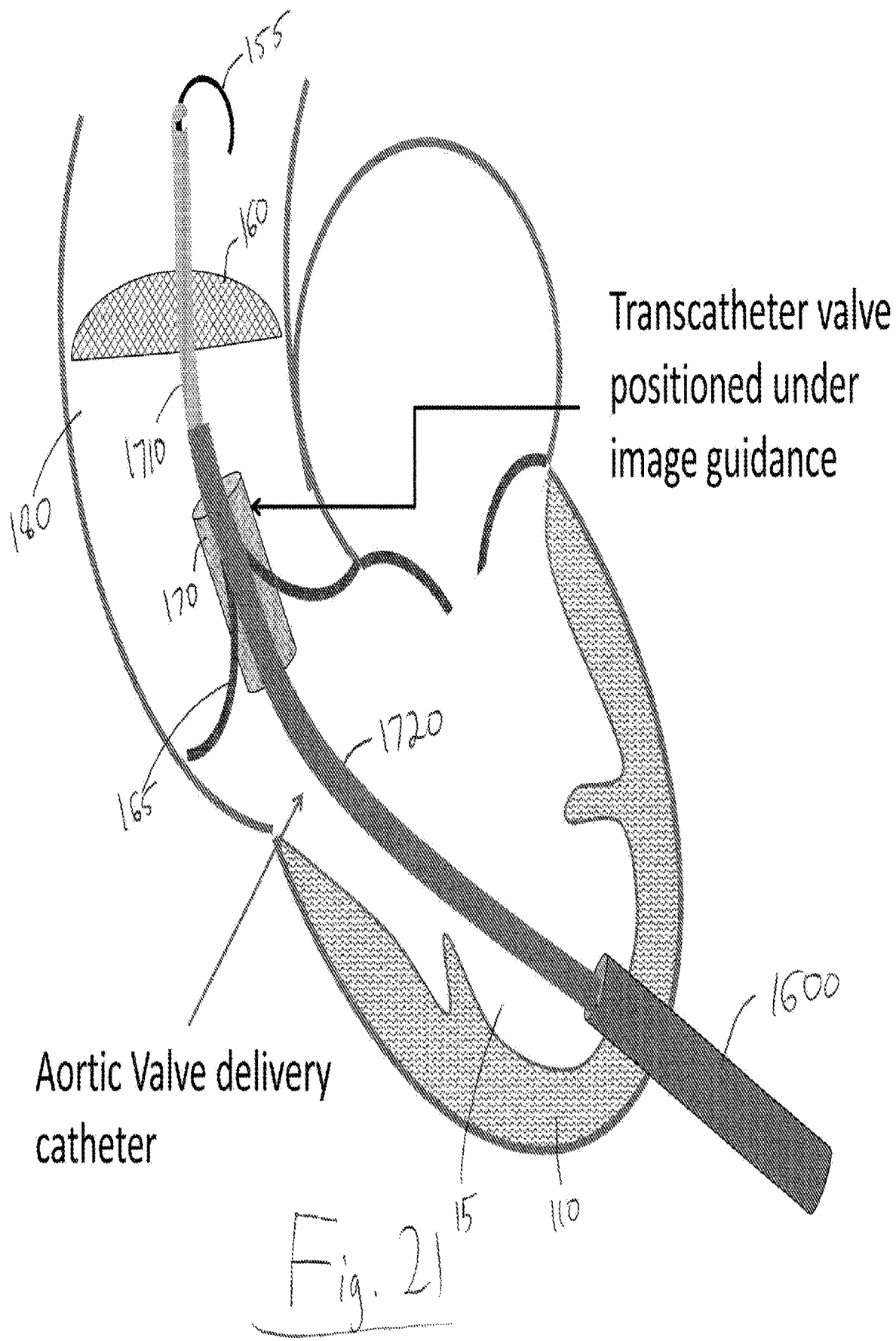
FIG. 21 shows the second delivery of the next diameter catheter tube (as it slides forward with the delivery system) for positioning and replacing the defective valve which prosthesis and. defective valve remain in position until deployed or expanded like a balloon. The defective valve may operate better even given the prosthesis delivery system because a problem may be that the detective valve does not close tightly so as to deliver blood to the body. The prosthesis delivery system may plug any gap left by o operation of the defective aortic valve.

Referring now to FIG. 20, there is shown the positioning and deploying (opening) of the aortic filter 160 (or a series of plaque-catching filters in alternative embodiments)' like an umbrella and so the aortic filter may extend the entire diameter of the ascending aorta above the defective heart valve 165 and be deployed under ultrasound image guidance. Moreover, the filter 160 may be viewed under ultrasound vision, with or without contrast agent as a matter of choice, for blood leakage outside the diameter of the umbrella filter 160 and carry plaque to the brain causing a stroke, FIG. 21 shows the second delivery of the next diameter catheter tube 1720 (as it slides forward with the delivery system) for positioning and replacing the defective valve 165 which prosthesis 170 and defective valve remain in position until deployed or expanded like a balloon or reshaped with a MEMS from an elongated cylinder to a short, fat cylinder, replacing the defective valve 165. The defective valve 165 may operate better even given the prosthesis delivery system 1720 and prosthesis 170 because a problem may be that the defective valve 1.65 does not close tightly so as to deliver blood to the body. The prosthesis delivery system 170 may plug any gap left by operation of the defective aortic valve 165 and the defective valve better prevent backflow of blood (and loss of blood pressure to the brain). Delivery system 1720 is a tube that travels over delivery system tube 1710 which in turn travels over guide wire 150 (represented by) tip 155).

Figure 22:
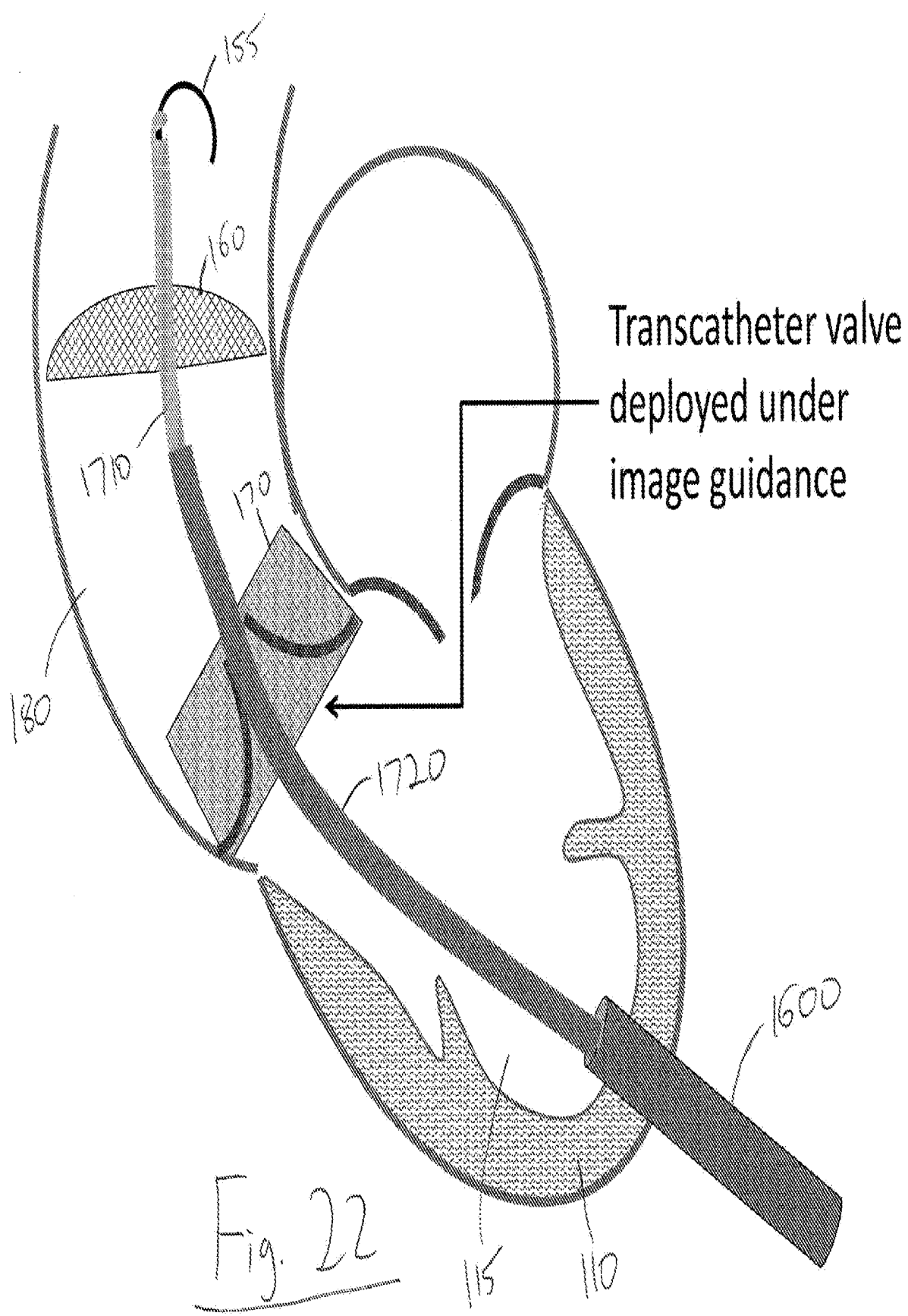
FIG. 22 shows deployment of the transcatheter valve (by changing its shape from narrow cylindrical to wide, short cylindrical or by releasing liquid as to-fill file cylinder "balloon" and, as it is deployed, the defective valve is pushed to an open position and becomes part, of the aortic wall. Meanwhile, deployment of the new transcatheter valve (mammal or artificial) should fill the entire gap above the left ventricle outflow tract, for example, like a balloon or by changing shape (for example, using a MEMS) under ultrasound image guidance. No delivery system catheter tubes have been removed yet (for the aortic tiller or the prosthesis).

FIG. 22 shows deployment of the transcatheter valve 170 (by changing Its shape from narrow cylindrical to wide, short cylindrical or by releasing liquid as to fill the cylinder "balloon" and as it is deployed, the defective valve 165 (not shown) is pushed to an open position and becomes part of the aortic wall. Meanwhile, deployment of the new transcatheter valve 170 (mammal or artificial) should fill the entire gap above the left, ventricle-outflow tract 185 (not shown), for example, like a balloon or by changing shape (for example, using a MEMS) under ultrasound image guidance. No delivery system catheter tubes have been removed yet (for the aortic filter 160 or the cardiac valve prosthesis that has just been deployed 170).

Figure 23:
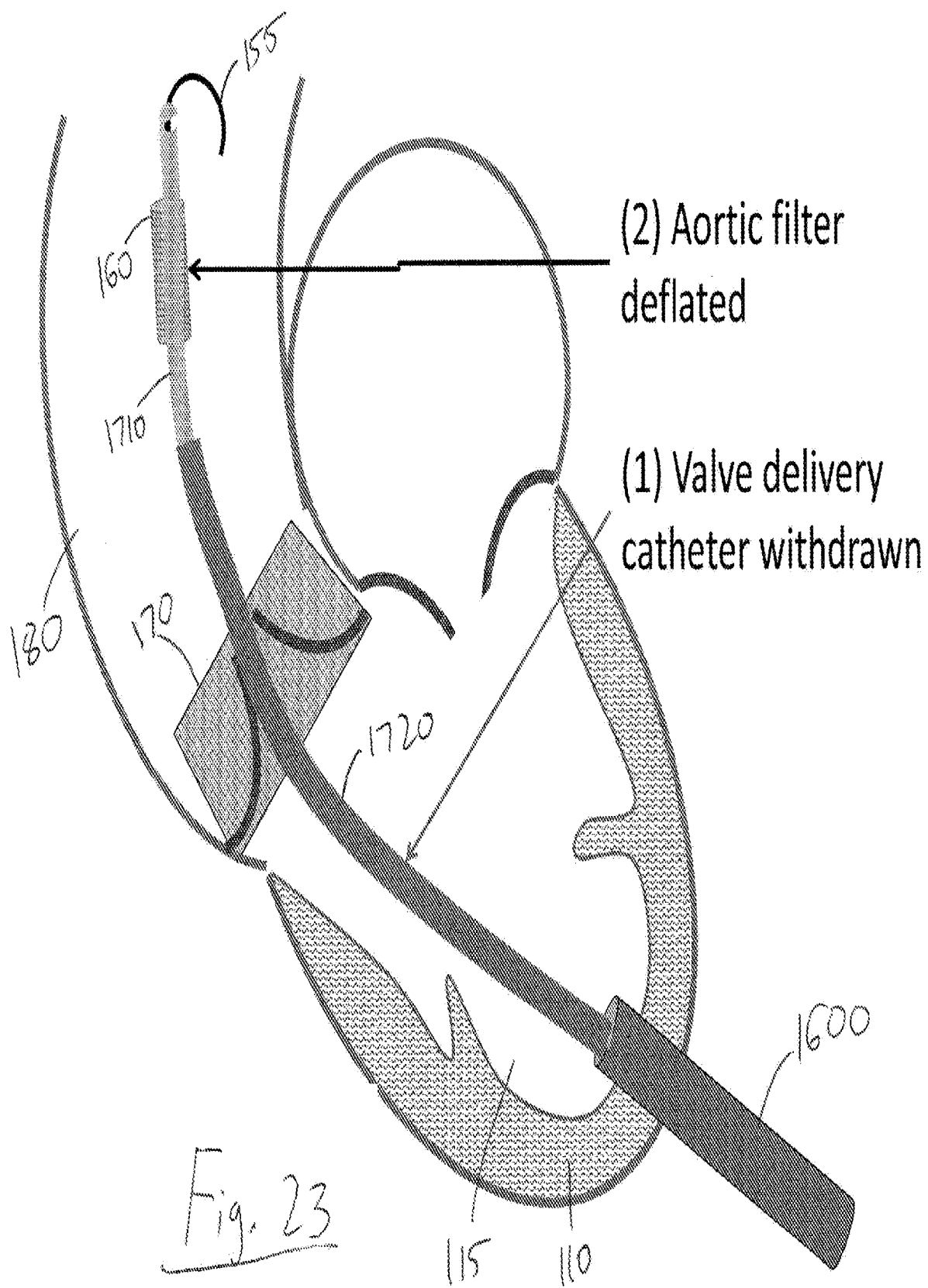
FIG. 23 shows I) valve delivery catheter withdrawal, now that the new aortic valve is functioning and 2) aortic filter deflation (like collapse of an umbrella) and subsequent removal of delivery system (not shown). The deflation of the umbrella should capture any captured particulate matter inside its deflated interior and not permit any plaque to escape.

FIG. 23 shows 1) valve delivery catheter 170 withdrawal within prosthesis delivery tube 1720, now that the new aortic valve 170 is functioning and 2) aortic filter 160 deflation (like collapse of an umbrella) and concurrent removal of delivery system 1710 (not shown). The deflation of the umbrella filter 160 should capture any captured particulate matter inside its deflated interior and not permit any plaque to escape, FIG. 24A through FIG. 24D provide details.

Figure 24A:
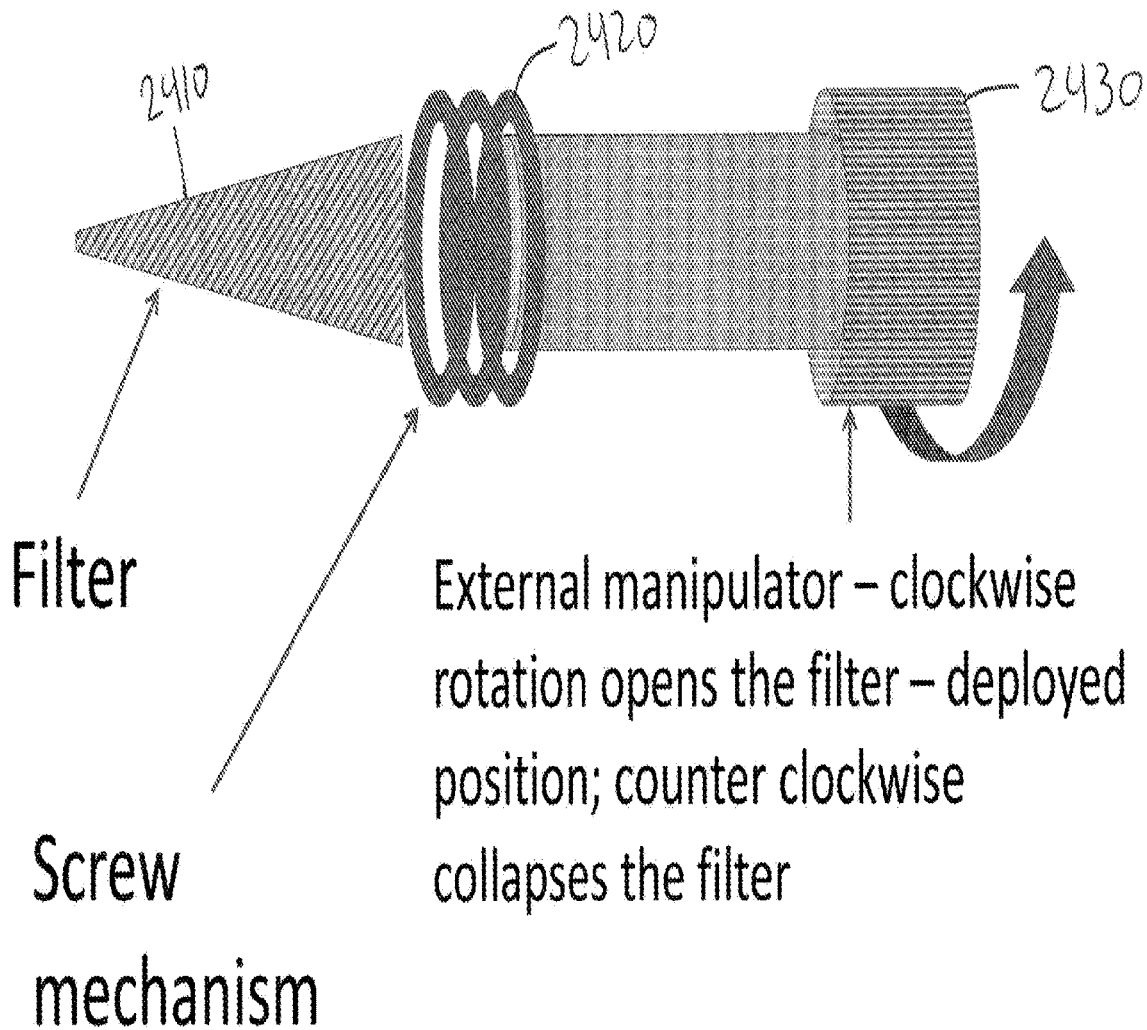
FIG. 24A through FIG. 24D provide details.

FIG. 24A provides exemplary aortic filter 2410, 2420, 2430 structural detail, the system 2400 comprising—closed in dwelling position; architecture and mechanism similar to operation of an. umbrella. The distal end 2410 comprises an umbrella filter followed by a screw mechanism 2420 and an external manipulator 2430 is used to open and close the umbrella 2410, For example, clockwise rotation may open the umbrella filter 2410 into a deployed position in the ascending aorta 180 (by moving umbrella-like spokes (not shown) and counter-clockwise rotation may close the umbrella filter 2410 capturing any particulate material for removal via the catheter delivery system.

Figure 24B:
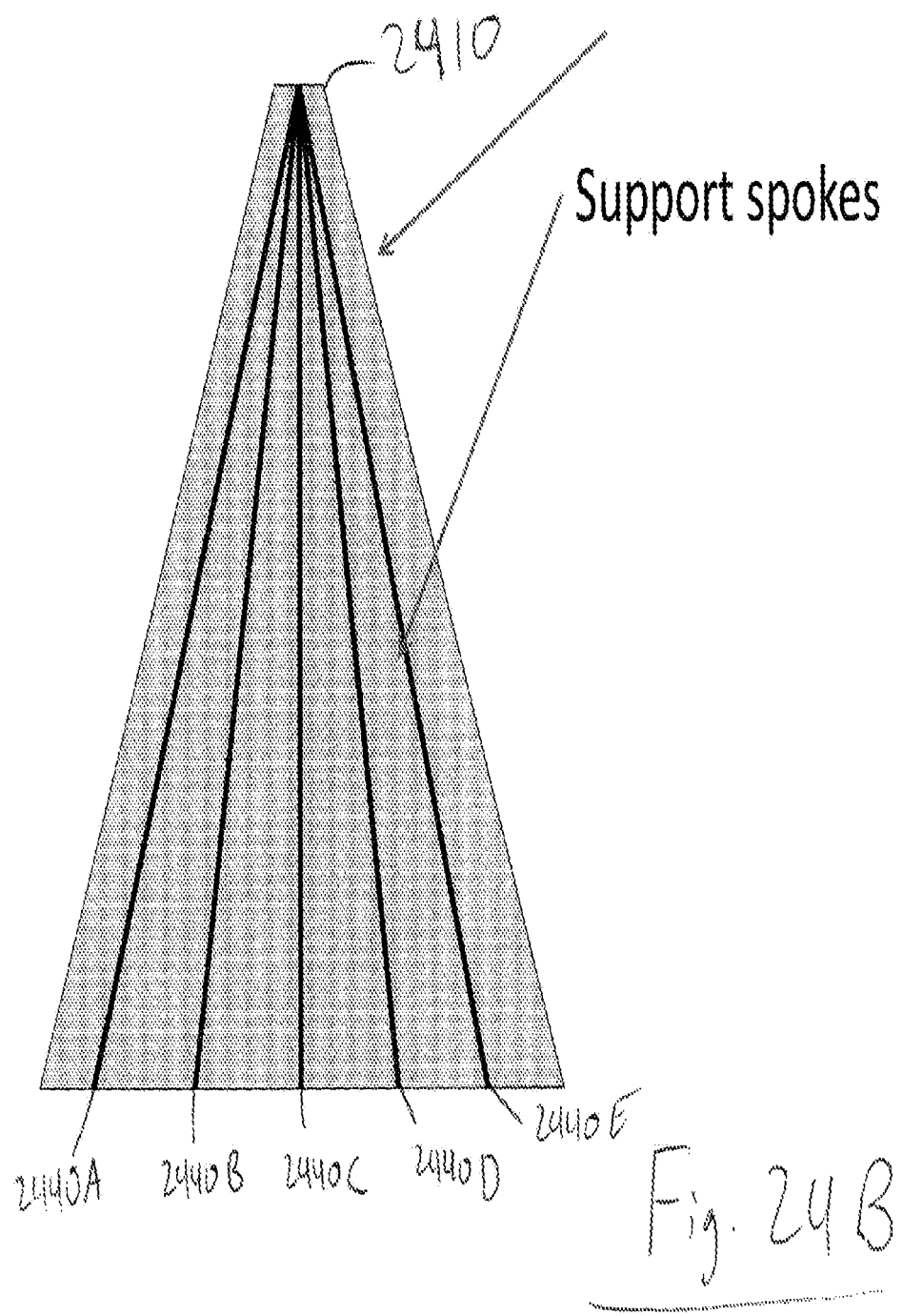

FIG. 24B provides a detailed side cut-away view of the umbrella aortic filter 2410 comprising support spokes 2440A, 2440B, 2440C, 2440D, 2440E and further support spokes as needed such as eight support spokes in total like an umbrella for opening and deploying the aortic filter 2410 or collapsing the filter 2410, the, for example, eight spokes being opened and closed by the twisting represented by FIG. 24A in clockwise and counter-clockwise directions.

Figure 24C:
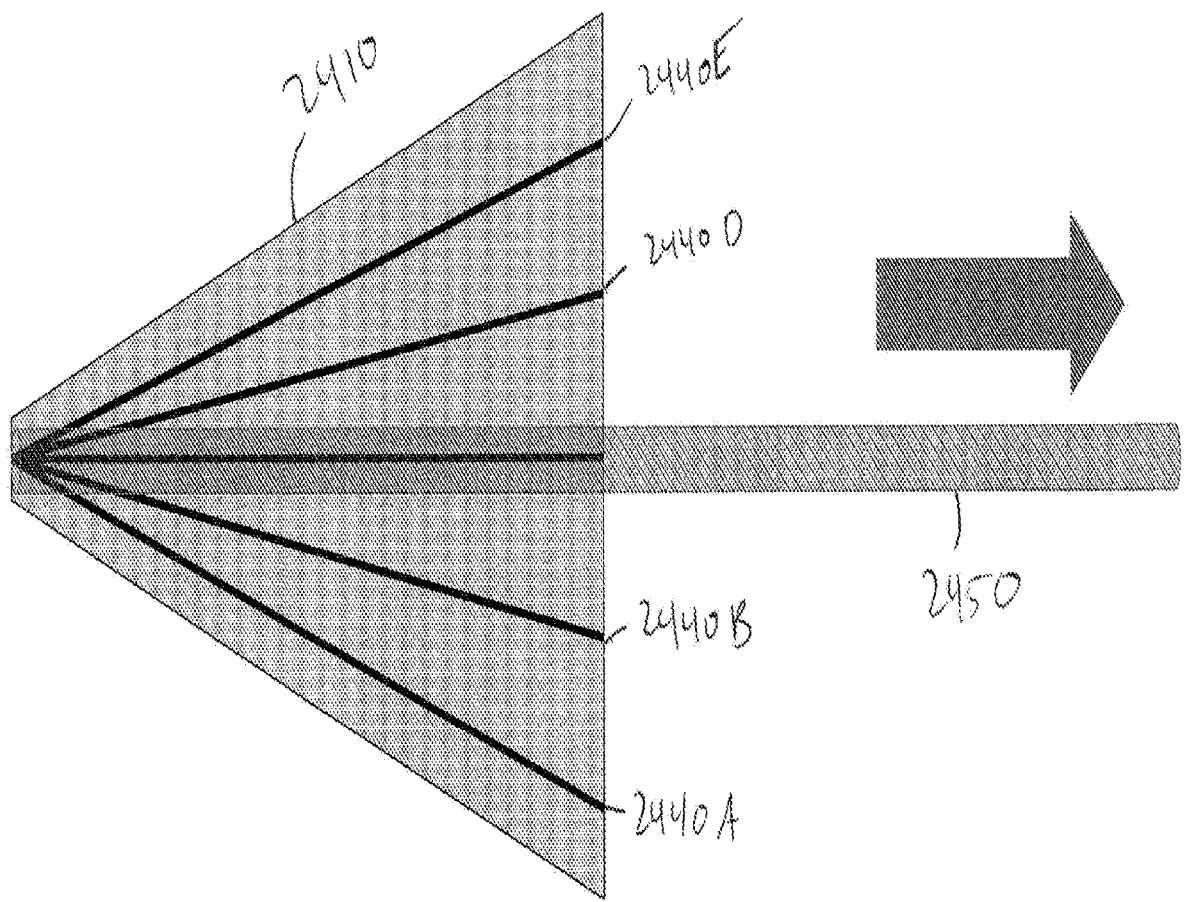

FIG. 24C shows a typical umbrella filter 2410 retraction of the delivery system 2450 to open the aortic filter 2410 via the spokes of FIG. 24B. The arrow points in the direction of the delivery tube 2450 in opening the aortic filter 2410 to its widest diameter possible without damaging aortic walls but precluding leakage of blood from leaking around the open umbrella within the aorta.

Figure 24D:
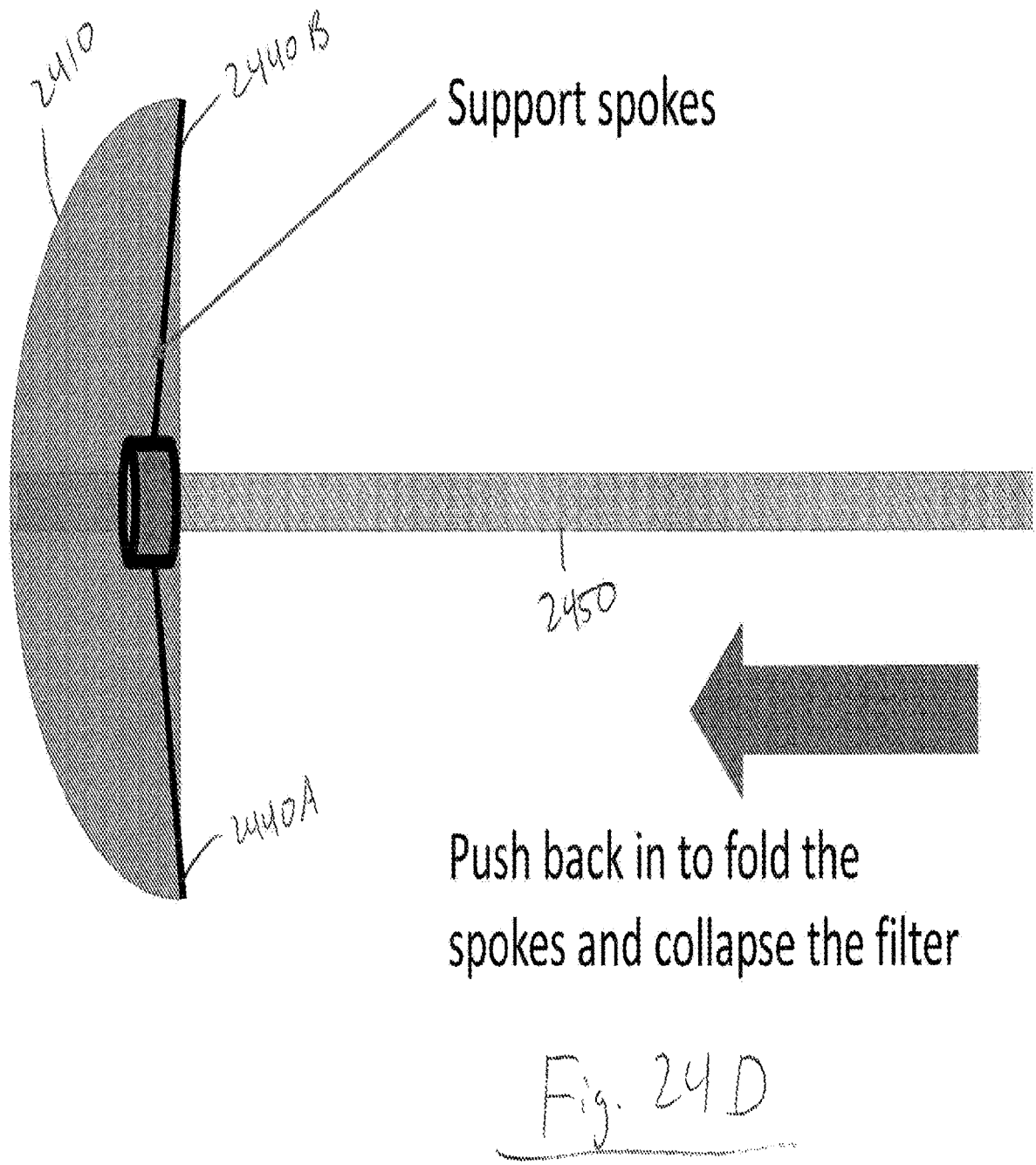

FIG. 24D shows pushing back to fold the spokes and collapse the aortic filter 2410, the arrow again showing the exemplary direction of the delivery tube 2450 to collapse the filter 2410.

Figure 25A:
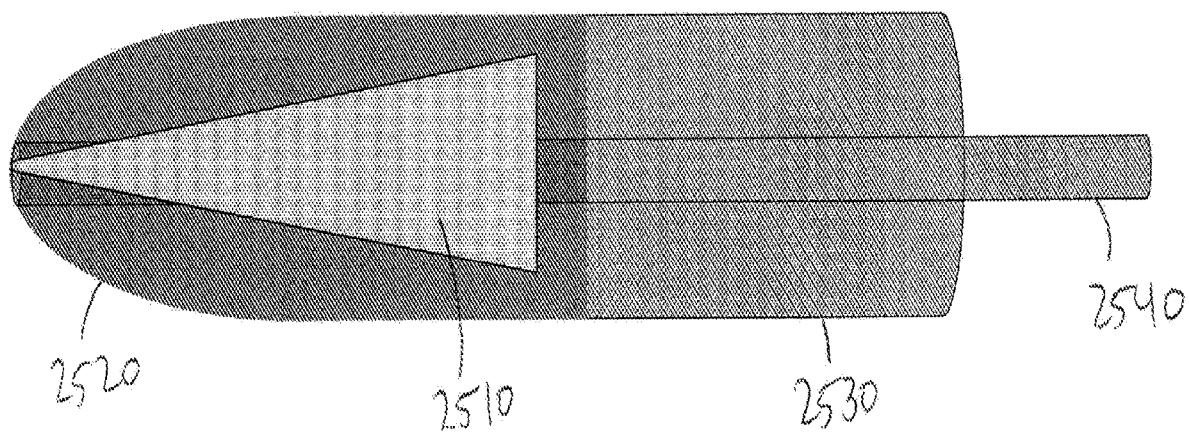
FIG. 25 A shows an alternative aortic filter mechanism comprising; a front hood. The filter delivery catheter is this embodiment has a. front hood where the collapsed filter resides during transfer to an optimal location in the ascending aorta. Once located there under ultrasound vision, a portion of the delivery catheter is retracted to open the filter. An advantage of this embodiment is that the front hood may prevent any unwanted leakage of captured particulate matter such as plaque.
FIG. 25B shows 1) the aortic filter of FIG. 25A pulled back out of the hood (in a direction toward the skin surface) to permit expansion into a filter that fits the entire diameter of the ascending aorta and 2) pushing the hood back collapses the filter into the hood that may capture any particulate matter by the aortic filter inside the filter and inside protective hood portions.
Figure 25B:
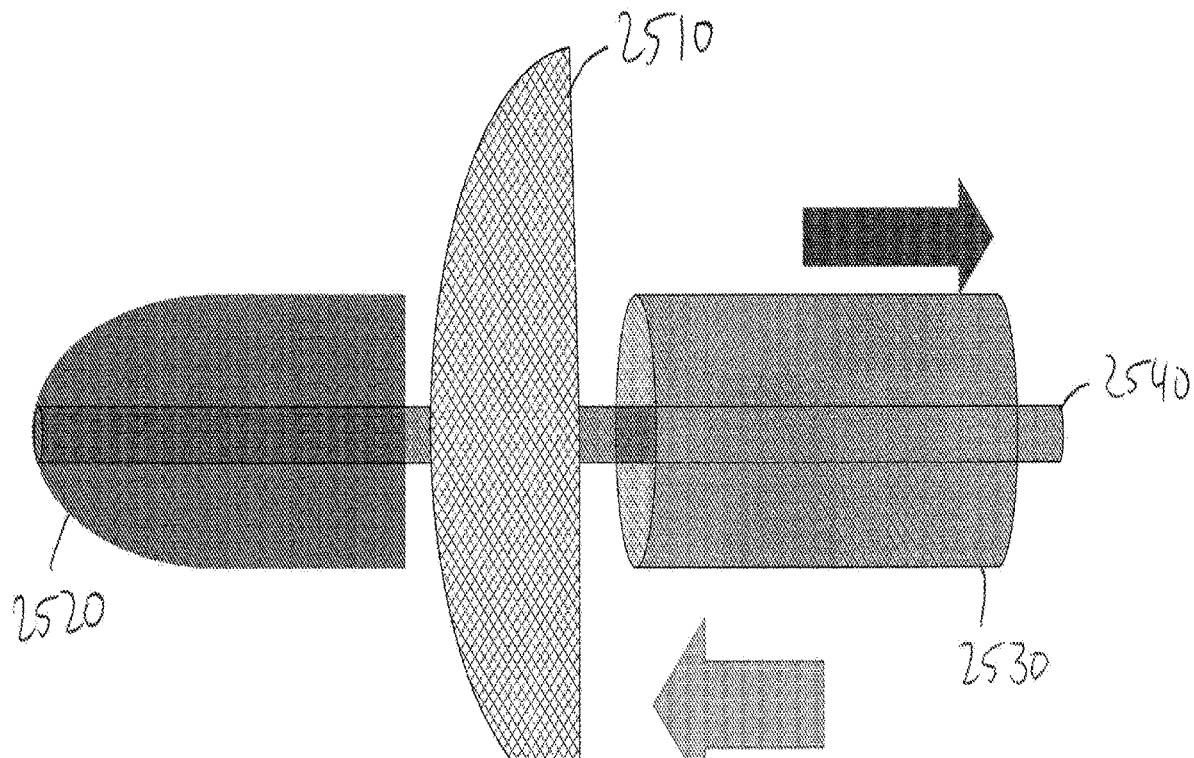

Referring now to FIGS. 25A and 25B, there is first shown in FIG. 25A an alternative aortic filter mechanism 2500 comprising a front hood 2520. The filter delivery catheter 2540 in this embodiment has a front hood 2520 where the collapsed filter 2510 resides during transfer to an optimal location in the ascending aorta 180. Once located thereunder ultrasound vision, a portion-of the delivery catheter is retracted to open the filter 2510. An advantage of this embodiment is that the front" hood 2520 may prevent any unwanted leakage of captured particulate matter such as plague.

FIG. 25B shows 1) the aortic filter 2510 of FIG. 25 A pulled back out of the hood 2520 (in a direction toward the skin surface) to permit expansion into a filter 2510 that fits the entire diameter of the a ascending aorta 180 and 2) pushing the hood back 2520 collapses the filter into the hood 2520 broken, away from rear delivery portion '2540. The combination of closing hood 2520 back onto rear portion 2530 may capture any particulate matter by the aortic filter 2510 inside the filter 2510 and inside protective hood portions 2520 and 2530, The arrows denote deployment of .the filter 2510 (gray arrow and gray rear portion) and collapse of the filter (black arrow and back front hood) by pulling on delivery tube/catheter 2540.

Figure 26:
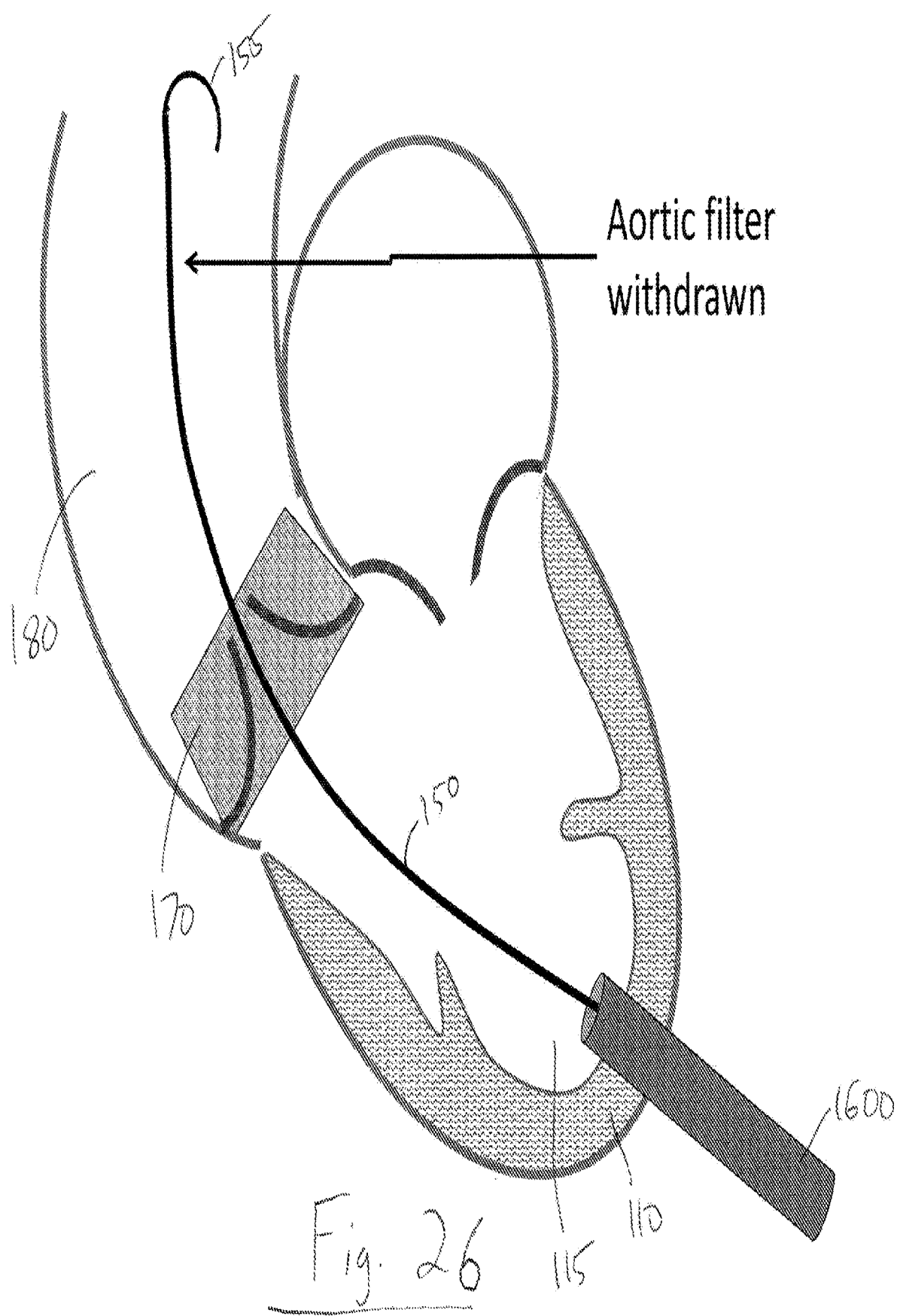
FIG. 26 shows that the aortic filter may be withdrawn via delivery tube over the guide wire and leaves the J-tip un-straightened and the prosthesis replacement heart valve in operation. The delivery tube for the new heart valve may also be withdrawn at the same time.

FIG. 26 shows that the aortic filter 160 may be withdrawn via its delivery tube 1710 (not shown) over the guide wire 150 and leaves the J-tip 155 un-straightened and the prosthesis replacement heart valve 170 in operation. The aortic filter (not shown), being collapsed will not impact, the operation of the new heart valve 170, The delivery tube 1720 for the new heart valve may also be withdrawn at the same time leaving the J-tipped guide wire 150, 155.

FIG. 27 shows the further removal or withdrawal of the guide wire 150, 155 (all delivery catheter tubes also having been removed) leaving the prosthesis new replacement heart valve 170 in place and the pericath 1600 still protruding into the left ventricular space 115 at an angle at the left ventricular apex 140.

The following figures will demonstrate closure of the myocardial angular opening via a closure device introduced through the pericath 1600.

FIG. 28 shows a similar figure to FIG. 27 with a closure device contained within the pericath 1600 for delivery via the distal (patient) end under image guidance. The pericath 1600 is now withdrawn to merely serve as a plug to prevent leakage of blood via the myocardium 110.

FIGS. 29A and 29B relate to a closure device for closing the angular hole formed in the myocardium 110.

FIG. 29A shows an exemplary closure device arrangement comprising a distal pad and a proximal pad that may be deployed via the pericath 1600 of FIG. 28. Two spokes or catheter tubes 2930, 2940 are used under vision to move the distal pad 2910 and proximal pad 2920 into place at the myocardium 110 as will be described by the following figures.

FIG. 29B shows use of the partial view pericath 2950 to deliver the closure device 2910, 2920, 2930, 2940, 2945 through the myocardial wall of the left ventricular apex 140 (apical myocardium shown with the pericath still puncturing the myocardium and plugging the hole at the left; ventricular apex 140.

FIG. 30 shows first the withdrawal of the pericath tip 2950 into the pericardial space 210 and simultaneous deployment of the distal pad 2910 and its deployment and being pulled to an open position plugging the hole by wire leads 2935, 2945. As of this time, the proximate pad 2920 has not yet been deployed, as with the aortic filter 160, the distal pad 2920 may be opened like an umbrella and will prevent any blood leakage into the pericardial space 210. The closure device distal pad 2920 is deployed by withdrawing the catheter (pericath.) and exposing the self-expanding distal pad 2920 to open automatically (per FIG. 31), Referring to FIG. 31, there is shown further movement of the pericath portion 2950 with respect to the proximal pad 2920 and simultaneous opening of the proximate pad 2920, The closure device proximal pad 2920 is deployed, by the further withdrawal of the delivery catheter (pericath) but is not yet positioned (pushed) toward the myocardium 110.

FIG. 32 now shows use of the closure device within the pericath to push the proximal pad device 2920 up against the myocardium 110 using the delivery catheter (pericath) portion 2950 to provide the pushing. The wire leads 2935, 2945 still remain within their insulation 2935 and 2945 and can be used to kelp pull the distal pad 2910 against the pushed proximal pad 2920 via respective catheter tubes (insulation) 2930. 2940 from the pericath portion 2950.

FIG. 33; shows removal of the distal pad and proximal pad retaining tubes or insulation 2730 and 2740 (like insulation on a wire), the ends of the harness wires 2735, 2745 automatically coil as the tubes 2730, 2740 are removed and leave permanent pigtails 2735, 2745 serve to hold tight the distal pad 2710 to the proximal pad 2720 with the apical myocardium 110 in between and close off any flow of blood due to blood pressure in the left ventricle 115. The tubes 2730, 2740 are shown removed from the wires which automatically pigtail.

FIG. 34 shows the periport 700 remaining in the pericardial space (cavity) 210 which may be inflated by insertion of fluid, and FIG. 34 is intended to show the removal or withdrawn of residual pericardial fluid via a syringe (not shown) deployed through, the periport 700 so that the pericardial space 210 returns to normal via the periport 700 under image guidance.

FIG. 35 shows the removal of the periport 700 leaving the prosthesis replacement heart valve in place and the myocardium 110 sealed by the closure device with pigtails (not shown).

The following features of the above-described system and method may become apparent to one. of skill in the art. The entry system for delivery of a closure device for closure of the myocardium 110 at the left ventricular apex 140 becomes a closure system. An umbrella closure device or an umbrella aortic valve may be provided in alternative embodiments. One embodiment which comes to mind is that a typical umbrella is long and thin when collapse and may require a greater distance of travel in the ascending aorta than if a filter or the left ventricular space than, if a known collapsible umbrella with bendable spokes were used and deployed in the manner of a collapsible umbrella (embodiment not shown).

A further embodiment of an aortic filter or a distal or proximate pad for closure may be referred to as a clam shell like embodiment having first and portions made by cutting a hollow sphere and folding them together like an unopened clam shell comprising two partial hemispheres. These two partial hemispheres could then be opened, for example, by a MEMS to form the aortic filter or the distal or proximal, pad closure device.

In a further closure embodiment, the central channel, of a clam shell central channel may be held open by a guide sheath having a valve. Then, the guide sheath is withdrawn and the central channel may collapse and the clam shell be equipped with an occlusive one-way valve mechanism such that the valve may collapse to prevent any blood exit.

A further alternative scenario to that just described comprises a guide sheath with a one-way valve that becomes the myocardial portal (entry at the left ventricular apex). When the closure procedure has been completed, a guide wire may be introduced through the guide sheath, the guide sheath removed via the guide wire and the clam shell closure device deployed under ultrasound vision.

FIG. 36, FIGS. 37A through 37C, FIG. 38, FIG. 39, FIG. 40, FIGS. 41. A through 41E and FIGS. 42A through 42C relate to mitral valve repair or replacement. It will be seen that similar principles, apparatus and processes are utilized for the mitral valve and, under certain circumstances and with the surgeon's discretion, these Figures show processes that may be used simultaneously with aortic valve repair or replacement as discussed above. Under vision, such as ultrasound vision, with or without use of contrast agents, varying degrees of mitral repair may be performed using the same periport devices. Potential sites of mitral intervention comprise but are not limited to comprise the annulus, the commissure (discussed in some detail), one or both leaflets and the chords among other mitral components.

FIG. 36 shows an exemplary Mitral valve repair mechanism consisting of an inner cylindrical strut inside an. outer cylindrical strut 3620, with, an elastic band 3630 mounted on the inner strut-3620 for Subsequent deployment. The intention is to capture loose leaflets of the mitral valve with the elastic band to repair a defective mitral valve which may have excess leaflet material that may be captured and banded by the elastic band (which should comprise a non-allergic material).

Figure 37:
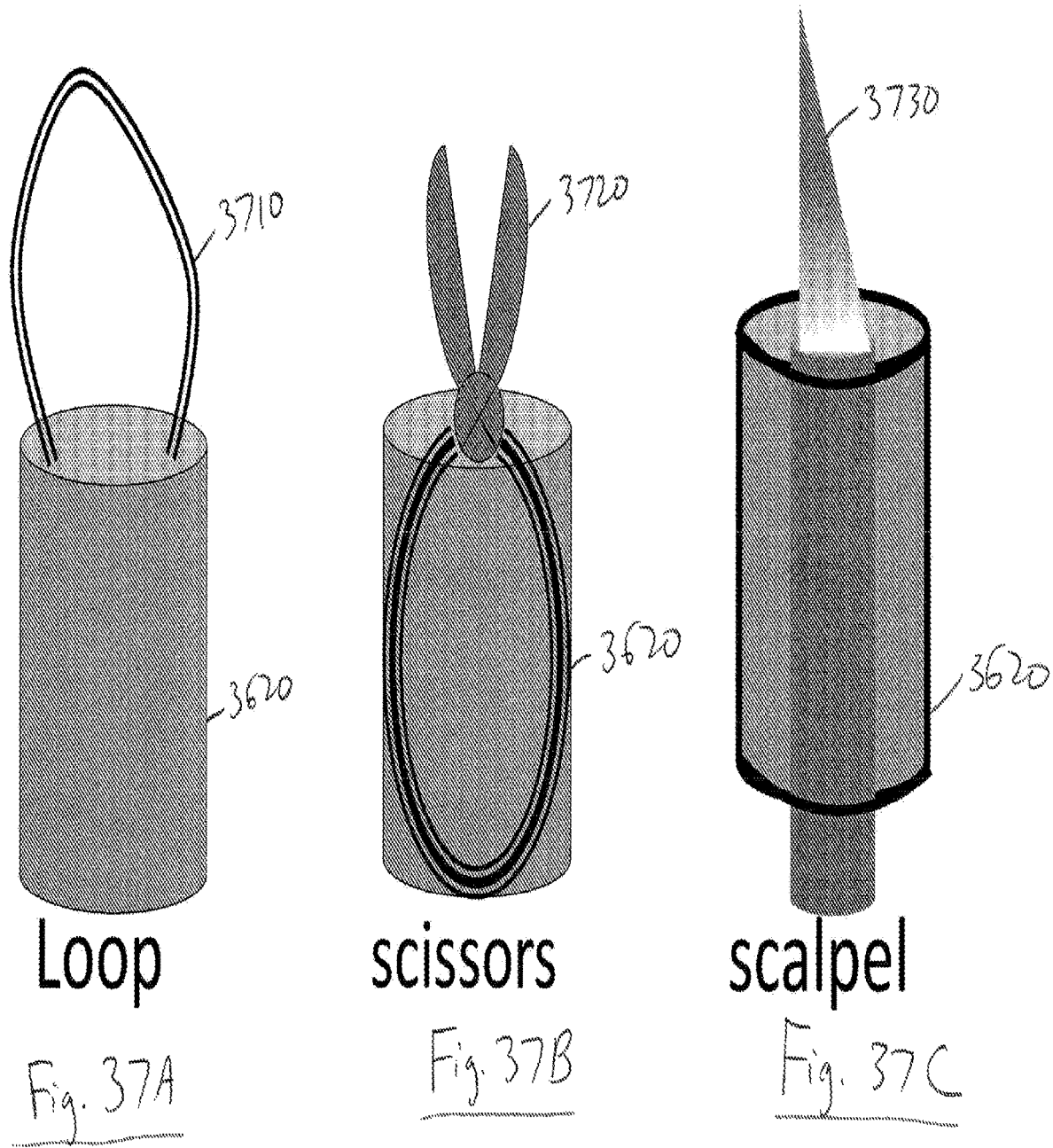

FIG. 37A, FIG. 37B, and FIG. 37C show examples of surgical tools which may be delivered to the mitral valve in the inner cylindrical strut 3620 of the mitral valve repair mechanism of FIG. 37 which may be used in conjunction with elastic band 3630 or to capture leaflet material or cut the material. For example, FIG. 37A shows a loop 3720 delivered by strut 3620 which may be used to surround and capture mitral valve leaflet material (for example, for banding or cutting). FIG. 37B shows scissors 3720 which, may be used to cut off excess leaflet material and be deployed via strut 3620. A similar tool, not shown, is a clasper that may clasp the cut excess material for removal FIG. 37C shows a scalpel 3730 which also may be used for making an incision or-cutting leaflet material of the mitral valve or for any other known purposes a mini-scalpel would-be. useful for in regard to repair of a cardiac valve such as the mitral valve. Other tools that may be delivered in the same manner via the inner strut 3620 include a suction device, an electro-cautery device, a electro-cautery device, a plunger, or other surgical tools (not shown).

FIG. 38 shows the use of a bifurcated delivery catheter (periport.) 3810 to insert a mitral valve prosthesis 3833 to replace a defective mitral valve in a similar manner to the process described above for replacement of an aortic valve except that two different paths will be followed by guide wires and delivery system tubes and the like to replace the defective mitral valve, in one embodiment not shown, two lumens of a periport 3810 (image guided catheter) may carry two different guide wires (not shown) through the ventricular apex of a myocardium 110 as discussed above. Shown in FIG. 38 is a bifurcated lumen (pair of pants legs) 3811 and 3812 forming a bifurcated front end which may be used for deployment in two, different directions from the bifurcated periport body 3810 toward, for example, the ascending aorta 180 and the mitral valve 4000 (introduced below). An atrial filter 3823 (opened like an umbrella as already discussed above) is delivered to and deployed in the ascending aorta 180 via, for example, a J-tipped guide wire 3820 and an automatically deploying J protector. The .filter delivery system, only the guide wire 3820 is shown deployed through the first opening 3811 of the bifurcated periport 3810 (in a similar manner as discussed above for an aortic valve replacement and repair). As above, the purpose of the aortic filter is to capture any particulate matter which may cause a stroke as un-filtered blood may deliver, for example, plaque .material to the brain. A prosthetic mitral valve delivery system (not shown but described above for the aortic valve) may be delivered to and deployed over a second J-tipped guide wire 3830, 3831 with the J protector automatically deploying. Prosthesis 3833 carries a mitral valve which is deployed by a slender cylinder to comprise a short fat cylinder carrying the valve 3833 to replace a defective mitral valve 3832, 4001) through the second opening of the bifurcated periport 3812, (The defective valve 3832, 4000 may be deployed and replaced in a similar manner to the aortic valve using the left ventricular apex 140 entered at an angle and the myocardium 110 closed in a similar manner as discussed above).

Referring to FIG. 39, this figure further shows the use of a bifurcated periport 3810 pant legs 3811, 3812 (or two lumens) to perform repairs on the mitral valve 3832 using the repair mechanisms depicted in. FIG. 36, using tools shown in FIG. 36 and FIGS. 37A through. 37C and other tools used under discretion of the surgeon via the second pants leg 3812 showing first and second repair mechanism delivery systems 3600. For example, one delivery system may carry scissors and another delivery system a grasper to grasp any cut leaflet material by the Scissors or scalpel of the defective mitral valve 3832. An atrial, filter 3823 is delivered to and deployed in the ascending aorta 180 through the first opening 3811 of the bifurcated periport 3810 using, for example, a J-tipped guide wire 3820, 3823, The repair mechanism or combination of repair systems is delivered to the mitral valve region 3832 through the second opening 3812 of the bifurcated periport 3810.

FIG. 40 shows the placement of a commissural stitch 4050 to reduce the opening of a mitral valve 4000 that cannot fully close comprising a first commissure 4010 and a second commissure which are open because of dilation in its leaflets where leaflet 4030 comprises a first leaflet of the mitral valve 4000 and leaflet 4040 comprises a second leaflet of the mitral valve 4000.

FIGS. 41A through 41E show a process for affecting a commissural stitch—either a corkscrew or a single stitch—delivered across two leaflets 4030 and 4040 to attempt to partially close the large opening of the mitral valve between the two leaflets.

FIG. 41A shows a delivery needle assembly 4100 with an internal, unlabeled needle inside a sheath for delivering a commissural stitch across two leaflets of a mitral valve (not shown) in FIG. 41. A.

Referring now to FIG. 41B, there is seen the needle sheath 4110 carrying a needle within, the first leaflet 4030, the second leaflet 4040 and the hollow delivery needle 4115 deployed in a circular fashion to puncture both leaflets 4030 and 4040. Moreover, the delivery needle 4115 is advanced through both leaflets 4030, 4040 of the mitral valve carrying a wire with an automatically deployed pigtail end 4230 of the suture protruding from the second leaflet 4040.

FIG. 41C shows the delivery needle 4115 being retracted out of the second leaflet 4040, leaving the suture 4120 held in place by the pigtail end 4130.

FIG. 41D shows that a pulling has occurred of the delivery needle 4115, The delivered commissural stitch 4120 with the pigtail end 4130 has been deployed from the second leaflet 4040 with the delivery needle 4115 mostly retracted and the two leaflets 4030 and 4040 still apart leaving the same sized opening. Then, the delivery needle is pulled through the first leaflet 4030 tightening the stitch, FIG. 41E shows a fully delivered commissural stitch 4120, 4140 pigtail end and 4130 pigtail end of the stitch with the delivery needle 4115 fully removed and the suture: holding the leaflets closer together. So as the delivery needle 4115 is removed, the leaflets 4030, 4040 are pulled together reducing the size of the opening in a defective mitral valve. The needle delivery assembly 4100 is then removed via the guide wire 3830 and the, J-tip 3831 straightened (not shown).

FIGS. 42 A through 42C demonstrate the use of suction to suck a portion of leaflet material 4210 into strut 3620 and then deliver elastic band 3630 to tighten the opening of the mitral valve.

FIG. 42A shows a redundant portion of a leaflet 4210 being suctioned into the inner cylinder strut 3620 carrying an elastic band 3630 via outside strut 3610 as per FIG. 36.

FIG. 42B and FIG. 42C show the redundant portion of the leaflet 4210—being suctioned into the inner cylinder strut 3620 by applying suction 4220 to gather material 4210 into the elastic band 3620 and then in FIG. 42C, the surgeon releases the elastic band 3640 to tighten around excess leaflet material 4230 taken from first or second leaflet 4210, An elastic band 3630 may be pushed off the strut 3620 and applied to the redundant portion to tighten the leaflet. The loop 3710 of FIG. 37A may be used to gather excess leaflet 4210 material.

Access to other organs, structures, and spaces can be performed in similar fashion with appropriate procedural modifications specific for the particular organs, structures or spaces.

All documents mentioned herein are incorporated, by reference herein as to any description which may be deemed essential to an understanding of illustrated and discussed aspects and embodiments of devices and methods herein.

Although the devices and methods discussed above and unmanly illustrated and described herein provide instruments that also can be adapted for performing minimally invasive diagnostic or therapeutic procedures on humans, it will be appreciated by those skilled in the art that such instruments and methods also are adaptable for use in other surgical procedures as well as in performing various veterinary surgeries. Further, while several preferred embodiments have been described using specific terms, such description is for illustrative purposes only, and it is to be understood that changes and variations may be made without departing from the spirit or scope of the following claims.

What is claimed is:

1. A catheter comprising:
   an elongate member comprising a hollow body; and
   an ultrasound transducer comprising a proximal end and a distal end and attached to an exterior sidewall of the elongate member at the proximal end, the ultrasound transducer configured to move from a retracted configuration to a deployed configuration that is raised from the elongate member by pivoting about the proximal end to move the distal end away from the elongate member, wherein when in the retracted configuration the ultrasound transducer is located lengthwise along the exterior sidewall of the elongate member and, when in the deployed configuration, the transducer extends from the exterior sidewall of the elongate member at an angle to the exterior sidewall of the elongate member, and wherein the transducer is configured to deploy and/or retract to achieve a desired imaging field.

2. The catheter of claim 1, wherein in the deployed configuration, the ultrasound transducer produces a forward looking imaging field.

3. The catheter of claim 2, wherein in the deployed configuration, the ultrasound transducer produces a forward looking imaging field that includes a portion of the elongate member in the imaging field.

4. The catheter of claim 1, wherein the ultrasound transducer in the deployed configuration is positioned at an angle greater than 45 degrees with respect to the sidewall of the elongate member.

5. The catheter of claim 1, wherein a distal portion of the elongate body is bendable with respect to a proximal portion of the elongate body.

6. The catheter of claim 1, further comprising a mechanical pulley-system operable to move the ultrasound transducer from the retracted configuration to the deployed configuration.

7. A system comprising:
   a first elongate member comprising a first hollow body;
   an ultrasound transducer comprising a proximal end and a distal end and attached to an exterior sidewall of the first elongate member at the proximal end, the ultrasound transducer configured to move from a retracted configuration to a deployed configuration that is raised from the first elongate member by pivoting about the proximal end to move the distal end away from the first elongate member, wherein when in the retracted configuration the ultrasound transducer is located lengthwise along the exterior sidewall of the elongate member and, when in the deployed configuration, the transducer extends from the exterior sidewall of the elongate member at an angle to the exterior sidewall of the elongate member, and wherein the transducer is configured to deploy and/or retract to achieve a desired imaging field;
   a second elongate member comprising a second hollow body, wherein the second elongate member is sized to fit within the first hollow body and wherein the second elongate member is bendable and operable to deliver a prosthetic valve; and
   a third elongate member comprising a third hollow body, wherein the third elongate member is sized to fit within the second hollow body and operable to deliver an aortic filter.

8. The system of claim 7, wherein the system further comprises a ventricular closure device.

9. The system of claim 7, wherein a distal portion of the second elongate body is bendable with respect to a proximal portion of the second elongate body.

10. The system of claim 7, wherein the system is configured to be advanced over a guidewire.

11. The system of claim 7, wherein the first elongate member, the second elongate member, and the third elongate member are configured with a telescoping arrangement with respect to each other.

12. A method for replacing a cardiac valve, the method comprising:
   conducting a valve replacement procedure on a subject in a minimally invasive manner, wherein a heart valve is replaced without performing an open-heart procedure on the subject by advancing a hollow elongate member through a chest wall and into a pericardium of a heart of the subject, the elongate member comprising an ultrasound transducer comprising a proximal end and a distal end and attached to an exterior sidewall of the hollow elongate member at the proximal end, the ultrasound transducer configured to move from a retracted configuration to a deployed configuration that is raised from the hollow elongate member by pivoting about the proximal end to move the distal end away from the hollow elongate member,
   wherein when in the retracted configuration the ultrasound transducer is located lengthwise along the exterior sidewall of the elongate member and, when in the deployed configuration, the transducer extends from the exterior sidewall of the elongate member at an angle to the exterior sidewall of the elongate member, and wherein the transducer is configured to deploy and/or retract to achieve a desired imaging field.

13. The method of claim 12, wherein conducting further comprises:
   advancing a needle through the elongate member and through the pericardium into an interior of the heart, wherein the advancing is performed under image guidance from the ultrasound transducer of the hollow elongate member;
   advancing the hollow elongate member into the heart via an opening created by the needle; and
   advancing one more additional devices through the hollow elongate member and into the interior of the heart to conduct the valve replacement procedure.

14. The method of claim 13, further comprising removing the one more additional devices and advancing a closure device through the hollow elongate member to close the opening in the heart created by the needle.

15. The method of claim 14, wherein the hollow elongate member is removed from the opening in the heart prior to operating the closure device to close the opening in the heart created by the needle.

16. The method of claim 15, wherein the closure device comprises a plurality of closure members.

17. The method of claim 15, wherein the hollow elongate member is removed to the pericardium.

18. The method of claim 17, wherein the hollow elongate member is removed from the subject.

\* \* \* \* \*